(12) United States Patent
Tatsuoka et al.

(10) Patent No.: US 6,337,397 B1
(45) Date of Patent: Jan. 8, 2002

(54) PYRIMIDINE DERIVATIVES AND THEIR SALTS, USEFUL FOR MAKING BENZOXAZEPINE DERIVATIVES

(75) Inventors: Toshio Tatsuoka, Nishinomiya; Katsuhide Kamei, Ibaraki; Noriko Maeda; Teruyoshi Inoue, both of Takatsuki, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/726,481

(22) Filed: Dec. 1, 2000

Related U.S. Application Data

(62) Division of application No. 09/306,995, filed on May 7, 1999, now Pat. No. 6,187,769, which is a continuation of application No. 08/727,391, filed as application No. PCT/JP96/00294 on Feb. 9, 1996, now abandoned.

(30) Foreign Application Priority Data

Feb. 10, 1995 (JP) ................................................ 7-58307
Mar. 1, 1995 (JP) ................................................ 7-41836

(51) Int. Cl.$^7$ ................... C07D 401/04; C07D 401/06; A61P 25/22
(52) U.S. Cl. ..................... 544/242; 544/319; 544/333; 544/334
(58) Field of Search ................. 544/333, 319, 544/334, 242

(56) References Cited

U.S. PATENT DOCUMENTS 5,196,428 A    3/1993   Meanwell ................... 544/126

FOREIGN PATENT DOCUMENTS

| EP | 0 376 633 A2 | 7/1990 |
| EP | 0 463 810 A1 | 1/1992 |
| HU | 160405 | 9/1971 |
| JP | 46-32664 | 9/1971 |
| JP | 2-256671 | 10/1990 |
| JP | 5-51370 | 3/1993 |

OTHER PUBLICATIONS

Meanwell et al., "Inhibitors of Blood Platelet cAMP Phosphodiesterase. 4. Structural Variation of the Side–Chain Terminus . . . Derivatives", J. Med. Chem., 36:3251–3264, 1993.

Monkovic et al., "Substituted Benzamides. 1. Potential Nondopaminergic Antogonists of Chemotherapy–Induced Nausea and Emesis", J. Med. Chem., 31:1548–1558 (1988).

Peroutka, "Pharmacological Differentiation and Characterization of 5–HT$_{1A}$, . . . Frontal Cortex", J. of Neurochem., 42(2):529–539, 1986.

Copy of European Search Report dated Apr. 22, 1998.

Notice of Reasons for Rejection mailed May 30, 2000, in Japanese Patent Application No. 8–524145 (w/ English Translation).

Primary Examiner—Richard L. Raymond
Assistant Examiner—Kahsay Habte
(74) Attorney, Agent, or Firm—Burns, Doane, Swecker & Mathis, L.L.P.

(57) ABSTRACT

A benzoxazepine derivative having the general formula (I) and its salts and medicaments containing the same as effective ingredients:

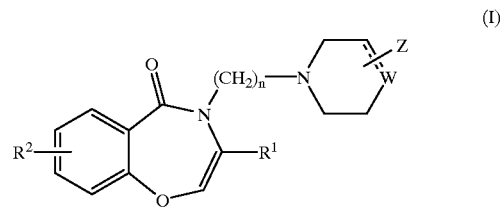

(I)

wherein, n is an integer of 2 to 5, $R^1$ indicates a hydrogen atom, halogen atom, $C_1$ to $C_4$ lower alkyl group, $C_1$ to $C_4$ lower alkoxyalkyl group, $C_1$ to $C_4$ halogenoalkyl group, cyano group, or ester group, $R^2$ indicates a hydrogen atom, halogen atom, $C_1$ to $C_4$ lower alkyl group, $C_1$ to $C_4$ lower alkoxy group, or hydroxy group, a dotted line indicates the presence or absence of a binding bond, W indicates C, CH, or $CH_2$ or a nitrogen atom, provided that, when W is a nitrogen atom, Z is bonded to W and the dotted line indicates the absence of a bond, and Z indicates an unsubstituted or substituted aromatic hydrocarbon ring group or an unsubstituted or substituted heterocyclic group).

20 Claims, No Drawings

PYRIMIDINE DERIVATIVES AND THEIR SALTS, USEFUL FOR MAKING BENZOXAZEPINE DERIVATIVES

CROSS-REFERENCE TO RELATED APPLICATIONS

This application is a divisional of application Ser. No. 09/306,995, filed May 7, 1999 now U.S. Pat. No. 6,187,769, which is a continuation of application Ser. No. 08/727,391, filed Oct. 10, 1996 now abandoned, which was a national stage filing of PCT International Application No. PCT/JP96/00294, filed Feb. 9, 1996. The International Application was published by the International Bureau in Japanese as Publication No. WO 96/24594 on Aug. 15, 1996.

TECHNICAL FIELD

The present invention relates to novel benzoxazepine derivatives and their salts. More particularly, it relates to novel benzoxazepine derivatives and their salts useful as medicaments for the treatment of anxiety neurosis, phobias, obsessive-compulsive disorders, schizophrenia, post-cardiac trauma stress disorders, depression disorders, psychosomatic disorders and other psychoneurotic disorders, eating disorders, menopausal disorders, infantile autism and other disorders, and also emesis or disorders involving the cerebral circulatory system accompanying cerebral infarction and cerebral hemorrhage and also medicaments containing these as effective ingredients and also novel synthetic intermediates of the same.

BACKGROUND ART

In the past, anxiety disorders, phobias, obsessive-compulsive disorders, etc. have been treated using diazepam, oxazepam, and other benzodiazepine-based medicaments. However, these benzodiazepine-based medicaments have side effects such as drowsiness, muscle relaxation, and dependency. To lighten these side effects, buspirone, tandoopirone, and other serotonergic agents have been developed as anxiolytics. However, these compounds, while partially alleviating the various side effects compared with the conventional benzodiazepine-based medicaments, still cannot be said to be sufficient. Development of anxiolytics with even less side effects is desired.

Further, for cerebral infarction and other cerebrovascular diseases, the thromboxane $A_2$ synthesizing enzyme inhibitor ozagrel has been confirmed to be effective for cerebral vasospasms and cerebral ischemic disorders, but it increases the tendency for hemorrhaging, and therefore, is suited for only limited diseases.

SUMMARY OF THE INVENTION

In consideration of this situation, the problem to be solved by the present invention is to provide a medicament which can be used for the treatment of anxiety neurosis, phobias, obsessive-compulsive disorders, schizophrenia, post-cardiac trauma stress disorders, depression disorders, psychosomatic disorders, and other psychoneurotic disorders, eating disorders, menopausal disorders, infantile autism and other disorders and also emesis, or disorders involving.the cerebral circulatory system accompanying cerebral infarction and cerebral hemorrhage more effectively and with fewer side effects.

The present inventors engaged in repeated intensive studies to develop a superior medicament free from the above problems and, as a result, found that the compounds of the present invention, that is, the novel benzoxazepine derivatives and their salts, have beneficial pharmacological effects, that is, the compounds of the present invention have an anxiolytic activity, an activity suppressing cerebral infarction, and other protective effects-on the brain in ischemic brain diseases.

It is known that when there is nonselective affinity with serotonin receptors and affinity with dopamine $D_2$ receptors in the central nervous system, there is a possibility of extrapyramidal syndromes and other side. effects occurring, which is not desirable. The present inventors previously found that certain types of benzoxazepine derivatives exhibited an anticonflict activity (see Japanese Unexamined Patent Publication (Kokai) No. 2-256671). Further, recently, the involvement of cerebral serotonergic neuron in cerebral ischemic conditions has been suggested. Among the types of serotonin receptor related activities, there have been reports that a serotonina type receptor agonist has a protective effect on the brain in cerebral ischemic conditions (G. W. Bielenberg et al., Stroke Supplement IV, vol. 21, p. 161, 1990, etc.) and that a $serotonin_2$ type receptor antagonist exhibits a protective effect in ischemic neuronal damage (Brain Res., vol. 494, no. 2, p. 387–390, 1989, etc.)

The present inventors, based on the above findings, synthesized compounds using as key indicators the affinity with a serotonergic receptor and the affinity with a dopamine $D_2$ receptor and discovered that the specific benzoxazepine derivatives and their salts of the following general formulas (I), (II), and (III) exhibit an anxiolytic activity confirmed by the anticonflict activity as an indicator and that they have suppressive activity in cerebral infarction and other protective effects of the brain in ischemic brain diseases in a transient right middle cerebral artery occlusion (MCAO) model and accordingly found that these compounds were useful as medicaments for use for the treatment of anxiety neurosis, phobias, obsessive-compulsive disorders, schizophrenia, post-cardiac trauma stress disorders, depression disorders, psychosomatic disorders, and other psychoneurotic disorders, eating disorders, menopausal disorders, infantile autism and other disorders, and also emesis, or disorders involving the cerebral circulatory system accompanying cerebral infarction and cerebral hemorrhage more effectively and with fewer side effects, whereby the present invention was completed.

Accordingly, the object of the present invention is to provide the novel benzoxazepine derivatives.

Another object of the present invention is to provide medicaments containing these benzoxazepine derivatives or their pharmaceutically acceptable salts as essential ingredients and usable for the treatment of anxiety neurosis, phobias, obsessive-compulsive disorders, schizophrenia, post-cardiac trauma stress disorders, depression-disorders, psychosomatic disorders, and other psychoneurotic disorders, eating disorders, menopausal disorders, infantile autism and other disorders, and also emesis, or disorders involving the cerebral circulatory system accompanying cerebral infarction and cerebral hemorrhage.

In accordance with the present invention, there is provided a novel benzoxazepine derivative having the general formula (I) and its salts:

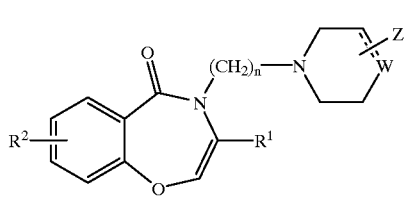

(I)

wherein, n is an integer of 2 to 5, $R^1$ indicates an hydrogen atom, halogen atom, $C_1$ to $C_4$ lower alkyl group, $C_1$ to $C_4$ lower alkoxyalkyl group, $C_1$ to $C_4$ halogenoalkyl group, cyano group, or ester group, $R^2$ indicates a hydrogen atom, halogen atom, $C_1$ to $C_4$ lower alkyl group, $C_1$ to $C_4$ lower alkoxy group, or hydroxy group, a dotted line indicates the presence or absence of a binding bond, W indicates C, CH, or $CH_2$ or a nitrogen atom, provided that, when W is a nitrogen atom, Z is bonded to W and the dotted line indicates the absence of a bond, and Z indicates an unsubstituted or substituted aromatic hydrocarbon ring group or an unsubstituted or substituted heterocyclic group selected from phenyl, naphthyl group, pyridyl group, pyrimidinyl ground, pyrazinyl group, pyridazinyl group, quinolyl group, isoquinolyl group, quinoxalinyl group, quinazolinyl group, 2-thiazolyl group, 2-oxazolyl group, 2-benzathiazolyl group, 2-thienyl group, and 3-thienyl group, and 3-thienyl group, which may be substituted with a $C_1$ to $C_4$ lower alkyl group, $C_1$ to $C_4$ lower alkoxy group, hydroxy group, amino group, and/or halogen atom.

In accordance with the present invention, there is also provided a novel benzoxazepine derivative having the general formula (II) and its salts:

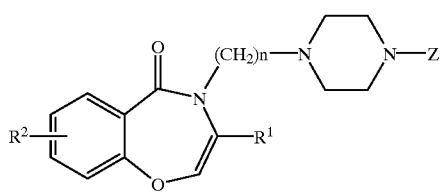

(II)

wherein, n, $R^1$, $R^2$, and Z are the same as defined above.

In accordance with the present invention, there is further provided a novel benzoxazepine derivative having the general formula (III) and its salts:

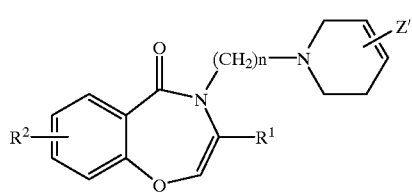

(III)

wherein, n, $R^1$, and $R^2$ are the same as defined above, a dotted line indicates the presence or absence of a combining bond, and Z' indicates an unsubstituted or substituted heteroaromatic group.

In accordance with the present invention, there is still further provided a novel benzoxazepine derivative and its salts wherein, in the general formula (III), the group Z' indicates the following general formula (IV):

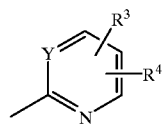

(IV)

wherein, Y indicates CH, or a nitrogen atom, $R^3$ and $R^4$ respectively indicate a hydrogen atom, halogen atom, $C_1$ to $C_4$ lower alkyl group, or hydroxy group).

In accordance with the present invention, there is still further provided a benzoxazepine derivative having the general formula (V) and its salts:

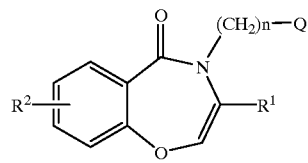

(V)

wherein, n, $R^1$, and $R^2$ are the same as defined above, and Q indicates a leaving group which may be replaced with hydroxy group, alkoxy group, halogen or amino group which are useful as synthetic intermediates for the benzoxazepine derivatives and salts having formulae (I), (II), and (III).

In accordance with the present invention, there is still further provided a benzoxazepine derivative having the general formula (VI) and its salts:

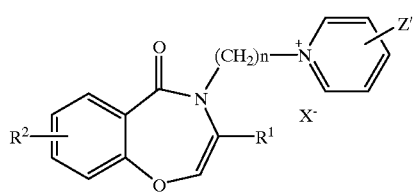

(VI)

wherein, n, $R^1$, $R^2$, and Z' are the same as defined above, and X indicates a halogen atom which are useful as synthetic intermediates for the benzoxazepine derivatives and salts having formulae (I) and (III).

In accordance with the present invention, there is still further provided a novel pyrimidine derivative having the general formula (VII) and its salts:

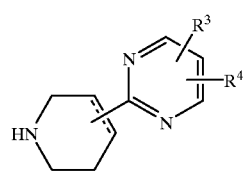

(VII)

wherein, $R^3$ and $R^4$ are the same as defined above, and a dotted line indicates the presence or absence of a binding bond which are useful as synthetic intermediates for the benzoxazepine derivatives and salts having the general formulas (I) and (III).

BEST MODE FOR CARRYING OUT THE INVENTION

The compounds having the general formulas (I), (II), and (III) provided by the present invention will now be explained in detail by Examples, but, of course, the present invention is not limited thereto.

In the compounds having the general formulae (I) and (II), preferable examples of the integer n in the formulas, are 3 to 5, in particular, 4 is preferred. Preferable examples of the group $R^1$ in the general formulae (I) and (II) are a hydrogen atom, $C_1$ to $C_3$ lower alkyl group, $C_1$ to $C_3$ lower alkoxyalkyl group, $C_1$ to $C_2$ halogenoalkyl group, chlorine atom, or nitryl group and, in particular, a hydrogen atom, methyl group, ethyl group, methoxymethyl group, chloromethyl group, or chlorine atom is more preferable; preferable examples of the group $R^2$ are a hydrogen atom, halogen atom, $C_1$ to $C_2$ lower alkyl group, $C_1$ to $C_2$ lower alkoxy group, or hydroxy group and, in particular, a hydrogen atom, fluorine atom, chlorine atom, methyl group, or methoxy group are more preferable. Further, preferable examples of the group Z are a monocyclic or polycyclic aromatic ring group or heterocyclic selected from phenyl group, naphthyl group, pyridyl group, pyrimidinyl group, pyrazinyl group, pyridazinyl group, quinolyl group, isoquinolyl group, quinoxalinyl group, quinazolinyl group, 2-thiazolyl group, 2-oxazolyl group, 2-benzothiazolyl group, 2-benzoxazolyl group, 3-isothiazolyl group, 2-thienyl group, and 3-thienyl group, which may be substituted with a $C_1$ to $C_4$ lower alkyl group, $C_1$ to $C_4$ lower alkoxy group, hydroxy group, amino group, and/or halogen atom, and in particular a group selected from a phenyl group, naphthyl group, pyridyl group, pyrimidinyl group, quinoxalinyl group, quinolyl group, isoquinolyl group, and quinazolinyl group which may be substituted with a methyl group, methoxy group, hydroxy group, amino group, chlorine atom and/or fluorine atom is preferred.

More specific preferred embodiments of the compounds having the general formulae (I) and (II) are, for example, the following compound Nos. 1 to 71, 222, and 223.

1) 4,5-dihydro-4-(4-(4-phenylpiperazin-1-yl)butyl)-1,4-benzoxazepin-5-one
2) 4,5-dihydro-4-(4-(4-(2-methoxyphenyl)piperazin-1-yl)butyl)-1,4-benzoxazepin-5-one
3) 4,5-dihydro-4-(4-(4-(6-chloropyridin-2-yl)piperazin-1-yl)butyl)-1,4-benzoxazepin-5-one
4) 4,5-dihydro-4-(4-(4-(2-pyrimidinyl)piperazin-1-yl)butyl)-1,4-benzoxazepin-5-one
5) 4,5-dihydro-4-(4-(4-(6-methoxypyrazin-2-yl)piperazin-1-yl)butyl)-1,4-benzoxazepin-5-one
6) 4,5-dihydro-4-(4-(4-(4-quinazolyl)piperazin-1-yl)butyl)-1,4-benzoxazepin-5-one
7) 4,5-dihydro-8-methoxy-4-(4-(4-(3-methylphenyl)piperazin-1-yl)butyl)-1,4-benzoxazepin-5-one
8) 4,5-dihydro-8-methoxy-4-(4-(4-(2-pyridyl)piperazin-1-yl)butyl)-1,4-benzoxazepin-5-one
9) 4,5-dihydro-8-methoxy-4-(4-(4-(2-pyrimidinyl)piperazin-1-yl)butyl)-1,4-benzoxazepin-5-one
10) 4-(4-(4-(6-amino-5-fluoropyrimidin-2-yl)piperazin-1-yl)butyl)-4,5-dihydro-8-methoxy-1,4-benzoxazepin-5-one
11) 4,5-dihydro-3-methyl-4-(4-(4-phenylpiperazin-1-yl)butyl)-1,4-benzoxazapin-5-one
12) 4,5-dihydro-3-methyl-4-(4-(4-(2-pyridyl)piperazin-1-yl)butyl)-1,4-benzoxazepin-5-one
13) 4,5-dihydro-3-methyl-4-(4-(4-(2-pyrimidinyl)piperazin-1-yl)butyl)-1,4-benzoxazepin-5-one
14) 4,5-dihydro-3,7-dimethyl-4-(4-(4-(2-methoxyphenyl)piperazin-1-yl)butyl)-1,4-benzoxazepin-5-one
15) 4,5-dihydro-3,7-dimethyl-4-(4-(4-(6-methoxypyrazin-2-yl)piperazin-1-yl)butyl)-1,4-benzoxazepin-5-one
16) 4,5-dihydro-7-methoxy-3-methyl-4-(4-(4-(3-methylphenyl)piperazin-1-yl)butyl)-1,4-benzoxazepin-5-one
17) 4,5-dihydro-7-methoxy-3-methyl-4-(4-(4-(6-chloropyridin-2-yl)piperazin-1-yl)butyl)-1,4-benzoxazepin-5-one
18) 4,5-dihydro-7-methoxy-3-methyl-4-(4-(4-(2-pyrimidinyl)piperazin-1-yl)butyl)-1,4-benzoxazepin-5-one
19) 4,5-dihydro-7-fluoro-3-methyl-4-(4-4-(2-pyridyl)piperazin-1-yl)butyl)-1,4-benzoxazepin-5-one
20) 4,5-dihydro-7-fluoro-3-methyl-4-(4-(4-(2-pyrimidinyl)piperazin-1-yl)butyl)-1,4-benzoxazepin-5-one
21) 4,5-dihydro-7-fluoro-3-methyl-4-(4-(4-(4-quinazolyl)piperazin-1-yl)butyl)-1,4-benzoxazepin-5-bne
22) 4,5-dihydro-3,8-dimethyl-4-(4-(4-phenylpiperazin-1-yl)butyl)-1,4-benzoxazepin-5-one
23) 4,5-dihydro-3,8-dimethyl-4-(4-(4-(6-chloropyridin-2-yl)piperazin-1-yl)butyl)-1,4-benzoxazepin-5-one
24) 4,5-dihydro-3,8-dimethyl-4-(4-(4-(6-methoxypyrazin-2-yl)piperazin-1-yl)butyl)-1,4-benzoxazepin-5-one
25) 4,5-dihydro-8-methoxy-3-methyl-4-(4-(4-(2-pyridyl)piperazin-1-yl)butyl)-1,4-benzoxazepin-5-one
26) 4,5-dihydro-8-methoxy-3-methyl-4-(4-(4-(2-pyrimidinyl)piperazin-1-yl)butyl)-1,4-benzoxazepin-5-one
27) 8-chloro-4,5-dihydro-3-methyl-4-(4-(4-phenylpiperazin-1-yl)butyl)-1,4-benzoxazepin-5-one
28) 8-chloro-4,5-dihydro-3-methyl-4-(4-(4-(2-pyrimidinyl)piperazin-1-yl)butyl)-1,4-benzoxazepin-5-one
29) 4-(4-(4-(6-amino-5-fluoropyrimidin-2-yl)piperazin-1-yl)butyl)-8-chloro-4,5-dihydro-3-methyl-1,4-benzoxazepin-5-one
30) 3-chloro-4,5-dihydro-4-(4-(4-(2-methoxyphenyl)piperazin-1-yl)butyl)-1,4-benzoxazepin-5-one
31) 3-chloro-4,5-dihydro-4-(4-(4-(2-pyridyl)piperazin-1-yl)butyl)-1,4-benzoxazepin-5-one
32) 3-chloro-4,5-dihydro-4-(4-(4-(6-chloropyridin-2-yl)piperazin-1-yl)butyl)-1,4-benzoxazepin-5-one
33) 3-chloro-4,5-dihydro-4-(4-(4-(2-pyrimidinyl)piperazin-1-yl)butyl)-1,4-benzoxazepin-5-one
34) 3-chloro-4,5-dihydro-7-methyl-4-(4-(4-(2-methoxyphenyl)piperazin-1-yl)butyl)-1,4-benzoxazepin-5-one
35) 3-chloro-4,5-dihydro-7-methyl-4-(4-(4-(2-pyrimidinyl)piperazin-1-yl)butyl)-1,4-benzoxazepin-5-one
36) 3-chloro-4,5-dihydro-7-methyl-4-(4-(4-(6-methoxypyrazin-2-yl)piperazin-1-yl)butyl)-1,4-benzoxazepin-5-one
37) 3-chloro-4,5-dihydro-7-methoxy-4-(4-(4-(2-methoxyphenyl)piperazin-1-yl)butyl)-1,4-benzoxazepin-5-one
38) 4-(4-(4-(6-amino-5-fluoropyrimidin-2-yl)piperazin-1-yl)butyl)-3-chloro-4,5-dihydro-7-methoxy-1,4-benzoxazepin-5-one
39) 3,7-dichloro-4,5-dihydro-4-(4-(4-(3-methylphenyl)piperazin-1-yl)butyl)-1,4-benzoxazepin-5-one
40) 3,7-dichloro-4,5-dihydro-4-(4-(4-(2-pyrimidinyl)piperazin-1-yl)butyl)-1,4-benzoxazepin-5-one
41) 3,7-dichloro-4,5-dihydro-4-(4-(4-(4-quinazolyl)piperazin-1-yl)butyl)-1,4-benzoxazepin-5-one
42) 3-chloro-4,5-dihydro-8-methyl-4-(4-(4-phenylpiperazin-1-yl)butyl)-1,4-benzoxazepin-5-one 43) 3chloro-4,5-dihydro-8-methyl-4-(4-(4-(6-chloropyridin-2-yl)piperazin-1-yl)butyl)-1,4-benzoxazepin-5-one
44) 3-chloro-4,5-dihydro-8-methoxy-4-(4-(4-(2-methoxyphenyl)piperazin-1-yl)butyl)-1,4-benzoxazepin-5-one
45) 3-chloro-4,5-dihydro-8-methoxy-4-(4-(4-(2-pyridyl)piperazin-1-yl)butyl)-1,4-benzoxazepin-5-one
46) 3-chloro-4,5-dihydro-8-methoxy-4-(4-(4-(2-pyrimidinyl)piperazin-1-yl)butyl)-1,4-benzoxazepin-5-one
47) 3,8-dichloro-4,5-dihydro-4-(4-(4-(2-pyridyl)piperazin-1-yl)butyl)-1,4-benzoxazepin-5-one
48) 3,8-dichloro-4,5-dihydro-4-(4-(4-(6-chloropyridin-2-yl)piperazin-1-yl)butyl)-1,4-benzoxazepin-5-one
49) 3,8-dichloro-4,5-dihydro-4-(4-(4-(2-pyrimidinyl)piperazin-1-yl)butyl)-1,4-benzoxazepin-5-one
50) 4,5-dihydro-3-methoxymethyl-4-(4-(4-phenylpiperazin-1-yl)butyl)-1,4-benzoxazepin-5-one
51) 4,5-dihydro-3-methoxymethyl-4-(4-(4-(2-pyrixmidinyl)piperazin-1-yl)butyl)-1,4-benzoxazepin-5-one
52) 4,5-dihydro-3-methoxymethyl-7-methyl-4-(4-(4-(2-pyridyl)piperazin-1-yl)butyl)-1,4-benzoxazepin-5-one
53) 4,5-dihydro-3-methoxymethyl-7-methyl-4-(4-(4-(2-pyrimidinyl)piperazin-1-yl)butyl)-1,4-benzoxazepin-5-one
54) 4,5-dihydro-3-methoxymethyl-7-methyl-4-(4-(4-(4-quinazolyl)piperazin-1-yl)butyl)-1,4-benzoxazepin-5-one
55) 4,5-dihydro-7-methoxy-3-methoxymethyl-4-(4-(4-(2-methoxyphenyl)piperazin-1-yl)butyl)-1,4-benzoxazepin-5-one
56) 4-(4-(4-(6-amino-5-fluoropyrimidin-2-yl)piperazin-1-yl)butyl)-4,5-dihydro-7-methoxy-3-methoxymethyl-1,4-benzoxazepin-5-one
57) 7-chloro-4,5-dihydro-3-methoxymethyl-4-(4-(4-(2-pyridyl)piperazin-1-yl)butyl)-1,4-benzoxazepin-5-one
58) 7-chloro-4,5-dihydro-3-methoxymethyl-4-(4-(4-(6-chloropyridin-2-yl)piperazin-1-yl)butyl)-1,4-benzoxazepin-5-one
59) 4,5-dihydro-3-methoxymethyl-8-methyl-4-(4-(4-(6-methoxypyrazin-2-yl)piperazin-1-yl)butyl)-1,4-benzoxazepin-5-one
60) 4,5-dihydro-8-methoxy-3-methoxymethyl-4-(4-(4-(2-pyrimidinyl)piperazin-1-yl)butyl)-1,4-benzoxazepin-5-one
61) 8-chloro-4,5-dihydro-3-methoxymethyl-4-(4-(4-(3-methylphenyl)piperazin-1-yl)butyl)-1,4-benzoxazepin-5-one
62) 3-chloromethyl-4,5-dihydro-4-(4-(4-(2-methoxyphenyl)piperazin-1-yl)butyl)-1,4-benzoxazepin-5-one
63) 3-chloromethyl-4,5-dihydro-4-(4-(4-(2-pyrimidinyl)piperazin-1-yl)butyl)-1,4-benzoxazepin-5-one
64) 3-chloromethyl-4,5-dihydro-7-methyl-4-(4-(4-(2-pyridyl)piperazin-1-yl)butyl)-1,4-benzoxazepin-5-one
65) 3-chloromethyl-4,5-dihydro-7-methoxy-4-(4-(4-(6-chloropyridin-2-yl)piperazin-1-yl)butyl)-1,4-benzoxazepin-5-one
66) 3-chloromethyl-4,5-dihydro-7-methoxy-4-(4-(4-(2-pyrimidinyl)piperazin-1-yl)butyl)-1,4-benzoxazepin-5-one
67) 7-chloro-3-chloromethyl-4,5-dihydro-4-(4-(4-phenylpiperazin-1-yl)butyl)-1,4-benzoxazepin-5-one
68) 3-chloromethyl-4,5-dihydro-8-methyl-4-(4-(4-(2-pyridyl)piperazin-1-yl)butyl)-1,4-benzoxazepin-5-one
69) 4-(4-(4-(6-amino-5-fluoropyrimidin-2-yl)piperazin-1-yl)butyl)-3-chloromethyl-4,5-dihydro-8-methyl-1,4-benzoxazepin-5-one
70) 3-chloromethyl-4,5-dihydro-8-methoxy-4-(4-(4-(2-pyrimidinyl)piperazin-1-yl)butyl)-1,4-benzoxazepin-5-one
71) 8-chloro-3-chloromethyl-4,5-dihydro-4-(4-(4-(2-pyrimidinyl)piperazin-1-yl)butyl)-1,4-benzoxazepin-5-one
222) 4,5-dihydro-8-hydroxy-4-(4-(4-(2-pyridyl)piperazin-1-yl)butyl)-1,4-benzoxazepin-5-one
223) 3-chloro-8-hydroxy-4,5-dihydro-4-(4-(4-(2-pyrimidinyl)piperazin-1-yl)butyl)-1,4-benzoxazepin-5-one In the compounds having the general formulae (I) and (III), preferable examples of the integer n in the formula, are 3 to 5 and in particular, 4 is preferred. Preferable examples of the group $R^1$ in the general formulae (I) and (III) are a hydrogen atom, $C_1$ to $C_3$ lower alkyl group, $C_1$ to $C_3$ lower alkoxyalkyl group, $C_1$ to $C_2$ halogenoalkyl group, chlorine atom, or nitryl group and, in particular, a hydrogen atom, methyl group, ethyl group, methoxymethyl group, chloromethyl group, or chlorine atom is more preferred; preferable examples of the group $R^2$ are a hydrogen atom, halogen atom, $C_1$ to $C_2$ lower alkyl group, $C_1$ to $C_2$ lower alkoxy group, or hydroxy group and in particular, a hydrogen atom, fluorine atom, chlorine atom, methyl group, or methoxy group is more preferred. Further, preferable examples of the group Z' are a monocyclic or polycyclic heterocyclic group selected from pyridyl group, pyrimidinyl group, pyrazinyl group, pyridazinyl group, quinolyl group, isoquinolyl group, quinoxalinyl group, quinazolinyl group, 2-thiazolyl group, 2-oxazolyl group, 2-benzothiazolyl group, 2-benzoxazolyl group, 3-isothiazolyl group, 2-thienyl group, and 3-thienyl group, which may be substituted with a $C_1$ to $C_4$ lower alkyl group, $C_1$ to $C_4$ lower alkoxy group, hydroxy group, amino group, and/or halogen atom and, in particular a group selected from pyridyl group, pyrimidinyl group, quinoxalinyl group, quinolyl group, isoquinolyl group, and quinazolinyl group which may be substituted with a methyl group, methoxy group, hydroxy group, amino group, chlorine atom and/or fluorine atom is preferred.

More specific preferred embodiments of the compounds of the general formulae (I) and (III), are for example, the following compound Nos. 72 to 221 and 224 to 227:

72) 4,5-dihydro-4-(4-(4-(2-pyridyl)piperidin-1-yl)butyl)-1,4-benzoxazepin-5-one
73) 4,5-dihydro-4-(4-(4-(2-pyrimidinyl)piperidin-1-yl)butyl)-1,4-benzoxazepin-5-one
74) 4,5-dihydro-8-methoxy-4-(4-(4-(6-chloropyridin-2-yl)piperidin-1-yl)butyl)-1,4-benzoxazepin-5-one
75) 4-(4-(4-(6-amino-5-fluoropyrimidin-2-yl)piperidin-1-yl)butyl)-4,5-dihydro-8-methoxy-1,4-benzoxazepin-5-one
76) 4,5-dihydro-3-methyl-4-(4-(4-(2-pyrimidinyl)piperidin-1-yl)butyl)-1,4-benzoxazepin-5-one
77) 4,5-dihydro-3-methyl-4-(4-(4-(6-methoxypyrazin-2-yl)piperidin-1-yl))butyl)-1,4-benzoxazepine-5-one
78) 4,5-dihydro-3,7-dimethyl-4-(4-(4-(2-pyridyl)piperidin-1-yl)butyl)-1,4-benzoxazepin-5-one
79) 4,5-dihydro-7-methoxy-3-methyl-4-(4-(4-(2-pyridyl)piperidin-1-yl)butyl)-1,4-benzoxazepin-5-one
80) 4,5-dihydro-7-methoxy-3-methyl-4-(4-(4-(2-pyrimidinyl)piperidin-1-yl)butyl)-1,4-benzoxazepin-5-one
81) 4,5-dihydro-7-fluoro-3-methyl-4-(4-(4-(2-pyridyl)piperidin-1-yl)butyl)-1,4-benzoxazepin-5-one
82) 4,5-dihydro-7-fluoro-3-methyl-4-(4-(4-(6-chloropyridin-2-yl)piperidin-1-yl)butyl)-1,4-benzoxazepin-5-one
83) 4,5-dihydro-7-fluoro-3-methyl-4-(4-(4-(2-pyrimidinyl)piperidin-1-yl)butyl)-1,4-benzoxazepin-5-one 84) 4,5-dihydro-3,8-dimethyl-4-(4-(4-(2-pyrimidinyl)piperidin-1-yl)butyl)-1,4-benzoxazepin-5-one
85) 4-(4-(4-(6-amino-5-fluoropyrimidin-2-yl)piperidin-1-yl)butyl)-4,5-dihydro-3,8-dimethyl-1,4-benzoxazepin-5-one
86) 4,5-dihydro-8-methoxy-3-methyl-4-(4-(4-(2-pyrimidinyl)piperidin-1-yl)butyl)-1,4-benzoxazepin-5-one
87) 8-chloro-4,5-dihydro-3-methyl-4-(4-(4-(4-quinazolyl)piperidin-1-yl)butyl)-1,4-benzoxazepin-5-one
88) 3-chloro-4,5-dihydro-4-(4-(4-(2-pyridyl)piperidin-1-yl)butyl)-1,4-benzoxazepin-5-one
89) 3-chloro-4,5-dihydro-4-(4-(4-(2-pyrimidinyl)piperidin-1-yl)butyl)-1,4-benzoxazepin-5-one
90) 3-chloro-4,5-dihydro-7-methyl-4-(4-(4-(6-chloropyridin-2-yl)piperidin-1-yl)butyl)-1,4-benzoxazepin-5-one
91) 3-chloro-4,5-dihydro-7-methoxy-4-(4-(4-(6-methoxypyrazin-2-yl)piperidin-1-yl)butyl)-1,4-benzoxazepin-5-one
92) 3,7-dichloro-4,5-dihydro-4-(4-(4-(2-pyridyl)piperidin-1-yl)butyl)-1,4-benzoxazepin-5-one
93) 3-chloro-4,5-dihydro-8-methyl-4-(4-(4-(2-pyrimidinyl)piperidin-1-yl)butyl)-1,4-benzoxazepin-5-one
94) 3chloro-4,5-dihydro-8-methoxy-4-(4-(4-(6-chloropyridin-2-yl)piperidin-1-yl)butyl)-1,4-benzoxazepin-5-one
95) 3-chloro-4,5-dihydro-8-methoxy-4-(4-(2-pyrimidinyl)piperidin-1-yl)butyl)-1,4-benzoxazepin-5-one
96) 3,8-dichloro-4,5-dihydro-4-(4-(4-(2-pyrimidinyl)piperidin-1-yl)butyl)-1,4-benzoxazepin-5-one
97) 4,5-dihydro-3-methoxymethyl-4-(4-(4-(2-pyridyl)piperidin-1-yl)butyl)-1,4-benzoxazepin-5-one
98) 4,5-dihydro-3-methoxymethyl-7-methyl-4-(4-(4-(2-pyrimidinyl)piperidin-1-yl)butyl)-1,4-benzoxazepin-5-one
99) 4,5-dihydro-7-methoxy-3-methoxymethyl-4-(4-(4-(6-chloropyridin-2-yl)piperidin-1-yl)butyl)-1,4-benzoxazepin-5-one
100) 4,5-dihydro-7-methoxy-3-methoxymethyl-4-(4-(4-(4-quinazolyl)piperidin-1-yl)butyl)-1,4-benzoxazepin-5-one
101) 4-(4-(4-(6-amino-5-fluoropyrimidin-2-yl)piperidin-1-yl)butyl)-7-chloro-4,5-dihydro-3-methoxymethyl-1,4-benzoxazepin-5-one
102) 4,5-dihydro-3-methoxymethyl-8-methyl-4-(4-(4-(2-pyrimidinyl)piperidin-1-yl)butyl)-1,4-benzoxazepin-5-one
103) 4,5-dihydro-8-methoxy-3-methoxymethyl-4-(4-(4-(2-pyridyl)piperidin-1-ylbutyl)-1,4-benzoxazepin-5-one
104) 8-chloro-4,5-dihydro-3-methoxymethyl-4-(4-(4-(6-chloropyridin-2-yl)piperidin-1-yl)butyl)-1,4-benzoxazepin-5-one
105) 3-chloromethyl-4,5-dihydro-4-(4-(4-(6-methoxypyrazin-2-yl)piperidin-1-yl)butyl)-1,4-benzoxazepin-5-one
106) 3-chloromethyl-4,5-dihydro-7-methyl-4-(4-(4-(2-pyridyl)piperidin-1-yl)butyl)-1,4-benzoxazepin-5-one
107) 3-chloromethyl-4,5-dihydro-1-methoxy-4-(4-(4-(2-pyridyl)piperidin-1-yl)butyl)-1,4-benzoxazepin-5-one
108) 3-chloromethyl-4,5-dihydro-7-methoxy-4-(4-(4-(2-pyrimidinyl)piperidin-1-yl)butyl)-1,4-benzoxazepin-5-one
109) 7-chloro-3-chloromethyl-4,5-dihydro-4-(4-(4-(6-methoxypyrazin-2-yl)piperidin-1-yl)butyl)-1,4-benzoxazepin-5-one
110) 3-chloromethyl-4,5-dihydro-8-methyl-4-(4-(4-(4-quinazolyl)piperidin-1-yl)butyl)-1,4-benzoxazepin-5-one
111) 3-chloromethyl-4,5-dihydro-8-methoxy-4-(4-(4-(2-pyrimidinyl)piperidin-1yl)butyl)-1,4-benzoxazepin-5-one
112) 8-chloro-3-chloromethyl-4,5-dihydro-4-(4-(4-(2-pyrimidinyl)piperidin-1-yl)butyl)-1,4-benzoxazepin-5-one
113) 4,5-dihydro-4-(4-(4-(2-pyridyl)-1,2,5,6-tetrahydropyridin-1-yl)butyl)-1,4-benzoxazepin-5-one
114) 4,5-dihydro-4-(4-(4-(2-pyrimidinyl)-1,2,5,6-tetrahydropyridin-1-yl)butyl)-1,4-benzoxazepin-5-one
115) 4,5-dihydro-8-methoxy-4-(4-(4-(6-chloropyridin-2-yl)-1,2,5,6-tetrahydropyridin-1-yl)butyl)-1,4-benzoxazepin-5-one
116) 4,5-dihydro-8-methoxy-4-(4-(4-(2-pyrimidinyl)-1,2,5,6-tetrahydropyridin-1-yl)butyl)-1,4-benzoxazepin-5-one
117) 3-methyl-4,5-dihydro-4-(4-(4-(6-chloropyridin-2-yl)-1,2,5,6-tetrahydropyridin-1-yl)butyl)-1,4-benzoxazepin-5-one
118) 3-methyl-4,5-dihydro-4-(4-(4-(6-methoxypyrazin-2-yl)-1,2,5,6-tetrahydropyridin-1-yl)butyl)-1,4-benzoxazepin-5-one
119) 4-(4-(4-(6-amino-5-fluoropyrimidin-2-yl)-1,2,5,6-tetrahydropyridin-1-yl)butyl)-4,5-dihydro-3,7-dimethyl-1,4-benzoxazepin-5-one
120) 4,5-dihydro-7-methoxy-3-methyl-4-(4-(4-(2-pyridyl)-1,2,5,6-tetrahydropyridin-1-yl)butyl)-1,4-benzoxazepin-5-one
121) 4,5-dihydro-7-fluoro-3-methyl-4-(4-(4-(2-pyridyl)-1,2,5,6-tetrahydropyridin-1-yl)butyl)-1,4-benzoxazepin-5-one
122) 4,5-dihydro-7-fluoro-3-methyl-4-(4-(4-(2-pyrimidinyl)-1,2,5,6-tetrahydropyridin-1-yl)butyl)-1,4-benzoxazepin-5-one
123) 4,5-dihydro-3,8-dimethyl-4-(4-(4-(6-chloropyridin-2-yl)-1,2,5,6-tetrahydropyridin-1-yl)butyl)-1,4-benzoxazepin-5-one
124) 4,5-dihydro-8-methoxy-3-methyl-4-(4-(4-(2-pyrimidinyl)-1,2,5,6-tetrahydropyridin-1-yl)butyl)-1,4-benzoxazepin-5-one
125) 4,5-dihydro-8-methoxy-3-methyl-4-(4-(4-(4-quinazolyl)-1,2,5,6-tetrahydropyridin-1-yl)butyl)-1,4-benzoxazepin-5-one
126) 8-chloro-4,5-dihydro-3-methyl-4-(4-(4-(2-pyridyl)-1,2,5,6-tetrahydropyridin-1-yl)butyl)-1,4-benzoxazepin-5-one
127) 3-chloro-4,5-dihydro-4-(4-(4-(2-pyridyl)-1,2,5,6-tetrahydropyridin-1-yl)butyl)-1,4-benzoxazepin-5-one
128) 3-chloro-4,5-dihydro-4-(4-(4-(6-chloropyridin-2-yl)-1,2,5,6-tetrahydropyridin-1-yl)butyl)-1,4-benzoxazepin-5-one
129) 3-chloro-4,5-dihydro-4-(4-(4-(2-pyrimidinyl)-1,2,5,6-tetrahydropyridin-1-yl)butyl)-1,4-benzoxazepin-5-one
130) 3-chloro-4,5-dihydro-4-(4-(4-(6-methoxypyrazin-2-yl)-1,2,5,6-tetrahydropyridin-1-yl)butyl)-1,4-benzoxazepin-5-one
131) 3-chloro-4,5-dihydro-7-methyl-4-(4-(4-(6-chloropyridin-2-yl)-1,2,5,6-tetrahydropyridin-1-yl)butyl)-1,4-benzoxazepin-5-one
132) 3-chloro-4,5-dihydro-7-methoxy-4-(4-(4-(2-pyridyl)-1,2,5,6-tetrahydropyridin-1-yl)butyl)-1,4-benzoxazepin-5-one
133) 3-chloro-4,5-dihydro-7-methoxy-4-(4-(4-(2-pyrimidinyl)-1,2,5,6-tetrahydropyridin-1-yl)butyl)-1,4-benzoxazepin-5-one
134) 3,7-dichloro-4,5-dihydro-4-(4-(4-(2-pyrimidinyl)-1,2,5,6-tetrahydropyridin-1-yl)butyl)-1,4-benzoxazepin-5-one 135) 3-chloro-4,5-dihydro-8-methyl-4-(4-(4-(2-pyrimidinyl)-1,2,5,6-tetrahydropyridin-1-yl)butyl)-1,4-benzoxazepin-5-one
136) 3-chloro-4,5-dihydro-8-methoxy-4-(4-(4-(2-pyridyl)-1,2,5,6-tetrahydropyridin-1-yl)butyl)-1,4-benzoxazepin-5-one
137) 3-chloro-4,5-dihydro-8-methoxy-4-(4-(4-(6-chloropyridin-2-yl)-1,2,5,6-tetrahydropyridin-1-yl)butyl)-1,4-benzoxazepin-5-one
138) 3-chloro-4,5-dihydro-8-methoxy-4-(4-(4-(2-pyrimidinyl)-1,2,5,6-tetrahydropyridin-1-yl)butyl)-1,4-benzoxazepin-5-one
139) 3,8-dichloro-4,5-dihydro-4-(4-(4-(2-pyridyl)-1,2,5,6-tetrahydropyridin-1-yl)butyl)-1,4-benzoxazepin-5-one
140) 3,8-dichloro-4,5-dihydro-4-(4-(4-(-2-pyrimidinyl)-1,2,5,6-tetrahydropyridin-1-yl)butyl)-1,4-benzoxazepin-5-one
141) 4,5-dihydro-3-methoxymethyl-4-(4-(4-(6-chloropyridin-2-yl)-1,2,5,6-tetrahydropyridin-1-yl)butyl)-1,4-benzoxazepin-5-one
142) 4,5-dihydro-3-methoxymethyl-7-methyl-4-(4-(4-(2-pyrimidinyl)-1,2,5,6-tetrahydropyridin-1-yl)butyl)-1,4-benzoxazepin-5-one
143) 4,5-dihydro-7-methoxy-3-methoxymethyl-4-(4-(4-(6-methoxypyrazin-2-yl)-1,2,5,6-tetrahydropyridin-1-yl)butyl)-1,4-benzoxazepin-5-one
144) 7-chloro-4,5-dihydro-3-methoxymethyl-4-(4-(4-(4-quinazolyl)-1,2,5,6-tetrahydropyridin-1-yl)butyl)-1,4-benzoxazepin-5-one
145) 4,5-dihydro-3-methoxymethyl-8-methyl-4-(4-(4-(2-pyridyl)-1,2,5,6-tetrahydropyridin-1-yl)butyl)-1,4-benzoxazepin-5-one
146) 4,5-dihydro-8-methoxy-3-methoxymethyl-4-(4-(4-(2-pyrimidinyl)-1,2,5,6-tetrahydropyridin-1-yl)butyl)-1,4-benzoxazepin-5-one
147) 8-chloro-4,5-dihydro-3-methoxymethyl-4-(4-(4-(6-chloropyridin-2-yl)-1,2,5,6-tetrahydropyridin-1-yl)butyl)-1,4-benzoxazepin-5-one
148) 3-chloromethyl-4,5-dihydro-4-(4-(4-(2-pyrimidinyl)-1,2,5,6-tetrahydropyridin-1-yl)butyl)-1,4-benzoxazepin-5-one
149) 3-chloromethyl-4,5-dihydro-7-methyl-4-(4-(4-(2-pyridyl)-1,2,5,6-tetrahydropyridin-1-yl)butyl)-1,4-benzoxazepin-5-one
150) 3-chloromethyl-4,5-dihydro-7-methoxy-4-(4-(4-(2-pyridyl)-1,2,5,6-tetrahydropyridin-1-yl)butyl)-1,4-benzoxazepin-5-one
151) 7-chloro-3-chloromethyl-4,5-dihydro-4-(4-(4-(2-pyrimidinyl)-1,2,5,6-tetrahydropyridin-1-yl)butyl)-1,4-benzoxazepin-5-one
152) 3-chloromethyl-4,5-dihydro-8-methyl-4-(4-(4-(2-pyrimidinyl)-1,2,5,6-tetrahydropyridin-1-yl)butyl)-1,4-benzoxazepin-5-one
153) 3-chloromethyl-4,5-dihydro-8-methoxy-4-(4-(4-(6-methoxypyrazin-2-yl)-1,2,5,6-tetrahydropyridin-1-yl)butyl)-1,4-benzoxazepin-5-one
154) 4-(4-(4-(6-amino-5-fluoropyrimidin-2-yl)-1,2,5,6-tetrahydropyridin-1-yl)butyl)-8-chloro-3-chloromethyl-4,5-dihydro-1,4-benzoxazepin-5-one
155) 4,5-dihydro-4-(4-(3-(2-pyridyl)piperidin-1-yl)butyl)-1,4-benzoxazepin-5-one
156) 4,5-dihydro-4-(4-(3-(2-pyrimidinyl)piperidin-1-yl)butyl)-1,4-benzoxazepin-5-one
157) 4,5-dihydro-8-methoxy-4-(4-(3-(2-pyrimidinyl)piperidin-1-yl)butyl)-1,4-benzoxazepin-5-one
158) 4,5-dihydro-3-methyl-4-(4-(3-(6-chloropyridin-2-yl)piperidin-1-yl)butyl)-1,4-benzoxazepin-5-one
159) 4,5-dihydro-3,7-dimethyl-4-(4-(3-(2-pyrimidinyl)piperidin-1-yl)butyl)-1,4-benzoxazepin-5-one
160) 4,5-dihydro-7-methoxy-3-methyl-4-(4(3-(2-pyridyl)piperidin-1-yl)butyl)-1,4-benzoxazepin-5-one
161) 4,5-dihydro-7-fluoro-3-methyl-4-(4-(3-(2-pyrimidinyl)piperidin-1-yl)butyl)-1,4-benzoxazepin-5-one
162) 4,5-dihydro-7-fluoro-3-methyl-4-(4-(3-(6-methoxypyrazin-2-yl)piperidin-1-yl)butyl) -1,4-benzoxazepin-5-one
163) 4,5-dihydro-3,8-dimethyl-4-(4-(3-(2-pyrimidinyl)piperidin-1-yl)butyl)-1,4-benzoxazepin-5-one
164) 4,5-dihydro-8-methoxy-3-methyl-4-(4-(3-(4-quinazolyl)piperidin-1-yl) butyl)-1,4-benzoxazepin-5-one
165) 4-(4-(3-(6-amino-5-fluoropyrimidin-2-yl)piperidin-1-yl)butyl)-8-chloro-4,5-dihydro-3-methyl-1,4-benzoxazepin-5-one
166) 3-chloro-4,5-dihydro-4-(4-(3-(2-pyridyl)piperidin-1-yl)butyl)-1,4-benzoxazepin-5-one
167) 3-chloro-4,5-dihydro-4-(4-(3-(2-pyrimidinyl)piperidin-1-yl)butyl)-1,4-benzoxazepin-5-one
168) 3-chloro-4,5-dihydro-7-methyl-4-(4-(3-(6-chloropyridin-2-yl)piperidin-1-yl)butyl)-1,4-benzoxazepin-5-one
169) 3-chloro-4,5-dihydro-7-methyl-4-(4-(3-(2-pyrimidinyl)piperidin-1-yl)butyl)-1,4-benzoxazepin-5-one
170) 3-chloro-4,5-dihydro-7-methoxy-4-(4-(3-(2-pyrimidinyl)piperidin-1-yl)butyl)-1,4-benzoxazepin-5-one
171) 3,7-dichloro-4,5-dihydro-4-(4-(3-(2-pyridyl)piperidin-1-yl)butyl)-1,4-benzoxazepin-5-one
172) 3-chloro-4,5-dihydro-8-methyl-4-(4-(3-(2-pyrimidinyl)piperidin-1-yl)butyl)-1,4-benzoxazepin-5-one
173) 3-chloro-4,5-dihydro-8-methoxy-4-(4-(3-(6-chloropyridin-2-yl)piperidin-1-yl)butyl)-1,4-benzoxazepin-5-one
174) 3,8-dichloro-4,5-dihydro-4-(4-(3-(2-pyridyl)piperidin-1-yl)butyl)-1,4-benzoxazepin-5-one
175) 4,5-dihydro-7-methoxy-3-methoxymethyl-4-(4-(3-(2-pyrimidinyl)piperidin-1-yl)butyl)-1,4-benzoxazepin-5-one
176) 4,5-dihydro-3-methoxymethyl-8-methyl-4-(4-(3-(6-chloropyridin-2-yl)piperidin-1-yl)butyl)-1,4-benzoxazepin-5-one
177) 8-chloro-4,5-dihydro-3-methoxymethyl-4-(4-(3-(2-pyridyl)piperidin-1-yl)butyl)-1,4-benzoxazepin-5-one
178) 8-chloro-4,5-dihydro-3-methoxymethyl-4-(4-(3-(6-methoxypyrazin-2-yl)piperidin-1-yl)butyl)-1,4-benzoxazepin-5-one
179) 3-chloromethyl-4,5-dihydro-4-(4-(3-(2-pyrimidinyl)piperidin-1-yl)butyl)-1,4-benzoxazepin-5-one
180) 3-chloromethyl-4,5-dihydro-7-methoxy-4-(4-(3-(6-chloropyridin-2-yl)piperidin-1-yl)butyl)-1,4-benzoxazepin-5-one
181) 3-chloromethyl-4,5-dihydro-7-methoxy-4-(4-(3-(4-quinazolyl)piperidin-1-yl)butyl)-1,4-benzoxazepin-5-one
182) 7-chloro-3-chloromethyl-4,5-dihydro-4-(4-(3-(2-pyrimidinyl)piperidin-1-yl)butyl)-1,4-benzoxazepin-5-one
183) 3-chloromethyl-4,5-dihydro-8-methyl-4-(4-(3-(2-pyridyl)piperidin-1-yl)butyl)-1,4-benzoxazepin-5-one
184) 4-(4-(3-(6-amino-5-fluoropyrimidin-2-yl)piperidin-1-yl)butyl)-3-chloromethyl-4,5-dihydro-8-methoxy-1,4-benzoxazepin-5-one
185) 8-chloro-3-chloromethyl-4,5-dihydro-4-(4-(3-(2-pyrimidinyl)piperidin-1-yl)butyl)-1,4-benzoxazepin-5-one 186) 4,5-dihydro-4-(4-(3-(2-pyrimidinyl)-1,2,5,6-tetrahydropyridin-1-yl)butyl)-1,4-benzoxazepin-5-one
187) 4,5-dihydro-8-methoxy-4-(4-(3-(2-pyridyl)-1,2,5,6-tetrahydropyridin-1-yl)butyl)-1,4-benzoxazepin-5-one
188) 4,5-dihydro-8-methoxy-4-(4-(3-(2-pyrimidinyl)-1,2,5,6-tetrahydropyridin-1-yl)butyl)-1,4-benzoxazepin-5-one
189) 4,5-dihydro-3-methyl-4-(4-(3-(2-pyrimidinyl)-1,2,5,6-tetrahydropyridin-1-yl)butyl)-1,4-benzoxazepin-5-one
190) 4,5-dihydro-3,7-dimethyl-4-(4-(3-(2-pyridyl)-1,2,5,6-tetrahydropyridin-1-yl)butyl)-1,4-benzoxazepin-5-one
191) 4,5-dihydro-3,7-dimethyl-4-(4-(3-(6-methoxypyrazin-2-yl)-1,2,5,6-tetrahydropyridin-1-yl)butyl)-1,4-benzoxazepin-5-one
192) 4,5-dihydro-7-methoxy-3-methyl-4-(4-(3-(2-pyridyl)-1,2,5,6-tetrahydropyridin-1-yl)butyl)-1,4-benzoxazepin-5-one
193) 4,5-dihydro-7-methoxy-3-methyl-4-(4-(3-(4-quinazolyl)-1,2,5,6-tetrahydropyridin-1-yl)butyl)-1,4-benzoxazepin-5-one
194) 4,5-dihydro-7-fluoro-3-methyl-4-(4-(3-(2-pyrimidinyl)-1,2,5,6-tetrahydropyridin-1-yl)butyl)-1,4-benzoxazepin-5-one
195) 4-(4-(3-(6-amino-5-fluoropyrimidin-2-yl)-1,2,5,6-tetrahydropyridin-1-yl)butyl)-4,5-dihydro-7-fluoro-3-methyl-1,4-benzoxazepin-5-one
196) 4,5-dihydro-3,8-dimethyl-4-(4-(3-(2-pyrimidinyl)-1,2,5,6-tetrahydropyridin-1-yl)butyl)-1,4-benzoxazepin-5-one
197) 4,5-dihydro-8-methoxy-3-methyl-4-(4-(3-(2-pyrimidinyl)-1,2,5,6-tetrahydropyridin-1-yl)butyl)-1,4-benzoxazepin-5-one
198) 8-chloro-4,5-dihydro-3-methyl-4-(4-(3-(2-pyridyl)-1,2,5,6-tetrahydropyridin-1-yl)butyl)-1,4-benzoxazepin-5-one
199) 3-chloro-4,5-dihydro-4-(4-(3-(2-pyridyl)-1,2,5,6-tetrahydropyridin-1-yl)butyl)-1,4-benzoxazepin-5-one
200) 3-chloro-4,5-dihydro-4-(4-(3-(2-pyrimidinyl)-1,2,5,6-tetrahydropyridin-1-yl)butyl)-1,4-benzoxazepin-5-one
201) 3-chloro-4,5-dihydro-7-methyl-4-(4-(3-(2-pyridyl)-1,2,5,6-tetrahydropyridin-1-yl)butyl)-1,4-benzoxazepin-5-one
202) 3-chloro-4,5-dihydro-7-methyl-4-(4-(3-(6-methoxypyrazin-2-yl)-1,2,5,6-tetrahydropyridin-1-yl)butyl)-1,4-benzoxazepin-5-one
203) 3-chloro-4,5-dihydro-7-methoxy-4-(4-(3-(2-pyrimidinyl)-1,2,5,6-tetrahydropyridin-1-yl)butyl)-1,4-benzoxazepin-5-one
204) 3,7-dichloro-4,5-dihydro-4-(4-(3-(2-pyridyl)-1,2,5,6-tetrahydropyridin-1-yl)butyl)-1,4-benzoxazepin-5-one
205) 3-chloro-4,5-dihydro-8-methyl-4-(4-(3-(2-pyrimidinyl)-1,2,5,6-tetrahydropyridin-1-yl)butyl)-1,4-benzoxazepin-5-one
206) 3-chloro-4,5-dihydro-8-methoxy-4-(4-(3-(2-pyrimidinyl)-1,2,5,6-tetrahydropyridin-1-yl)butyl)-1,4-benzoxazepin-5-one
207) 3,8-dichloro-4,5-dihydro-4-(4-(3-(2-pyrimidinyl)-1,2,5,6-tetrahydropyridin-1-yl)butyl)-1,4-benzoxazepin-5-one
208) 4,5-dihydro-3-methoxymethyl-7-methyl-4-(4-(3-(2-pyrimidinyl)-1,2,5,6-tetrahydropyridin-1-yl)butyl)-1,4-benzoxazepin-5-one
209) 4,5-dihydro-7-methoxy-3-methoxymethyl-4-(4-(3-(2-pyridyl)-1,2,5,6-tetrahydropyridin-1-yl)butyl)-1,4-benzoxazepin-5-one
210) 7-chloro-4,5-dihydro-3-methoxymethyl-4-(4-(3-(6-methoxypyrazin-2-yl)-1,2,5,6-tetrahydropyridin-1-yl)butyl)-1,4-benzoxazepin-5-one
211) 4,5-dihydro-3-methoxymethyl-8-methyl-4-(4-(3-(2-pyridyl)-1,2,5,6-tetrahydropyridin-1-yl)butyl)-1,4-benzoxazepin-5-one
212) 4,5-dihydro-3-methoxymethyl-8-methyl-4-(4-(3-(4-quinazolyl)-1,2,5,6-tetrahydropyridin-1-yl)butyl)-1,4-benzoxazepin-5-one
213) 4,5-dihydro-8-methoxy-3-methoxymethyl-4-(4-(3-(2-pyrimidinyl)-1,2,5,6-tetrahydropyridin-1-yl)butyl)-1,4-benzoxazepin-5-one
214) 4-(4-(3-(6-amino-5-fluoropyrimidin-2-yl)-1,2,5,6-tetrahydropyridin-1-yl)butyl)-8-chloro-4,5-dihydro-3-methoxymethyl-1,4-benzoxazepin-5-one
215) 3-chloromethyl-4,5-dehydro-4-(4-(3-(2-pyrimidinyl)-1,2,5,6-tetrahydropyridin-1-yl)butyl)-1,4-benzoxazepin-5-one
216) 3-chloromethyl-4,5-dihydro-7-methoxy-4-(4-(3-(2-pyridyl)-1,2,5,6-tetrahydropyridin-1-yl)butyl)-1,4-benzoxazepin-5-one
217) 7-chloro-3-chloromethyl-4,5-dihydro-4-(4-(3-(2-pyrimidinyl)-1,2,5,6-tetrahydropyridin-1-yl)butyl)-1,4-benzoxazepin-5-one
218) 3-chloromethyl-4,5-dihydro-8-methyl-4-(4-(3-(2-pyrimidinyl)-1,2,5,6-tetrahydropyridin-1-yl)butyl)-1,4-benzoxazepin-5-one
219) 3-chloromethyl-4,5-dihydro-8-methoxy-4-(4-(3-(2-pyrimidinyl)-1,2,5,6-tetrahydropyridin-1-yl)butyl)-1,4-benzoxazepin-5-one
220) 8-chloro-3-chloromethyl-4,5-dihydro-4-(4-(3-(2-pyridyl)-1,2,5,6-tetrahydropyridin-1-yl)butyl)-1,4-benzoxazepin-5-one
221) 8-chloro-3-chloromethyl-4,5-dihydro-4-(4-(3-(2-pyrimidinyl)-1,2,5,6-tetrahydropyridin-1-yl)butyl)-1,4-benzoxazepin-5-one
224) 4,5-dihydro-7-hydroxy-3-methyl-4-(4-(4-(2-pyrimidinyl)-1,2,5,6-tetrahydropyridin-1-yl)butyl)-1,4-benzoxazepin-5-one
225) 3-chloro-7-hydroxy-4,5-dihydro-4-(4-(4-(2-pyridyl)-1,2,5,6-tetrahydropyridin-1-yl)butyl)-1,4-benzoxazepin-5-one
226) 3-chloro-4,5-dihydro-4-(4-(4-(5-hydroxypyrimidin-2-yl)-1,2,5,6-tetrahydropyridin-1-yl)butyl)-1,4-benzoxazepin-5-one
227) 3-chloro-4,5-dihydro-4-(4-(4-(4,6-dihydroxypyrimidin-2-yl)-1,2,5,6-tetrahydropyridin-1-yl)butyl)-1,4-benzoxazepin-5-one The compounds having the general formula (I), (II), or (III) provided by the present invention may for example be produced in the following way:

The compounds having the general formula (I) may be synthesized by condensation reaction, by an ordinary method, of the intermediate having the general formula (V) and the intermediate having the general formula (VIII):

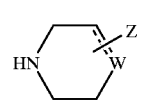

(VIII)

wherein, W and Z are the same as defined above.

In the intermediate having the general formula (V) provided by the present invention, preferable examples of the integer n in the formula, are 3 to 5 and, in particular, 4 is preferred; as preferable examples of the group $R^1$ in the formula, a hydrogen atom, $C_1$ to $C_3$ lower alkyl group, $C_1$ to $C_3$ alkoxyalkyl group, $C_1$ to $C_2$ halogenoalkyl group, chlorine atom, or nitryl group and, in particular a hydrogen atom, methyl group, ethyl group, methoxymethyl group, chloromethyl group, or chlorine atom is more preferred; preferable examples of the group $R^2$ are a hydrogen atom, halogen atom, $C_1$ to $C_2$ lower alkyl, group, $C_1$ to $C_2$ lower alkoxy group, or hydroxy group and, in particular a hydrogen atom, fluorine atom, chlorine atom, methyl group, or methoxy group is more preferred. Further, preferable examples of the leaving group shown by the group Q which may be replaced with hydroxy group, an alkoxy group, halogen or amino group is, a tosyl group, mesyl group, chlorine atom, bromine atom, or iodine atom, and, in particular a chlorine atom, bromine atom, or iodine atom is more preferred.

The method of synthesis of the final compound (I) may be explained by the method of synthesis of the compound of the general formula (II) and the method of synthesis of the compound of the general formula (III).

1) Synthesis of Final Compound having Formula (II)

The compound having the general formula (II) may be produced by condensation reaction, by an ordinary method, between a benzoxazepine derivative having the general formula (V) and a piperazine derivative having the general formula (IX):

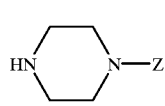

(IX)

wherein, Z is the same as defined above.

Here, the useful synthetic intermediate having the general formula (V) may be produced as follows. For example, a compound having the general formula (Va):

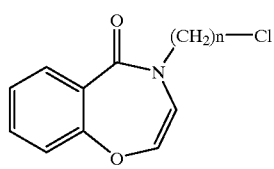

(Va)

wherein, n is the same as defined above, wherein in the compound having the general formula (V), $R^1$ and $R^2$ indicate a hydrogen atom and Q indicates a chlorine atom may be obtained as follows. A compound having the following general formula (X)

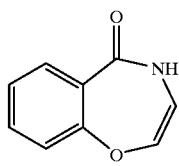

(X)

obtained by the method described in H, Hofmann et al. (Liebigs Ann.Chem., p. 917, 1990) or a method similar to the same is allowed to react with, for example bromochloroalkane to obtain the useful synthetic intermediate having the benzoxazepine derivative (Va).

Further a compound having the general formula (Vb):

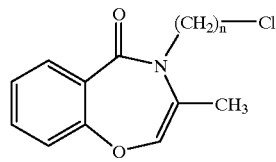

(Vb)

wherein, n is the same as defined above, wherein the compound having the above general formula (V), for example, $R^1$ indicates a methyl group, $R^2$ indicates a hydrogen atom, and Q indicates a chlorine atom can be obtained as follows. A compound having the general formula (XI)

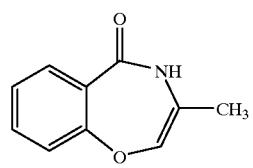

(XI)

obtained according to a method described in the reference of J. Freedmann et al. (J. Heterocyclic Chem., vol. 27, p. 343, 1990) or a similar method is allowed to react with, for example, bromochloroalkane, to obtain the useful synthetic intermediate of the benzoxazepine derivative (Vb).

Further a compound of the general formula (Vc):,

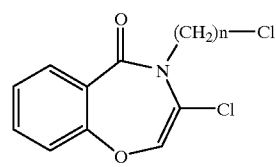

(Vc)

(wherein, n indicates the same as the above) wherein in the compound of the above general formula (V), for example, $R^1$ indicates a halogen atom, for example, a chlorine atom, $R^2$ indicates a hydrogen atom, and Q is a chlorine atom can be obtained as follows: A compound of the general formula (XII)

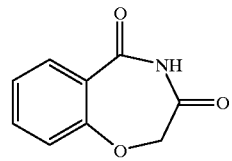

(XII)

obtained in accordance with the method described in the reference of A. Cattaneo et al. (Boll. Chim. Farm., vol. 102, p. 541, 1963) or a similar method is caused to react with, for example, bromochloroalkane to obtain a compound having the general formula (XIII):

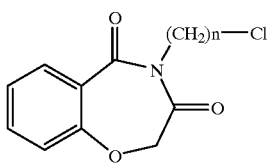

(XIII)

wherein, n is the same as defined above, then if necessary, a reaction is caused with phosphorus oxychloride or thionyl chloride or another acid chloride while adding hydrochloric acid or another acid or N,N-diethylaniline or another base to thereby obtain the useful synthetic intermediate of the benzoxazepine derivative (Vc).

The benzoxazepine derivative (Vc) may be further synthesized by the following other method. That is, it may be obtained by reacting a compound having the general formula (XII) with phosphorus oxychloride or thionyl chloride or another acid chloride, while adding, if necessary, hydrochloric acid or another acid or N,N-diethylaniline or another base to convert it to the compound having the general formula (XIV):

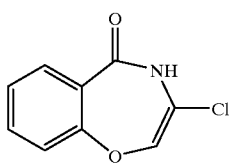

(XIV)

and then reacting with, for example, bromochloroalkane.

Further, a compound having the general formula (Vd):

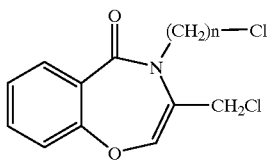

(Vd)

wherein, n is the same as defined above, where, in the compound having the above general formula (V), for example, $R^1$ indicates a halomethyl group, for example, a chloromethyl group, $R^2$ indicates a hydrogen atom, and Q is a chlorine atom can be obtained as follows:

A compound having the intermediate (Vb) is reacted with N-chlorosuccinimide to obtain the useful synthetic intermediate of the benzoxazepine derivative (Vd).

Further, the compound having the general formula (Ve):

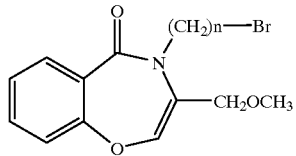

(Ve)

wherein, n is the same as defined above, where, in the compound having the above general formula (V), $R^1$ indicates a $C_1$ to $C_4$ lower alkoxymethyl group, for example, a methoxymethyl group, $R^2$ indicates a hydrogen atom, and Q is a bromine atom may be obtained as follows:

The compound of the above intermediate (XI) is reacted with N-chlorosuccinimide to convert it to the compound (XV) of the following structure:

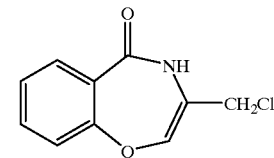

(XV)

Next, sodium methoxide is used to convert this compound to the compound of the following compound (XVI):

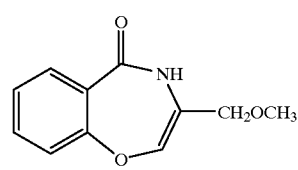

(XVI)

which is then reacted with dibromoalkane to thereby obtain the useful synthetic intermediate of the benzoxazepine derivative (Ve).

A compound having the general formula (Vf):

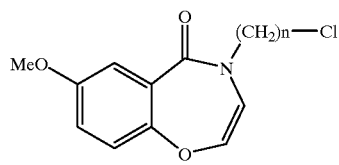

(Vf)

wherein, n is the same as defined above, wherein in the compound having the general formula (V), for example, $R^1$ indicates a hydrogen atom, $R^2$ indicates an alkoxy group, for example, 7-methoxy, and Q is a chlorine atom can be obtained by obtaining the compound of the general formula (XVII):

(XVII)

according to the method described in the reference of the above H. Hofmann et al. or a similar method, then performing the same procedure as with the procedure for synthesizing the compound having the general formula (Va).

A compound having the general formula (Vg):

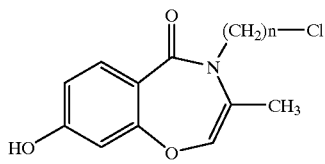
(Vg)

wherein, n is the same as defined above, where, in the compound having the general formula (V), for example, $R^1$ indicates an alkyl group, for example, a methyl group, $R^2$ indicates a 8-hydroxy group, and Q is a chlorine atom can be obtained by obtaining a compound having the general formula (XVIII):

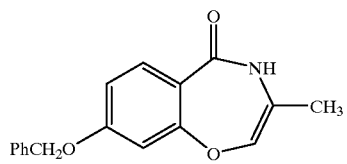
(XVIII)

according to the method described in the reference of the above J. Freedmann et al. or a similar method, then performing the same procedure as with the procedure for synthesizing the compound of the general formula (Vb) to obtain a compound having the general formula (XIX):

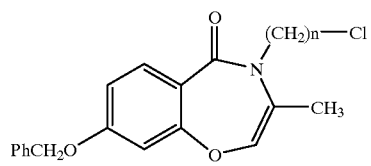
(XIX)

wherein n is the same as defined above and then eliminating the benzyl group by a catalytic reduction.

The compound of the general formula (Vh):

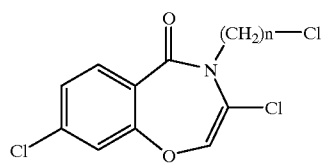
(Vh)

wherein n is the same as defined above, wherein, in the compound having the general formula (V), for example, R and Q indicate a halogen atom, for example, a chlorine atom, and $R^2$ is an 8-chloro atom can be obtained by obtaining the compound having the general formula (XX):

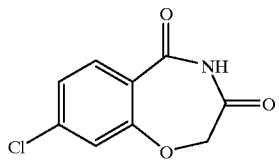
(XX)

according to the method described in the reference of A. Cattaneo et al. or a similar method, then performing the same procedure as with the procedure for synthesizing the compound having the general formula (Vc).

The compound having the general formula (Vi):

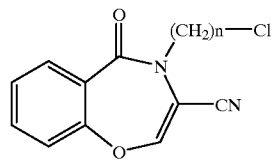
(Vi)

wherein, n is the same as defined above, where, in the compound having the general formula (V), for example, $R^1$ indicates a nitryl group, $R^2$ indicates a hydrogen atom, and Q is a chlorine atom can be obtained by causing trimethylsilylnitrile to act on the compound having the general formula (XIII) if necessary in the presence of zinc iodide or causing trimethylsilylnitrile to act on the compound having the general formula (Vc) in the, presence of a palladium catalyst.

The compound having the general formula (Vj):

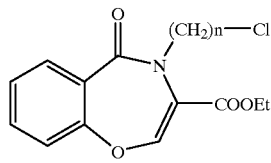
(Vj)

wherein, n is the same as defined above, where, in the compound having the general formula (V), for example, $R^1$ indicates an ester group, for example, an ethyl ester, $R^2$ indicates a hydrogen atom, and Q is a chlorine atom can be obtained by causing ethanol to act on the compound of the general formula (Vi) in the presence of an acid catalyst.

The compound having the final compound (II) can be produced by a substitution condensation of known piperazine derivatives with the synthetic intermediates illustrated in the above (Va) to (Vj) using if necessary triethylamine or another base or sodium iodide or another catalyst.

2) Synthesis of Final Compound having Formula (III)

The compound having the general formula (III) can be synthesized by a condensation reaction by an ordinary method, of the benzoxazepine derivative having the general formula (V) and the intermediate compound having the formula (XXI):

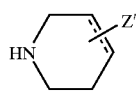

(XXI)

wherein Z' is the same as defined above.

Here, the intermediate having the general formula (V) may be synthesized by the same technique as for the synthesis of the compounds having, for example, the above mentioned general formulae (Va) to (Vj).

The other synthetic intermediates of the compound having the general formula (XXI) can be synthesized in the following way. Among the compounds (XXI), the pyrimidine derivative having the general formula (VII), for example, can be obtained in the following manner. The pyrimidine derivatives (VIIa)

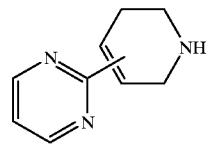

(VIIa)

where, in the general formula (VII), for example, $R^3$ and $R^4$ respectively indicate a hydrogen atom, a dotted line indicates the presence of a combining bond, and the 2-pyrimidinyl group is bonded to the 3-position or 4-position of the 1,2,5,6-tetrahydropyridyl group is obtained by first converting the known compound 2-chloropyrimidine to 2-tri-n-butyltinpyrimidine according to the method described in J. Sandosham et al. (Tetrahedron, vol. 50, p. 275, 1994) or a similar method, then converting this compound to a pyrimidinyllithium derivative according to the method described in that reference or a similar method. Next, this compound is reacted with a piperidone derivative having the-formula (XXII) or formula (XXIII):

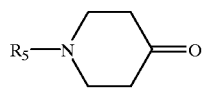

(XXII)

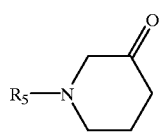

(XXIII)

wherein, $R^5$ indicates a t-butoxycarbonyl group, ethoxycarbonyl group, or acetyl group to obtain a piperidylpyrimidine derivative having the general formula (XXIV):

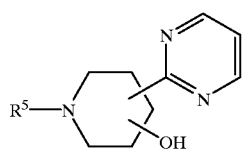

(XXIV)

wherein $R^5$ is the same as defined above, when the 2-pyrimidinyl group is bonded to the 3-position of the piperidyl group, the hydroxy group is bonded to the 3-position of the piperidyl group, while when the 2-pyrimidinyl group is bonded to the 4-position of the piperidyl group, the hydroxy group is bonded to the 4-position of the piperidyl group.

The resultant piperidylpyrimidine derivative (XXIV) is reacted with thionyl chloride, methanesulfonyl chloride, trifluoromethanesulfonyl chloride, or phosphorus oxychloride or another acid chloride derivative, if necessary, in the presence of triethylamine, pyridine, or another base or is reacted with a Burgess reagent (E. M. Burgess et al., J. Org. Chem., vol. 38, p. 26, 1973) to obtain the tetrahydropyrimidine derivative having the general formula (XXVa):

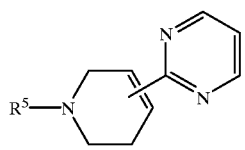

(XXVa)

wherein $R^5$ is the same as defined above, and the 2-pyrimidinyl group in the formula is bonded to the 3-position or 4-position of the 1,2,5,6-tetrahydropyridyl group). Next, by treating the compound by trifluoroacetic acid or another acid, it is possible to obtain the useful synthetic intermediate of the 2-(1,2,5,6-tetrahydropyridyl) pyrimidine derivative (VIIa) of the general formula (VII), wherein $R^3$ and $R^4$ respectively indicate a hydrogen atom and the dotted line shows the presence of a combining bond.

Further, this synthetic intermediate (VIIa) may be obtained by directly treating the piperidylpyrimidine derivative having the general formula (XXIV) with trifluoroacetic acid or another acid.

Further, the pyrimidine derivative (VIIb)

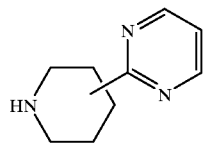

(VIIb)

where, in the general formula (VII), for example $R^3$ and $R^4$ respectively indicate a hydrogen atom, the dotted line shows the absence of a combining bond, and the 2-pyrimidinyl group is bonded to the 3-position or 4-position of the piperidinyl group can be obtained as follows.

That is, the tetrahydropyridylpyrimidine derivative having the general formula (XXVa) is hydrogenated in the presence of a palladium/carbon catalyst to form the piperidylpyrimidine derivative having the general formula (XXVb):

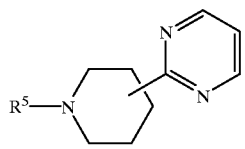

(XXVb)

wherein, $R^5$ is the same as defined above, and the 2-pyrimidinyl group is bonded to the 3-position or 4-position of the piperidyl group. The resultant piperidylpyrimidine derivative (XXVb) is treated with trifluoroacetic acid or another acid to obtain the useful synthetic intermediate of the 2-piperidylpyrimidine derivative (VIIb).

Further, the 2-piperidylpyrimidine derivative (VIIb) may be obtained by direct catalytic reduction of the above 2-(1,2,5,6-tetrahydropyridyl)pyrimidine (VIIa).

Further, the pyrimidine derivative having the above general formula (VII) may be synthesized by the following separate method. The compound having the above general formula (VIIa) in the general formula (VII) is obtained as follows:

First for example 3-or 4-cyanopyridine is converted to 3-or 4-amidinopyridine according to the method of H. Fischer et al. (J. Heterocyclic. Chem., vol. 17, p. 333, 1980) or a similar method, then is made to engage in a condensation dehydrogenation reaction with malonaldehyde, malonaldehydebis(dimethylacetal), etc. to obtain the pyrimidinylpyridine derivative having the general formula (XXVI):

(XXVI)

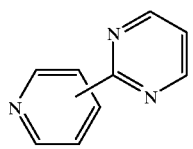

wherein, the 2-pyrimidinyl group is bonded to the 3-position or 4-position of the pyridine ring. Next, the substituent group $R^6$ is introduced into the pyridine ring to convert this compound to the compound having the general formula (XXVIIa):

(XXVIIa)

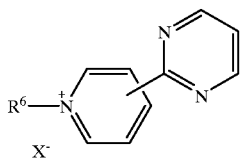

wherein, $R^6$ indicates a $C_1$ to $C_4$ lower alkyl group, benzyl group, or methoxybenzyl group, X indicates a halogen atom, and the 2-pyrimidinyl group is bonded to the 3-position or 4-position of the pyridinium ring. Next, this is reduced with sodium borohydride to form the compound having the general formula (XXVIIIa):

(XXVIIIa)

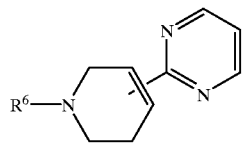

wherein, $R^6$ is the same as defined above, and the 2-pyrimidinyl group is bonded to the 3-position or 4-position of the 1,2,5,6-tetrahydropyridyl group). Next, this compound is reacted with ethyl chloroformate, phenyl chloroformate, 1-chloroethyl chloroformate or 2-trimethylsilylethyl chloroformate etc. to form the compound having the general formula (XXIXa):

(XXIXa)

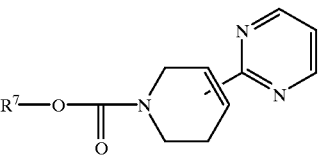

wherein, $R^7$ indicates a $C_1$ to $C_4$ lower alkyl group, 1-chloroethyl group, phenyl group, or 2-trimethylsilylethyl group, and the 2-pyrimidinyl group is bonded to the 3-position or 4-position of the 1,2,5,6-tetrahydropyridyl group. The obtained compound may then be broken down with methanol, ethanol, or another alcohol, hydrolyzed with hydrochloric acid, acetic acid, sulfuric-acid, bromic acid, or another acids or broken down with tetrabutylammoniumfluoride (TBAF) or another fluoride to obtain the useful synthetic intermediate having the pyrimidinyl derivative (VIIa).

Further, the compound having the above general formula (VIIb) in the general formula (VII) may be obtained as follows:

The compound having the above general formula (XXVIIIa) is hydrogenated in the presence of a palladium/carbon catalyst if necessary with the addition of hydrochloric acid or another acid to make the compound having the general formula (XXVIIIb):

(XXVIIIb)

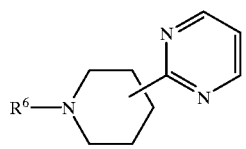

wherein, $R^6$ is the same as defined above, and the 2-pyrimidinyl is bonded to the 3-position or 4-position of the piperidyl group). The compound (XXVIIIb) thus obtained is reacted with ethyl chloroformate, phenyl chloroformate, 1-chloroethyl chloroformate or 2-trimethylsilylethyl chloroformate etc. to obtain the compound having the general formula (XXIXb):

(XXIXb)

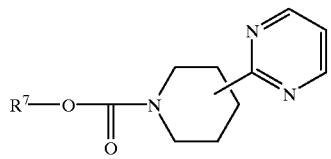

wherein $R^7$ is a $C_1$ to $C_4$ lower alkyl group, 1-chloroethyl group, phenyl group, or 2-trimethylsilylethyl group and the 2-pyrimidinyl group is bonded to the 3-position or 4-position of the piperidyl group. The compound thus obtained may then be broken down with methanol, ethanol, or another alcohol, hydrolyzed with hydrochloric acid, acetic acid, sulfuric acid, bromic acid, or another acid, or broken down with tetrabutylammoniumfluoride (TBAF) or another fluoride to obtain the useful synthetic intermediate having the pyrimidinyl derivative (VIIb).

Further, this piperidyl pyrimidine (VIIb) can be obtained by direct catalytic reduction of the 1,2,5,6-tetrahydropyridylpyrimidine having the above general formula (VIIa).

Further, the pyrimidine derivatives (VIIc):

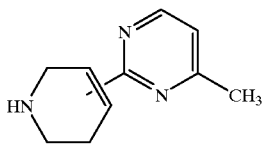

(VIIc)

where in the general formula (VII), for example, $R^3$ indicates an alkyl group, for example, a methyl group, $R^4$ indicates a hydrogen atom, the dotted line indicates the presence of a combining bond, and the 2-pyrimidinyl group is bonded to the 3-position or 4-position of the 1,2,5,6-tetrahydropyridyl group may be obtained by a condensation dehydrogenation reaction of 3- or 4-amidinopyridine and acetoaldehyde dimethylacetal to obtain the general formula (XXX):

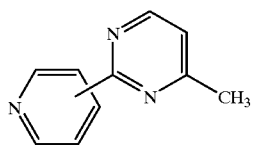

(XXX)

then performing the same procedure as with the compound (VIIa).

Further, the pyrimidine derivative (VIId):

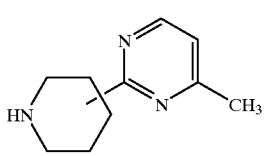

(VIId)

where, in the general formula (VII), for example $R^3$ indicates an alkyl group, for example, a methyl group, $R^4$ indicates a hydrogen atom, the dotted line shows the absence of a combining bond, and the 2-pyrimidinyl group is bonded to the 3-position or 4-position of the piperidyl group may be synthesized by hydrolysis of the above pyrimidine derivative (VIIc) using, if necessary, hydrochloric acid or another acid.

Further, the pyrimidine derivative (VIIe):

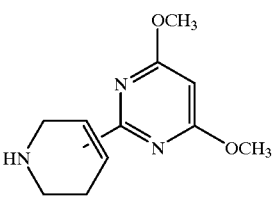

(VIIe)

where, in the general formula (VII), for example, $R^3$ and $R^4$ indicate an alkoxy 3group, for example, a methoxy group, the dotted line indicates the presence of a combining bond, and the 2-pyrimidinyl group is bonded to the 3-position or 4-position of the 1,2,5,6-tetrahydropyridyl group may be synthesized by condensation reaction between 3-or 4-amidinopyridine and dichloride malonate to obtain the general formula (XXXI):

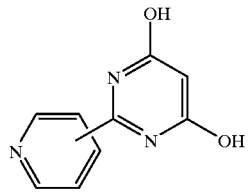

(XXXI)

then dimethylating this combined with methyl iodide to convert to the compound (XXXII):

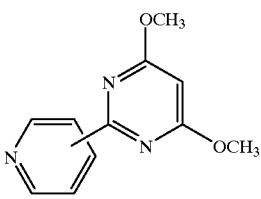

(XXXII)

and, then, performing the same procedure as with the Compound (VIIa).

Further, the pyrimidine derivatives (VIIf):

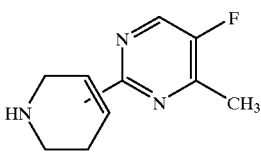

(VIIf)

where in the general formula (VII), for example, $R^3$ indicates an alkyl group, for example, a methyl group, $R^4$ indicates a halogen, for example, a fluoro group, the dotted line indicates the presence of a combining bond, and the 2-pyrimidinyl group is bonded to the 3-position or 4-position of the 1,2,5,6-tetrahydropyridyl group may be obtained by a condensation dehydrogenation reaction with 2-fluoro-3-oxo-butyraldehyde dimethylacetal to obtain the general formula (XXXIII):

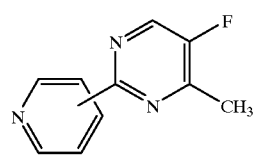

(XXXIII)

then performing the same procedure as with the compound (VIIa).

The pyridine derivatives in the intermediate compounds having the general formula (XXI) can be produced for example as follows.

They may be obtained by the method described in W. S. Saari et al. (J. Med. Chem., vol. 27, p. 1182, 1984) or a similar method.

Further, they may be obtained as follows, as a separate method. That is, for example, the pyridine derivative (XXIa)

(XXIa)

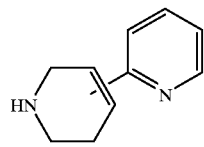

where, in the general formula (XXI), Z' indicates a 2-pyridyl group, the dotted line indicates the presence of a combining bond, and the 2-pyridyl group is bonded to the 3-position or 4-position of the 1,2,5,6-tetrahydropyridyl group may be obtained as follows:

The known compound 2, 4-dipyridyl or 2,3-dipyridyl is converted to the compound having the general formula (XXVIIb):

(XXVIIb)

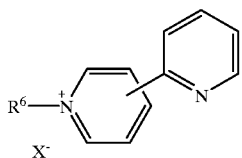

wherein, $R^6$ indicates a $C_1$ to $C_4$ lower alkyl group, benzyl group, or methoxybenzyl group, X indicates a halogen atom, and the 2-pyridyl group is bonded to the 3-position or 4-position of the pyridinium group) according to the method described in H. Fischer et al. (J. Heterocyclic. Chem., vol. 17, p. 333, 1980) or a similar method. Next, this compound is reduced with sodium borohydride to form the compound having the general formula (XXVIIIc):

(XXVIIIc)

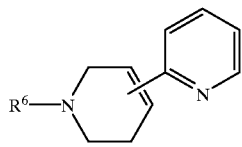

wherein, $R^6$ is the same as defined above, and the 2-pyridyl group is bonded to the 3-position or 4-position of the 1,2,5,6-tetrahydropyridyl group). Next, this compound is reacted with ethyl chloroformate, phenyl chloroformate, 1-chloroethyl chloroformate or 2-trimethylsilylethyl chloroformate or the like to form the compound having the general formula (XXIXc):

(XXIXc)

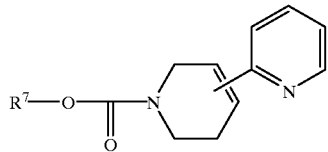

wherein, $R^7$ indicates a $C_1$ to $C_4$ lower alkyl group, 1-chloroethyl group, phenyl group, or 2-trimethylsilylethyl group, and the 2-pyridyl group is bonded to the 3-position or 4-position of the 1,2,5,6-tetrahydropyridyl group). The compound thus obtained is broken down with methanol, ethanol, or another alcohol, hydrolyzed with hydrochloric acid, acetic acid, sulfuric acid, hydrobromic acid, or another acid, or broken down with tetrabutylammonium-fluoride (TBAF) or another fluoride to obtain the useful synthetic intermediate having the pyridine derivative (XXIa). Further, the pyridine derivative (XXIb)

(XXIb)

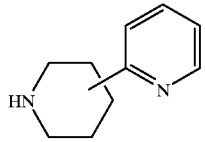

where, in the general formula (XXI), for example, Z' indicates a 2-pyridyl group, the dotted line shows the absence of a combining bond, and the 2-pyridyl group is bonded to the 3-position or 4-position of the piperidyl group may be obtained as follows:

The compound having the above general formula (XXVIIIc) is hydrogenated in the presence of a palladium/carbon catalyst, if necessary, with the addition of hydrochloric acid or another acid to derive the compound having the general formula (XXVIIId):

(XXVIIId)

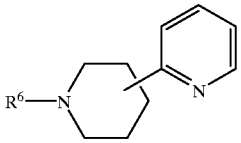

wherein, $R^6$ is the same as defined above, and the 2-pyridyl group is bonded to the 3-position or 4-position of the piperidyl group). Next, this compound is reacted with ethyl thloroformate, phenyl chloroformate, 1-chloroethyl chloroformate, or 2-trimethylsilylethyl chloroformate etc. to obtain the compound having the general formula (XXIXd):

(XXIXd)

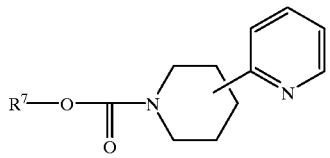

wherein $R^7$ indicates a $C_1$ to $C_4$ lower alkyl group, 1-chloroethyl group, phenyl group, or 2-trimethylsilylethyl group, and the 2-pyridyl group is bonded to the 3-position or 4-position of the piperidyl group. The compound (XXIXd), thus obtained is broken down with methanol, ethanol, or another alcohol, hydrolyzed with hydrochloric acid, acetic acid, sulfuric acid, bromic acid, or another acid, or broken down with tetrabutylammoniumfluoride (TBAF) and another fluoride to obtain the useful synthetic intermediate of the pyridyl derivative (XXIb).

Further this piperidylpyridine (XXIb) can be obtained by direct catalytic reduction of the 1,2,5,6-tetrahydropyridine having the above general formula (XXIa).

The compound having the final compound (III) can be produced by substitution condensation of the synthetic intermediate having the general formula (XXI), for example, the synthetic intermediate of the pyrimidine derivative (VII) illustrated in (VIIa) to (VIIf) or the synthetic intermediate of the pyridine derivative illustrated in (XXIa) to (XXIb) with the synthesis intermediate, (V) illustrated in (Va) to (Vj) using if necessary triethylamine or potassium carbonate or another base or sodium iodide or another catalyst.

3) Synthesis of final compound having formula (III) by separate method

Further, the compound having the final compound (III) may be synthesized through the synthetic intermediate having the compound having the general formula (VI) wherein Z' is the above formula (IV)

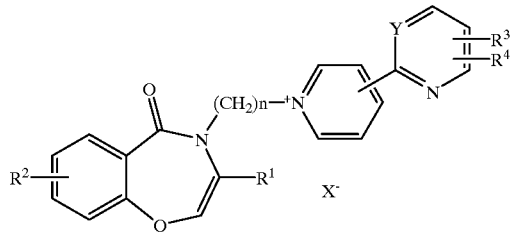

wherein, $R^1$, $R^2$, $R^3$, $R^4$, Y, X, and n are the same as defined above.

Here, the synthetic intermediate having the general formula (VI) may be synthesized as follows:

That is, the compound having the general formula (IIk):

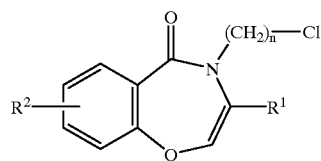

(IIk)

wherein, $R^1$, $R^2$, n are the same as defined above) where in the above general formula (V), for example, Q indicates a chlorine atom may be reacted in the presence of sodium iodide with a 2,3'-dipyridyl derivative, 2,4'-dipyridyl derivative, or pyrimidinlpyridine derivative having the above general formula (XXVI) to form the useful synthetic intermediate having the above general formula (VI).

By reacting sodium borohydride with the obtained synthetic intermediate (VI), it is possible to produce the compound having the final compound (III).

Further, according to the present invention, it is possible to provide a novel pyrimidine derivative and its salt having the general formula (XXXIV):

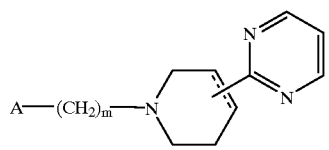

(XXXIV)

wherein m is an integer of 1 to 5, a dotted line indicates the presence or absence of a combining bond, A indicates a hydrogen atom, a $C_1$ to $C_4$ lower alkoxy group, a group indicated by the following formula:

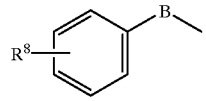

wherein, $R^8$ indicates a hydrogen atom, halogen atom, $C_1$ to $C_4$ lower alkyl group, $C_1$ to $C_4$ lower alkoxy group, or hydroxy group, and B indicates a single bond, oxygen atom, carbonyl group, hydroxymethylene group, or group —CONH—), or a group indicated by the following formula:

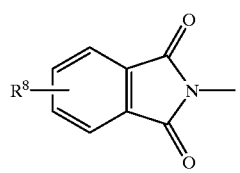

wherein, $R^9$ indicates a hydrogen atom, halogen atom, $C_1$ to $C_4$ lower alkyl group, $C_1$ to $C_4$ lower alkoxy group, or hydroxy group), the form of bonding of the 2-pyrimidinyl group and the 1,2,5,6-tetrahydropyridyl group or piperidyl group in the formula being a 3-position or 4-position. These compounds and their salts are useful, as synthetic intermediates of medicaments synthesized by the novel pyrimidine derivative having the above general formula (VII), useful as the synthetic intermediate of the present invention, which is more effective and has fewer side effects and is used for the treatment of anxiety neurosis, phobias, obsessive-compulsive disorders, schizophrenia, post-cardiac trauma stress disorders, depression disorders, psychosomatic disorders and other psychoneurotic disorders, eating disorders, menopausal disorders, infantile autism and other disorders, and also emesis or disorders involving the cerebral circulatory system accompanying cerebral infarction and cerebral hemorrhaging. The main types of the compound having the general formula (XXXIV) are shown in Reference Examples 1 to 11.

| Ref. ex. | Chemical structure | m. p. (° C.) | IR (cm$^{-1}$) | NMR (δ, ppm) | FAB-Mass |
|---|---|---|---|---|---|
| 1 | H—(CH$_2$)$_8$—N⟨piperidine⟩-pyrimidine | (Fumarate) 107~110 | (Fumarate, KBr) 3437, 2960, 2710, 2656, 1702, 1641, 1558, 1422, 1263 | (Fumarate, DMSO-d$_6$) 8.77~8.79(2H, m), 7.35(1H, t, J=5Hz), 7.15(1H, s), 6.62(4H, s), 3.41~3.50(2H, m), 2.86~2.97(2H, m), 2.60~2.74(4H, m), 1.52~1.65(2H, m), 0.89~0.96(3H, m) | 204 (M + Z)$^+$ |

| Ref. ex. | Chemical structure | m. p. (° C.) | IR (cm$^{-1}$) | NMR (δ, ppm) | FAB-Mass |
|---|---|---|---|---|---|
| 2 | H—(CH$_2$)$_8$—N(piperidine)—pyrimidine | (Fumarate) 121~124 | (Fumarate, KBr) 3437, 2923, 1695, 1572, 1427, 1384, 1273 | (Fumarate, DMSO-d$_6$) 8.75(2H, d, J=5Hz), 7.34(1H, t, J=5Hz), 6.59(4H, s), 3.14~3.17 (2H, m), 2.92(1H, brs), 2.45~2.56(4H, m), 1.88~2.03(4H, m), 1.52~1.58(2H, m), 0.89(3H, t, J=7Hz) | 206 (M + H)$^+$ |
| 3 | H—(CH$_2$)$_8$—N(tetrahydropyridine)—pyrimidine | | (CHCl$_3$) 2962, 1569, 1424 | (free, CDCl$_3$) 8.66(2H, d, J=5Hz), 7.33~7.35 (1H, m), 7.07(1H, t, J=5Hz), 3.55~3.61 (2H, m), 2.67(2H, t, J=6Hz), 2.54~2.58 (2H, m), 2.46~2.50 (2H, m), 1.65~1.75 (2H, m), 0.95(3H, t, J=7Hz) | 204 (M + H)$^+$ |
| 4 | Ph—CH$_2$—N(tetrahydropyridine)—pyrimidine | (Fumarate) 135~138 | (Fumarate, KBr) 3437, 2913, 1702, 1684, 1646, 1560, 1498, 1421, 1216 | (Fumarate, DMSO-d$_6$) 8.74(2H, d, J=5Hz), 7.26~7.35(6H, m), 7.15(1H, brs), 6.62 (4H, s), 3.63(2H, s), 3.14~3.20(2H, m), 2.66~2.70(2H, m), 2.58~2.65(2H, m) | 252 (M + H)$^+$ |
| 5 | Ph—O—(CH$_2$)$_3$—cyclohexyl—pyrimidine | (HCl salt) 177~179 | (HCl salt, KBr) 3441, 2922, 1604, 1560, 1498, 1424, 1298, 1175 | (HCl salt, DMSO-d$_6$) 9.75~9.83(1H, brs), 8.83(2H, d, J=5Hz), 7.48~7.55(1H, m), 7.26~7.34(2H, t, J=8Hz), 7.11~7.18 (1H, m), 6.92~6.99 (3H, m), 4.06~4.12 (2H, m), 3.70~3.81 (2H, m), 3.35~3.42 (2H, m), 2.78~3.06 (4H, m), 2.18~2.27 (2H, m) | 296 (M + H)$^+$ |
| 6 | 4-F-C$_6$H$_4$—C(O)—(CH$_2$)$_2$—N(tetrahydropyridine)—pyrimidine | (Fumarate) 155~158 | (Fumarate, KBr) 3437, 2913, 1687, 1642, 1559, 1423, 1296, 1171 | (Fumarate, DMSO-d$_6$) 8.78(2H, d, J=5Hz), 8.03~8.06(2H, m), 7.31~7.35(3H, m), 7.14(1H, brs), 6.62 (4H, s), 3.47~3.62 (2H, m), 3.09~3.17 (2H, m), 2.91~3.07 (2H, m), 2.75~2.88 (2H, m), 2.65~2.74 (2H, m), 1.90~2.01 (2H, m) | 326 (M + H)$^+$ |
| 7 | 4-F-C$_6$H$_4$—C(O)—(CH$_2$)$_2$—N(piperidine)—pyrimidine | (Fumarate) 131~134 | (Fumarate, KBr) 3438, 2927, 1687, 1599, 1563, 1427, 1384, 1289, 986 | (Fumarate, DMSO-d$_6$) 8.73(2H, d, J=5Hz), 8.03~8.07(2H, m), 7.32~7.36(3H, m), 6.59(4H, s), 3.05(4H, t, J=7Hz), 2.79~2.90 (1H, m), 2.51~2.59 (2H, m), 2.22~2.35 (2H, m),1.77~1.95 (6H, m) | 328 (M + H)$^+$ |

-continued

| Ref. ex. | Chemical structure | m. p. (° C.) | IR (cm$^{-1}$) | NMR ($\delta$, ppm) | FAB-Mass |
|---|---|---|---|---|---|
| 8 | F-C6H4-CH(OH)-(CH2)3-N(tetrahydropyridine)-pyrimidine | (Fumarate) 149~152 | (Fumarate, KBr) 3436, 3043, 1718, 1684, 1608, 1560, 1425, 1382, 1297 | (Fumarate, DMSO-d$_6$) 8.75(2H, d, J=5Hz), 7.30~7.37(3H, m), 7.08~7.13(3H, m), 6.60(4H, s), 4.53~4.56 (1H, m), 3.16~3.21 (2H, m), 2.57~2.65 (3H, m), 2.42~2.50 (4H, m), 1.42~1.65 (4H, m) | 328 (M + H)$^+$ |
| 9 | C6H5-C(=O)-NH-(CH2)4-N(piperidine)-pyrimidine | (Fumarate) 160~162 | (Fumarate, KBr) 3510, 3425, 2958, 1644, 1589, 1545, 1493, 1424, 1228 | (Fumarate, DMSO-d$_6$) 8.73(2H, d, J=5Hz), 8.42(1H, brs), 7.83 (2H, d, J=7Hz), 7.43~ 7.50(3H, m), 7.32(1H, t, J=5Hz), 6.55(4H, s), 3.26~3.32(2H, m), 3.00~3.03(2H, m), 2.78~2.85(1H, m), 2.40~2.45(2H, m), 2.10~2.20(2H, m), 1.89~1.98(1H, m), 1.81~1.86(2H, m), 1.50~1.58(4H, m) | 339 (M + H)$^+$ |
| 10 | phthalimide-N-(CH2)4-N(tetrahydropyridine)-pyrimidine | (Fumarate) 172~175 | (Fumarate, KRr) 3460, 3035, 1769, 1711, 1559, 1466, 1424, 1340, 1296 | (Fumarate, DMSO-d$_6$) 8.75(2H, d, J=5Hz), 7.81~7.88(4H, m), 7.31(1H, t, J=5Hz), 7.13(1H, brs), 6.60 (4H, s), 3.61(2H, t, J=7Hz), 3.08~3.22 (2H, m), 2.63~2.70 (2H, m), 2.56~2.61 (2H, m), 2.45~2.55 (2H, m), 1.61~1.70 (2H, m), 1.49~1.59 (2H, m) | 363 (M + H)$^+$ |
| 11 | phthalimide-N-(CH2)4-N(piperidine)-pyrimidine | (Fumarate) 196~199 | (Fumarate, KRr) 3455, 3036, 2945, 1770, 1713, 1616, 1572, 1562, 1428, 1335 | (Fumarate, DMSO-d$_6$) 8.73(2H, d, J=5Hz), 7.82~7.88(4H, m), 7.33(1H, t, J=5Hz), 6.58(4H, s), 3.61(2H, t, J=7Hz), 2.99~3.06 (2H, m), 2.78~2.89 (1H, m), 2.45~2.56 (2H, m), 2.18~2.30 (2H, m), 1.90~2.00 (2H, m), 1.75~1.90 (2H, m), 1.58~1.69 (2H, m), 1.45~1.58 (2H, m) | 365 (M + H)$^+$ |

The compounds having the general formulae (I), (II), and (III) may be converted into acid addition salts by known methods. Examples of pharmaceutically acceptable salts are hydrochlorides, nitrates, sulfates, hydrobromates, phosphates, and other inorganic acid salts and also methanesulfonates, acetates, oxalates, succinates, malonates, tartarates, maleates, fumarates, lactates, citrates, and other organic acid salts.

To use the compounds having the general formulae (I), (II), and (III) and their pharmaceutically acceptable salts as medicaments, these can be administered alone, but it is preferable to use other ordinary medicaments acceptable carriers, excipients, diluents, etc. to prepare them by usual methods into preparations in accordance with the method of administration. As examples of such preparations, for example, for oral administration, capsules, tablets, granules, powders, syrups, dry syrups, and other preparations may be mentioned, while for nonoral administration, injections and also rectal suppositories, vaginal suppositories, and other suppositories, sprays and other nasal applications, ointments, transdermal absorption tapes, and other transdermal absorption agents may be mentioned.

The clinical dosage of the compounds having the general formulae (I), (II), and (III) and their medicamently acceptable salts differs depending on the symptoms, the degree of gravity, age, complications, etc. and differs depending on the preparations, but for oral administration and effective ingredient of an amount per normal adult per day of 1 to 100 mg, preferably 1 to 50 mg, more preferably 5 to 10 mg and for nonoral administration, an amount of one-tenth to one-half the oral administration may be administered. These dosages may be suitably adjusted in accordance with the age, symptoms, etc. of the patient.

The toxicity of the compounds having the general formulae (I), (II), and (III) is low, for example, the acute toxicity $LD_{50}$ at 24 hours after oral administration of the compound of Example 56 to six-week old male rats is 100 mg/kg or more. This value is over 50 times or more of the expected clinical dosage and therefore, it is judged that the safety of the compounds according to the present invention is high.

The compounds having the general formulae (I), (II), and (III), as shown in the later Evaluation Examples, exhibit a strong affinity to a serotonin 5-$HT_{1A}$ receptor on the order of an $IC_{50}$ of 1 nM, but exhibit only a weak affinity to the dopamine $D_2$ receptor of an $IC_{50}$ of more than about 0.1 $\mu$M. Further, these compounds, as shown in the later Evaluation Examples, exhibit an anticonflict action. This shows that these compounds have little side effects and are useful as agents for the treatment of anxiety neurosis, dysthymia, schizophrenia, and obsessive-compulsive disorders, and also emesis.

Further, the compounds having the general formulae (I), (II), and (III), as shown in the later Evaluation Examples, have the action of suppressing cerebral infarction in a transient right middle cerebral artery occlusion (MCAO) model, so these compounds clearly have a protective action on the brain in cerebral ischemic conditions and are useful as drugs for the treatment of cerebral infarction and other ischemic brain diseases.

EXAMPLES

The present invention will now be explained in further detail with reference to Examples and Test Examples, but, of course, the scope of the present invention is not limited to these Examples.

First, an explanation will be given of the methods of synthetic intermediates (V), (VI), and (VII) in Examples 1 to 30, then the method of synthesis of the final compound in Examples 31 to 87. The structures and physical properties of the synthesized compounds are shown in Table 1.

Example 1

Synthesis of 7-chloro-4-(2-chloroethyl)-4,5-dihydro-1,4-benzoxazepin-5-one 50 mg of 7-chloro-4,5-dihydro-1,4-benzoxazepin-5-one was dissolved in dimethylformamide (1 ml), then 12 mg (1.2 equivalents) of 60% sodium hydride was added under ice cooling. This was agitated for 30 minutes, then 54 mg (1.5 equivalents) of 1-bromo-2-chloroethane was added and the result was agitated at room temperature for 10 hours. Ice water was added to the reaction solution, and extraction was performed by ethyl acetate. This ethyl acetate extract was washed by saline and was dried with anhydrous magnesium sulfate. The solvent was distilled off and the resultant crude product was refined with silica gel column chromatography (hexane: ethyl acetate=4:1) to obtain the above-referenced compound in an amount of 28 mg (yield of 42%).

Example 2

Synthesis of 4-(4-bromobutyl)-4,5-dihydro-1,4-benzoxazepin-5-one 1.0 g of 4,5-dihydro-1,4-benzoxazepin-5-one was dissolved in 50 ml of dimethylformamide, then 298 mg (1.2 equivalents) of 60% sodium hydride was added under ice cooling. This was agitated for 30 minutes, then 4.7 g (3 equivalents) of 1,4-dibromobutane was added and the resultant mixture was agitated at room temperature for 6 hours.

The resultant compound was reacted, treated, and refined in the same way as in Example 1 to obtain the above-referenced compound in an amount of 1.5 g (yield of 75%).

Example 3

Synthesis of 4-(3-chloropropyl)-4,5-dihydro-8-methoxy-1,4-benzoxazepin-5-one 1.0 g of 4,5-dihydro-8-methoxy-1,4-benzoxazepin-5-one was dissolved in 50 ml of dimethylformamide, then 298 mg (1.2 equivalents) of 60% sodium hydride was added under ice cooling. This was agitated for 30 minutes, then 4.7 g (3 equivalents) of 1,4-dibromobutane was added and the resultant mixture was agitated at room temperature for 6 hours.

The resultant compound was reacted, treated, and refined in the same way as in Example 1 to obtain the above-referenced compound in an amount of 1.5 g (yield of 75%).

Example 4

Synthesis of 4-(4-bromobutyl)-4,5-dihydro-8-methoxy-1,4-benzoxazepin-5-one 200 mg of 4,5-dihydro-8-methoxy-1,4-benzoxazepin-5-one was dissolved in 10 ml of dimethylformamide, then 50 mg (1.2 equivalents) of 60% sodium hydride was added under ice cooling. This was agitated for 30 minutes, then 790 mg (3 equivalents) of 1,4-dibromobutane was added and the resultant mixture was agitated at room temperature for 6 hours.

The resultant compound was reacted, treated, and refined in the same way as in Example 1 to obtain the above-referenced compound in an amount of 231 mg (yield of 61%).

Example 5

Synthesis of 4-(5-bromopentyl)-4,5-dihydro-8-methoxy-1,4-benzoxazepin-5-one 350 mg of 4,5-dihydro-8-methoxy1,4-benzoxazepin-5-one was dissolved in 5 ml of dimethylformamide, then 88 mg (1.2 equivalents) of 60% sodium hydride was added. This was agitated for 30 minutes, then 0.60 ml (2.4 equivalents) of 1,5-dibromopentane was added and the resultant mixture was agitated at room temperature for 6 hours.

The resultant compound was reacted, treated, and refined in the same way as in Example 1 to obtain the above-referenced compound in an amount of 410 mg (yield of 66%).

Example 6

Synthesis of 4-(5-bromopentyl)-4,5-dihydro-1,4-benzoxazepin-5-one 250 mg of 4,5-dihydro-1,4-benzoxazepin-5-one was dissolved in 15 ml of dimethylformamide, then 74 mg (1.2 equivalents) of 60% sodium hydride was added under ice cooling. This was agitated for 30 minutes, then 0.51 ml (2.4 equivalents) of 1,5-dibromopentane was added and the resultant mixture was agitated at room temperature for 6 hours.

The resultant compound was reacted, treated, and refined in the same way as in Example 1 to obtain the above-referenced compound in an amount of 350 mg (yield of 73%).

Example 7

Synthesis of 4-(3-chloropropyl)-4,5-dihydro-3-methyl-1,4-benzoxazepin-5-one 300 mg of 4,5-dihydro-3-methyl1,4-benzoxazepin-5-one was dissolved in 20 ml of dimethylformamide, then 82 mg (1.2 equivalents) of 60% sodium hydride was added under ice cooling. This was agitated at room temperature for 1 hour, then 0.25 ml (1.5 equivalents) of 1,3-bromochloropropane was added and the resultant mixture was agitated for 3 hours.

The resultant compound was reacted, treated, and refined in the same way as in Example 1 to obtain the above-referenced compound in an amount of 370 mg (yield of 86%).

Example 8

Synthesis of 4-(4-bromobutyl)-4,5-dihydro-3-methyl-1,4-benzoxazepin-5-one 2.0 g of 4,5-dihydro-3-methyl1,4-benzoxazepin-5-one was dissolved in 120 ml of dimethylformamide, then 548 mg (1.2 equivalents) of 60% sodium hydride was added under ice cooling. This was agitated at room temperature for 1 hour, then 4.1 ml (3 equivalents) of 1,4-dibromobutane was added and the resultant mixture was agitated for 3 hours.

The resultant compound was reacted, treated, and refined in the same way as in Example 1 to obtain the above-referenced compound in an amount of 3.0 g (yield of 84%).

Example 9

Synthesis of 4-(5-bromopentyl)-4,5-dihydro-3-methyl-1,4-benzoxazepin-5-one 250 mg of 4,5-dihydro-3-methyl-1,4-benzoxazepin-5-one was dissolved in 20 ml of dimethylformamide, then 68 mg (1.2 equivalents) of 60% sodium hydride was added under ice cooling. This was agitated at room temperature for 1 hour, then 0.78 ml (4 equivalents) of 1,5-dibromopentane was added and the resultant mixture was agitated for 6 hours.

The resultant compound was reacted, treated, and refined in the same way as in Example 1 to obtain the above-referenced compound in an amount of 380 mg (yield of 83%).

Example 10

Synthesis of 4-(4-chlorobutyl)-4,5-dihydro-3-ethyl-1,4-benzoxazepin-5-one 430 mg of 4,5-dihydro-3-ethyl-1,4-benzoxazepin-5-one was dissolved in 10 ml of dimethylformamide, then 110 mg (1.2 equivalents) of 60% sodium hydride was added under ice cooling. This was agitated for 30 minutes, then 480 mg (1.2 equivalents) of 1-bromo-4-chlorobutane was added and the resultant mixture was agitated at room temperature for 6 hours.

The resultant compound was reacted, treated, and refined in the same way as in Example 1 to obtain the above-referenced compound in an amount of 420 mg (yield of 65%).

Example 11

Synthesis of 4-(4-bromobutyl)-4,5-dihydro-3,8-dimethyl-1,4-benzoxazepin-5-one 2.84 g of 4,5-dihydro-3,8-dimethyl-1,4-benzoxazepin-5-one was dissolved in 75 ml of acetone, 12.9 g (4 equivalents) of 1,4-dibromobutane and 6.22 g (3 equivalents) of potassium carbonate were added, then the resultant mixture was heated and refluxed for 12 hours. This was allowed to cool, then was filtered, the filtrate was concentrated, and the residue was refined by silica gel column chromatography (hexane:ethyl acetate=3:1) to obtain the above-referenced compound in an amount of 3.3 g (yield of 68%).

Example 12

Synthesis of 4-(4-bromobutyl)-4,5-dihydro-3,7-dimethyl-1,4-benzoxazepin-5-one 950 mg of 4,5-dihydro-3,7-dimethyl-1,4-benzoxazepin-5-one was dissolved in 30 ml of acetone, 4.3 g (4 equivalents) of 1,4-dibromobutane and 2.1 g (3 equivalents) of potassium carbonate were added, then the resultant mixture was heated and refluxed for 10 hours.

The resultant compound was reacted, treated, and refined in the same way as in Example 11 to obtain the above-referenced compound in an amount of 1.2 g (yield of 74%).

Example 13

Synthesis of 4-(4-bromobutyl)-4,5-dihydro-7-fluoro-3-methyl-1,4-benzoxazepin-5-one 416 mg of 4,5-dihydro-7-fluoro-3-methyl-1,4-benzoxazepin-5-one was dissolved in 15 ml of dimethylformamide, then 113 mg (1.2 equivalents) of 60% sodium hydride was added under ice cooling. This was agitated for 30 minutes, then 1 ml (3.6 equivalents) of 1,4-dibromobutane was added and the resultant mixture was agitated at room temperature for 6 hours.

The resultant compound was reacted, treated, and refined in the same way as in Example 1 to obtain the above-referenced compound in an amount of 609 mg (yield of 80%).

Example 14

Synthesis of 4-(5-bromopentyl)-4,5-dihydro-3,7-dimethyl-1,4-benzoxazepin-5-one 346 mg of 4,5-dihydro-3,7-dimethyl-1,4-benzoxazepin-5-one was dissolved in 20 ml of dimethylformamide, then 88 mg (1.2 equivalents) of 60% sodium hydride was added. This was agitated for 30 minutes, then 1.68 g (4 equivalents) of 1,5-dibromopentane was added and the resultant mixture was agitated at room temperature for 4 hours.

The resultant compound was reacted, treated, and refined in the same way as in Example 1 to obtain the above-referenced compound in an amount of 589 mg (yield of 98%).

Example 15

Synthesis of 3-chloro-4-(3-chloropropyl)-4,5-dihydro-1,4-benzoxazepin-5-one 5.0 g of 2,3,4,5-tetrahydro-1,4-benzoxazepin-3,5-dione 5.0 g was dissolved in 100 ml of acetone, 7.8 g (2 equivalents) of potassium carbonate and 5.6 ml (2 equivalents) of 1-bromo-3-chloropropane were added, then the resultant mixture was heated and refluxed for 6 hours. This was allowed to cool, then was filtered and the filtrate was concentrated. The resultant residue was dissolved in 70 ml of phosphorus oxychloride. Further, 20 ml of 4N-HCl solution of dioxane solution was added and the resultant mixture was agitated at 100° C. for 11 hours. The phosphorus oxychloride was distilled off, then an aqueous solution of 10% sodium hydroxide was added under ice cooling. This was extracted by methylene chloride, then was washed by a saturated aqueous solution of sodium hydrogencarbonate and saturated saline and was dried by anhydrous magnesium sulfate. The solvent was distilled off and the resultant crude product was refined by silica gel column chromatography (hexane:ethyl acetate=6:1) to obtain the above-referenced compound in an amount of 2.53 g (yield of 33%).

Example 16

Synthesis of 3-chloro-4-(4-chlorobutyl)-4,5-dihydro-1,4-benzoxazepin-5-one 5.0 g of 2,3,4,5-tetrahydro-1,4-benzoxazepin-3,5-dione 5.0 g was dissolved in 100 ml of acetone, 7.8 g (2 equivalents) of potassium carbonate and 6.5 ml (2 equivalents) of 1-bromo-4-chlorobutane were added, then the resultant mixture was heated and refluxed for 8 hours. This was allowed to cool, then was filtered and the filtrate was concentrated. The resultant residue was dissolved in 50 ml of phosphorus oxychloride. Further, 20 ml of a 4N HCl solution of dioxane was added, then the resultant mixture was agitated at 100° C. for 25 hours.

The resultant compound was reacted, treated, and refined in the same way as in Example 15 to obtain the above-referenced compound in an amount of 4.4 g (yield of 45%).

Example 17

Synthesis of 4-(4-chlorobutyl)-3,8-dichloro-4,5-dihydro-1,4-benzoxazepin-5-one 918 mg of 8-chloro-2,3,4,5-tetrahydro-1,4-benzoxazepin-3,5-dione was dissolved in 20 ml of acetone, 1.2 g (2equivalents) of potassium carbonate and 819 mg (1.1 equivalents) of 1-bromo-4-chlorobutane were added, then the resultant mixture was heated and refluxed for 7 hours. This was allowed to cool, then was filtered and the filtrate was concentrated. The resultant residue was dissolved in 2 ml of phosphorus oxychloride, then 1.4 ml (2 equivalents) of N,N-diethylaniline was added, and the resultant mixture was agitated at 90° C. for 12 hours.

The resultant compound was reacted, treated, and refined in the same way as in Example 15 to obtain the above-referenced compound in an amount of 598 mg (yield of 43%).

Example 18

Synthesis of 3-chloro-4-(4-chlorobutyl)-4,5-dihydro-8-methoxy-1,4-benzoxazepin-5-one 700 mg of 8-methoxy-2,3,4,5-tetrahydro-1,4-benzoxazepin-3,5-dione was dissolved in 20 ml of acetone, 1.0 g (2 equivalents) of potassium carbonate and 690 mg (1.1 equivalents) of 1-bromo-4-chlorobutane were added, then the resultant mixture was heated and refluxed for 8 hours. This was allowed to cool, then was filtered and the filtrate was concentrated. The resultant residue was dissolved in 2 ml of phosphorus oxychloride. Further, 0.5 ml of a 4N-HCl solution of dioxane was added, and the resultant mixture was agitated at 90° C. for 12 hours.

The resultant compound was reacted, treated, and refined in the same way as in Example 15 to obtain the above-referenced compound in an amount of 889 mg (yield of 81%).

Example 19

Synthesis of 3-chloro-4-(4-chlorobutyl)-4,5-dihydro-7-methyl-1,4-benzoxazepin-5-one 700 mg of 7-methyl-2,3,4,5-tetrahydro-1,4-benzoxazepin-3,5-dione was dissolved in 20 ml of acetone, 1.0 g (2 equivalents) of potassium carbonate and 690 mg (1.1 equivalents) of 1-bromo-4-chlorobutane were added, then the resultant mixture was heated and refluxed for 8 hours. This was allowed to cool, then was filtered and the filtrate was concentrated. The resultant residue was dissolved in 2 ml of phosphorus oxychloride. Further, 0.5 ml of a 4N-HCl solution of dioxane was added and the resultant mixture was agitated at 90° C. for 12 hours.

The resultant compound was reacted, treated, and refined in the same way as in Example 15 to obtain the above-referenced compound in an amount of 889 mg (yield of 81%).

Example 20

Synthesis of 3-chloro-4-(5-bromopentyl)-4,5-dihydro-1,4-benzoxazepin-5-one 350 mg of 2,3,4,5-tetrahydro-1,4-benzoxazepin-3,5-dione was dissolved in 20 ml of acetone, 546 mg (2 equivalents) of potassium carbonate and 1.8 g (4 equivalents) of 1,5-dibromopentane were added, then the resultant mixture was heated and refluxed for 8 hours. This was allowed to cool, then was filtered and the filtrate was concentrated. The resultant residue was dissolved in 5 ml of phosphorus oxychloride, then 1 ml of a 4N-HCl solution of dioxane was added, then the result was agitated at 100° C. for 25 hours.

The resultant compound was reacted, treated, and refined in the same way as in Example 15 to obtain the above-referenced compound in an amount of 380 mg (yield of 55%).

Example 21

Synthesis of 4-(4-bromobutyl)-3-chloromethyl-4,5-dihydro-7-methoxy-1,4-benzoxazepin-5-one 2.1 g of 4,5-dihydro-7-methoxy-3-methyl-1,4-benzoxazepin-5-one was dissolved in 50 ml of acetone, 5.5 g (2.5 equivalents) of 1,4-dibromobutane and 3.5 g (2.5 equivalents) of potassium carbonate were added, then the resultant mixture was heated and refluxed for 10 hours. This was allowed to cool, then was filtered, the filtrate was concentrated, and the residue was dissolved in 60 ml of carbon tetrachloride. 1.6 g (1.2 equivalents) of N-chlorosuccinimide was added and the resultant mixture was agitated at 90° C. for minutes 15 minutes. This was allowed to cool, then was filtered, the filtrate was concentrated, water was added, and extraction was performed by methyiene chloride. The methylene chloride extract was washed with water and saturated saline and was dried with anhydrous magnesium sulfate. The solvent was distilled off and the resultant crude product was refined with silica gel column chromatography (hexane:ethyl acetate= 4:1) to obtain the above-referenced compound in an amount of 1.4 g (yield of 37%).

Example 22

Synthesis of 4-(4-bromobutyl)-4,5-dihydro-3-methoxymethyl-1,4-benzoxazepin-5-one 1.0 g of 4,5-dihydro-3-methyl-1,4-benzoxazepin-5-one was dissolved in 30 ml of carbon tetrachloride, 910 mg (1.2 equivalents) of N-chlorosuccinimide was added, and the resultant mixture was agitated at 90° C. for 1 hour. This was allowed to cool, then was filtered, the filtrate was concentrated, then the resultant mixture was dissolved in 20 ml of methanol. Further, 0.86 ml (1.1 equivalents) of a methanol solution of 28% sodium methylate was added, then the resultant mixture was agitated at room temperature for 40 minutes. This was concentrated, then water was added, and extraction was performed with methylene chloride. This methylene chloride extract was washed with water and saturated saline and was dried by anhydrous magnesium sulfate, then concentrated. 368 mg of the residue was dissolved in 15 ml of dimethylformamide, then 87 mg (1.2 equivalents) of 60% sodium hydride was added under ice cooling. This was agitated for 30 minutes, then 0.64 ml (1.2 equivalents) of 1,4-dibromobutane was added, then the resultant mixture was agitated at room temperature for 3 hours.

The resultant compound was reacted, treated, and refined in the same way as in Example 1 to obtain the above-referenced compound in an amount of 428 mg (yield of 22%).

Example 23

Synthesis of 3-chloro-4,5-dihydro-4-(4-(4-(2-pyridyl)pyridinio-1-yl)butyl)-1,4-benzoxazepin-5-one chloride 200 mg of the compound of Example 16 was dissolved in 2 ml of acetone, 21 mg (2 equivalents) of sodium iodide and 120 mg (1.1 equivalents) of 2,4'-dipyridine were added, then the resultant mixture was heated and refluxed for 30 hours. This was allowed to cool, then the precipitated crystal was obtained by filtration and was recrystallized by a mixed solvent of methanol, acetone, and ether to obtain the above-referenced compound in an amount of 298 mg (yield of 96%);

Example 24

Synthesis of 3-chloro-4,5-dihydro-4-(4-(4-(2-pyrimidinyl)pyridinio-1-yl)butyl)-1,4-benzoxazepin-5-one chloride 500 mg of the compound of Example 16 was dissolved in 10 ml of acetone, 390 mg (1.5 equivalents) of sodium iodide and 330 mg (1.1 equivalents) of 4-(2-pyrimidinyl)pyridine were added, then the resultant mixture was heated and refluxed for 48 hours. This was allowed to cool, then the precipitated crystal was obtained by filtration and was recrystallized by acetone to obtain the above-referenced compound in an amount of 860 mg (yield of 100%).

Example 25

Synthesis of 4-(2-pyrimidinyl)-1,2,5,6-tetrahydropyridine (Part 1)

Step 1) Synthesis of N-t-butoxycarbonyl-4-hydroxy-4-(2-pyrimidinyl)pyridine 4.74 g of 2-tri-n-butyltinpyrimidine was dissolved in 30 ml of tetrahydrofuran (hereinafter abbreviated as THF), and 12 ml (1.5 equivalents) of 1.6N n-butyllithium/hexane solution was added dropwise under nitrogen gas at −78° C. After 30 minutes, 30 ml of a THF solution of 3.06 g (1.2 equivalents) of N-t-butoxycarbonyl-4-piperidone was added dropwise, and the reaction temperature was gradually raised to room temperature. Ice water was added to the reaction solution, and extraction was performed with ethyl acetate. The resultant mixture was washed by water and saturated saline, then was dried by anhydrous magnesium sulfate. The solvent was distilled off and the resultant crude product was refined with silica gel column chromatography (hexane:ethyl acetate=2:1) to obtain the above-referenced compound in an amount of 1.10 g (yield of 26%).

Step 2) Synthesis of N-t-butoxycarbonyl-4-(2-pyrimidinyl)-1,2,5,6-tetrahydropyridine 2.11 g of the compound of step 1 of Example 25 was dissolved in 30 ml of pyridine, then 1.0 ml (1.4 equivalents) of phosphorus oxychloride was added under ice cooling and the result was agitated for 15 hours. The pyridine was distilled off under reduced pressure, an aqueous solution of 10% sodium hydroxide was added and extraction was performed by methylene chloride. The organic layer was washed with saturated saline and was dried by anhydrous magnesium sulfate, then the solvent was distilled off and the resultant crude product was refined with silica gel column chromatography (hexane:ethyl acetate=2:1) to obtain the above-referenced compound in an amount of 1.01 g (yield of 51%).

Step 3) Synthesis of 4-(2-pyrimidinyl)-1,2,5,6-tetrahydropyridine 500 mg of the compound of step 2 of Example 25 was dissolved in 10 ml of methylene chloride, 3.5 ml of trifluoroacetic acid (hereinafter referred to as TFA) was added, then the resultant mixture was agitated at room temperature for 30 minutes. This was concentrated, then an aqueous solution of 10% sodium hydroxide was added and extraction was performed with chloroform. The organic layer was washed by saturated saline and was dried with anhydrous magnesium sulfate. This chloroform was concentrated to obtain the above-referenced compound in an amount of 260 mg (yield of 87%).

Example 26

Synthesis of 4-(2-pyrimidinyl)piperidine

Step 1) Synthesis of N-t-butoxycarbonyl-4-(2-pyrimidinyl)piperidine 490 mg of the compound of step 2 of Example 25 was dissolved in 10 ml of ethanol, 100 mg of 10% palladium carbon was added, then the resultant mixture was agitated under hydrogen gas for 2 days. The catalyst was filtered out, the ethanol was distilled off, and the residue was refined with silica gel column chromatography (hexane:ethyl acetate=1:1) to obtain the above-referenced compound in an amount of 160 mg (yield of 33%).

Step 2) Synthesis of 4-(2-pyrimidinyl)piperidine 1.5 g of the compound of step 1 of Example 26 was dissolved in 30 ml of methylene chloride, 10 ml of TFA was added, then the resultant mixture was agitated at room temperature for 30 minutes.

The same procedure was followed as in step 3 of Example 24 to obtain the above-referenced compound in an amount of 750 mg (yield of 82%).

Example 27

Synthesis of 4-(2-pyrimidinyl)-1,2,5,6-tetrahydropyridine (Part 2)

Step 1) Synthesis of 4-(2-pyrimidinyl)pyridine 35 mg (0.04 equivalents) of sodium was dissolved in 5 ml of methanol, then 4.0 g of 4-cyanopyridine was added. After 30 minutes, 2.0 g (1 equivalent) of ammonium chloride was added and the resultant mixture was agitated for 24 hours. The solution was concentrated to about half and 5 ml of acetone was added. The precipitated crystal was obtained by filtration to obtain the 4-amidinopyridine chlorate. This was dissolved in 2.2 ml (5 equivalents) of water, 5.0 ml (1.2 equivalents) of 1,1,3,3-tetramethoxypropane and 1,4-dioxane (2 ml) were added, and the resultant mixture was agitated at 130° C. for 1 hour and then dried to a solid. This was allowed to cool, then an aqueous solution of 10% sodium hydroxide was added and extraction was performed with ethyl acetate. This was washed with water and saturated saline, then was dried with anhydrous magnesium sulfate. The solvent was distilled off to obtain the above-referenced compound in an amount of 2.58 g (yield of 65%).

Step 2) Synthesis of 1-benzyl-4-(2-pyrimidinyl)-1,2,5,6-tetrahydropyridine 652 mg of the compound of Example 27 was dissolved in 10 ml of acetonitrile, 0.96 ml (2 equivalents) of benzyl chloride was added, then the resultant mixture was heated and refluxed for 20 hours. This was concentrated, then the residue was recrystallized by a mixed solvent of acetonitrile and ether to obtain a pyridinium salt. This was dissolved in ethanol (5 ml), then 307 mg (2 equivalents) of sodium borohydride was added. After 30 minutes, water was added and extraction was performed by ethyl acetate. The resultant mixture was washed with water and saturated saline, then was dried with anhydrous magnesium sulfate. The solvent was distilled off and the resultant crude product was refined with silica gel column chromatography (methylene chloride:methanol=30:1) to obtain the above-referenced compound in an amount of 968 mg (yield of 95%).

Step 3) Synthesis of 4-(2-primidinyl)-1,2,5,6-tetrahydropyridine 710 mg of the compound of step 2 of Example 27 was dissolved in 10 ml of dichloromethane, 0.31 ml (1 equivalent) of chlorocarbonic acid-1-chloroethyl was added, then the resultant mixture was heated and refluxed for 1 hour. This was concentrated once, then methanol was added again, then the resultant mixture was heated and refluxed for 1 hour. This was concentrated, then recrystallized with a mixed solvent of methanol and ether to obtain the chlorate of the above-referenced compound in an amount of 471 mg (yield of 84%).

Example 28

Synthesis of 4-(4-methylpyrimidin-2-yl)-1,2,5,6-tetrahydropyridine

Step 1) Synthesis of 1-benzyl-4-(4-methylpyrimidin-2-yl)-1,2,5,6-tetrahydropyridine 274 mg of 4-(4-methylpyrimidin-2-yl)pyridine was dissolved in 5 ml of acetonitrile, 0.40 ml (2 equivalents) of benzyl chloride was added, then the resultant mixture was heated and refluxed for 10 hours. This was concentrated, then the residue was recrystallized with a mixed solvent of acetonitrile and ether to obtain a pyridinium salt. This was dissolved in ethanol (3 ml), and 129 mg (2 equivalents) of sodium borohydride was added. After 30 minutes, water was added and extraction was performed with ethyl acetate.

The resultant mixture was reacted, treated, and refined in the same way as in step 2 of Example 27 to obtain the above-referenced compound in an amount of 409 mg (yield of 94%).

Step 2) Synthesis of 4-(4-methylpyrimidin-2-yl)-1,2,5,6-tetrahydropyridine 300 mg of the compound of step 1 of Example 28 was dissolved in 5 ml of dichloromethane, 0.14 ml (1 equivalent) of chlorocarbonic acid-1-chloroethyl was added, then the resultant mixture was heated and refluxed for 1 hour. This was concentrated once, then methanol was added again, then the resultant mixture was heated and refluxed for 1 hour. This was concentrated, then recrystallized with a mixed solvent of methanol and ether to obtain the chlorate of the above-referenced compound in an amount of 213 mg (yield of 88%).

Example 29

Synthesis of 3-(2-pyrimidinyl)-1,2,5,6-tetrahydropyridine

Step 1) Synthesis of N-t-butoxycarbonyl-3-hydroxy-3-(2-pyrimidinyl)piperidine 5.0 g of 2-tri-n-butyltinpyrimidine was dissolved in 60 ml of THF, and 12 ml (1.5 equivalents) of 1.7N n-butyllithium/hexane solution was added dropwise at −78° C. under nitrogen gas. After 1 hour, 30 ml of a THF solution of 3.24 g (1.2 equivalents) of N-t-butoxycarbonyl-3-piperidone was added dropwise, and the reaction temperature was gradually raised to room temperature. A saturated aqueous solution of ammonium chloride was added to the reaction solution, and extraction was performed with ethyl acetate. The resultant mixture was washed by water and saturated saline, then was dried with anhydrous magnesium sulfate. The solvent was distilled off and the resultant crude product was refined with silica gel column chromatography (methylene chloride:methanol=20:1), to obtain the above-referenced compound in an amount of 1.10 g (yield of 29%).

Step 2) Synthesis of N-t-butoxycarbonyl-3-(2-pyrimidinyl)-1,2,5,6-tetrahydropyridine 1.56 g of the compound of step 1 of Example 29 was dissolved in 15 ml of pyridine, 0.8 ml (1.5 equivalents) of phosphorus oxychloride was added under ice cooling and the result was agitated for 16 hours.

The resultant mixture was reacted, treated, and refined in the same way as in step 2 of Example 25 to obtain the above-referenced compound in an amount of 285 mg (yield of 20%).

Step 3) Synthesis of 3-(2-pyrimidinyl)-1,2,5,6-tetrahydropyridine 260 mg of the compound of step 2 of Example 29 was dissolved in 5 ml of methylene chloride, 2 ml of TFA was added, then the resultant mixture was agitated at room temperature for 30 minutes.

The resultant mixture was reacted, treated, and refined in the same way as in step 3 of Example 25 to obtain the above-referenced compound in an amount of 146 mg (yield of 91%).

Example 30

Synthesis of 3-(2-pyrimidinyl)piperidine

Step 1) Synthesis of N-t-butoxycarbonyl-3-(2-pyrimidinyl)piperidine 490 mg of the compound of step 2 of Example 29 was dissolved in 10 ml of ethanol, 40 mg of 10% palladium carbon was added, and the resultant mixture was agitated under hydrogen gas for 15 hours.

The resultant mixture was reacted, treated, and refined in the same way as in step 1 of Example 26 to obtain the above-referenced compound in an amount of 100 mg (yield of 50%).

Step 2) Synthesis of 3-(2-pyrimidinyl)piperidine 140 mg of the compound of step 1 of Example 30 was dissolved in 5 ml of methylene chloride, 2 ml of TFA was added, then the resultant mixture was agitated at room temperature for 30 minutes.

The same procedure was followed as in step 3 of Example 29 to obtain the above-referenced compound in an amount of 70 mg (yield of 81%).

Example 31

Synthesis of 7-chloro-4,5-dihydro-4-(2-(4-(2-pyrimidinyl)piperazin-1-yl)ethyl)-1,4-benzoxazepin-5-one 14 mg of the compound of Example 1 was dissolved in 5 ml of dimethylformamide, 13 mg (1.5 equivalents) of 1-(2-pyrimidinyl)piperazine, 16 mg (2 equivalents) of sodium iodide, and 11 mg (2 equivalents) of triethylamine. were added, and the resultant mixture was agitated at 90° C. for 10 hours. This was allowed to cool, then water was added and extraction was performed twice with ethyl acetate. The entire organic layer was washed with an aqueous solution of sodium hydrogencarbonate, water, and saturated saline, then was dried with anhydrous magnesium sulfate. The solvent was distilled off and the resultant crude product was refined with silica gel column chromatography (methylene chloride:methanol=30:1) to obtain the above-referenced compound in an amount of 14 mg (yield of 67%). Note that the fumarate can be obtained by an ordinary method, then making it into an amorphous powder.

Example 32

Synthesis of 4,5-dihydro-4-(4-(4-(2-pyridyl)piperazin-1-yl)butyl)-1,4-benzoxazepin-5-one 180 mg of the compound of Example 2 was dissolved in 10 ml of dioxane, 149 mg (1.5 equivalents) of 1-(2-pyridyl)piperazine and 123 mg (2 equivalents) of triethylamine were added, then the resultant mixture was heated and refluxed for 10 hours. Next, the dioxane was distilled off, a saturated aqueous solution of sodium hydrogencarbonate was added, and extraction was performed with methylene chloride. This was washed with a saturated aqueous solution of sodium hydrogencarbonate, water, and saturated saline, then was dried with anhydrous magnesium sulfate.

This was then refined in the same way as in Example 31 to obtain the above-referenced compound in an amount of 140 mg (yield of 61%). Note that the fumarate can be obtained by an ordinary method, then recrystallizing it with a mixed solvent of methylene chloride, ether, and hexane.

Example 33

Synthesis of 4,5-dihydro-8-methoxy-4-(4-(4-(2-pyrimidinyl)piperazin-1-yl)butyl)-1,4-benzoxazepin-5-one 196 mg of the compound of Example 4 was dissolved in 10 ml of acetonitrile, 148 mg (1.5 equivalents) of 1-(2-pyrimidinyl)piperazine and 234 mg (2 equivalents) of triethylamine were added, then the resultant mixture was heated and refluxed for 3 hours. Next, the acetonitrile was distilled off, then this was treated and refined in the same way as in Example 31 to obtain the above-referenced compound in an amount of 237 mg (yield of 97%). Note that the fumarate can be obtained with an ordinary method, then recrystallizing it with a mixed solvent of methanol and ether.

Example 34

Synthesis of 4,5-dihydro-3-methyl-4-(4-(4-(2-pyrimidinyl)piperazin-1-yl)butyl)-1,4-benzoxazepin-5-one 110 mg of the compound of Example 8 was dissolved in 10 ml of dioxane, 87 mg (1.5 equivalents) of 1-(2-pyrimidinyl)piperazine and 72 mg (2 equivalents) of triethylamine were added, then the resultant mixture was heated and refluxed for 8 hours.

This was then treated and refined in the same way as in Example 32 to obtain the above-referenced compound in an amount of 81 mg (yield of 58%). Note that the fumarate can be obtained by an ordinary method, then recrystallizing it with a mixed solvent of methylene chloride and ether.

Example 35

Synthesis of 4-(4-(4-(2-chloropyridin-6-yl)piperazin-1-yl)butyl)-4,5-dihydro-3-methyl-1,4-benzoxazepin-5-one 188 mg of the compound of Example 8 was dissolved in 8 ml of dioxane, 100 mg (0.83 equivalents) of 1-(2-chloropyridin-6-yl)piperazine and 0.11 ml (1.5 equivalents) of triethylamine were added, then the resultant mixture was heated and refluxed for 13 hours.

This was then treated and refined in the same way as in Example 32 to obtain the above-referenced compound in an amount of 140 mg (yield of 67%). Note that the fumarate can be obtained by an ordinary method, then recrystallizing it with a mixed solvent of acetone and ether.

Example 36

Synthesis of 4,5-dihydro-3-ethyl-4-(4-(4-(2-pyridyl)piperazin-1-yl)butyl)-1,4-benzoxazepin-5-one 128 mg of the compound of Example 10 was dissolved in 10 ml of dimethylformamide, 112 mg (1.5 equivalents) of 1-(2-pyridyl)piperazine, 137 mg (2 equivalents) of sodium iodide, and 93 mg (2 equivalents) of triethylamine were added, and the resultant mixture was agitated at 90° C. for 6 hours.

This was then treated and refined in the same way as in Example 31 to obtain the above-referenced compound in an amount of 185 mg (yield of 99%). Note that the fumarate can be obtained by an ordinary method, then making it into an amorphous powder.

Example 37

Synthesis of 4,5-dihydro-3,8-dimethyl-4-4-(4-(3-methylphenyl)piperazin-1-yl)butyl)-1,4-benzoxazepin-5-one 250 mg of the compound of Example 11 was dissolved in 5 ml of acetonitrile, 340 mg (1.5 equivalents) of 1-(3-methylphenyl)piperazine succinate, and 390 mg (5 equivalents) of triethylamine were added, then the resultant mixture was heated and refluxed for 2 hours.

This was then treated and refined in the same way as in Example 32 to obtain the above-referenced compound in an amount of 297 mg (yield of 92%). Note that the fumarate can be obtained by an ordinary method, then recrystallizing it with a mixed solvent of methanol and ether.

Example 38

Synthesis of 4,5-dihydro-3,8-dimethyl-4-(4-(4-(2-methoxyphenyl)piperazin-1-yl)butyl)-1,4-benzoxazepin-5-one 250 mg of the compound of Example 11 was dissolved in 5 ml of acetonitrile, 223 mg (1.5 equivalents) of 1-(2-methoxyphenyl)piperazine and 156 mg (2 equivalents) of triethylamine were added, then the resultant mixture was heated and refluxed for 3 hours.

This was then treated and refined in the same way as in Example 32 to obtain the above-referenced compound in an amount of 312 mg (yield of 93%). Note that the fumarate can be obtained by an ordinary method, then recrystallizing it with a mixed solvent of methanol, ether, and hexane.

Example 39

Synthesis of 4,5-dihydro-3,7-dimethyl-4-(4-(4-(2-methoxypyridin-6-yl)piperazin-1-yl)butyl)-1,4-benzoxazepin-5-one 100 mg of the compound of Example 12 was dissolved in 7 ml of dimethylformamide, 108 mg (1.2 equivalents) of 1-(2-methoxypyridin-6-yl)piperazine and 70 mg (1.5 equivalents) of triethylamine were added, and the resultant mixture was agitated at 90° C. for 30 hours.

This was then treated and refined in the same way as in Example 31 to obtain the above-referenced compound in an amount of 110 mg (yield of 54%). Note that the fumarate can be obtained by an ordinary method, then recrystallizing it with a mixed solvent of methanol and ether.

Example 40

Synthesis of 4-(4-(4-(4-amino-5-fluoropyrimidin-2-yl)piperazin-1-yl)butyl)-4,5-dihydro-3,7-dimethyl-1,4-benzoxazepin-5-one 396 mg of the compound of Example 12 was dissolved in 3 ml of dimethylformamide, 289 mg (1.2 equivalents) of 1-(4-amino-5-fluoropyrimidin-2-yl)piperazine and 185 mg (1.5 equivalents) of triethylamine were added, and the resultant mixture was agitated at 90° C. for 30 hours.

This was then treated and refined in the same way as in Example 31 to obtain the above-referenced compound in an amount of 372 mg (yield of 69%). Note that the chlorate can be obtained by making the hydrochloride by an ordinary method, then recrystallizing it with a mixed solvent of methanol and ether.

Example 41

Synthesis of 4-(4-(4-(2-chloropyridin-6-yl)piperazin-1-yl)butyl)-4,5-dihydro-7-fluoro-3-methyl-1,4-benzoxazenin-5-one 190 mg of the compound of Example 13 was dissolved in 10 ml of dimethylformamide, 172 mg (1.5 equivalents) of 1-(2-chloropyridin-6-yl)piperazine and 117 mg (2 equivalents) of triethylamine were added, and the resultant mixture was agitated at 90° C. for 5 hours.

This was then treated and refined in the same way as in Example 31 to obtain the above-referenced compound in an amount of 242 mg (yield of 94%). Note that the fumarate can be obtained by an ordinary method, then recrystallizing it with a mixed solvent of methanol and ether.

Example 42

Synthesis of 4,5-dihydro-7-fluoro-3-methyl-4-(4-(4-(3-methylphenyl)piperazin-1-yl)butyl)-1,4-benzoxazepin-5-one 210 mg of the compound of Example 13 was dissolved in 10 ml of dimethylformamide, 239 mg (1.5 equivalents) of N-(m-tolyl)piperazine bichlorate and 259 mg (4 equivalents) of triethylamine were added, and the resultant mixture was agitated at 90° C. for 7 hours.

This was then treated and refined in the same way as in Example 31 to obtain the above-referenced compound in an amount of 187 mg (yield of 69%). Note that the fumarate can be obtained by an ordinary method, then recrystallizing it with a mixed solvent of methanol and ether.

Example 43

Synthesis of 4,5-dihydro-3,7-dimethyl-4-(5-(4-phenylpiperazin-1-yl)pentyl)-1,4-benzoxazepin-5-one 150 mg of the compound of Example 14 was dissolved in 2 ml of dimethylformamide, 108 mg (1.5 equivalents) of N-phenylpiperazine and 89 mg (2 equivalents) of triethylamine were added, and the resultant mixture was agitated at 90° C. for 6 hours.

This was then treated and refined in the same way as in Example31 to obtain the above-referenced compound in an amount of 108 mg (yield of 59%). Note that the fumarate can be obtained by an ordinary method, then recrystallizing it with a mixed solvent of methanol, chloroform, and ether.

Example 44

Synthesis of 4,5-dihydro-3,7-dimethyl-4-(5-(4-(2-pyrimidinyl)piperazin-1-yl)pentyl)-1,4-benzoxazepin-5-one 130 mg of the compound of Example 14 was dissolved in 2 ml of dimethylformamide, 95 mg (1.5 equivalents) of 1-(2-pyrimidinyl)piperazine and 77 mg (2 equivalents) of triethylamine were added, and the resultant mixture was agitated at 90° C. for 5 hours.

This was then treated and refined in the same way as in Example 31 to obtain the above-referenced compound in an amount of 107 mg (yield of 67%). Note that the fumarate can be obtained by an ordinary method, then recrystallizing it with a mixed solvent of methanol, chloroform, and ether.

Example 45

Synthesis of 3-chloro-4,5-dihydro-4-(3-(4-(2-pyrimidinyl)piperazin-1-yl)propyl)-1,4-benzoxazepin-5-one 200 mg of the compound of Example 15 was dissolved in 6 ml of dimethylformamide, 180 mg (1.5 equivalents) of 1-(2-pyrimidinyl)piperazine, 220 mg (2 equivalents) of sodium iodide and 0.21 ml (2 equivalents) of triethylamine were added, and the resultant mixture was agitated at 80° C. for 15 hours.

This was then treated and refined in the same way as in Example 31 to obtain the above-referenced compound in an amount of 140 mg (yield of 48%). Note that the chlorate can be obtained by making the hydrochloride by an ordinary method, then recrystallizing it with a mixed solvent of methanol and ether.

Example 46

Synthesis of 3-chloro-4,5-dihydro-4-(4-(4-(2-pyridyl)piperazin-1-yl)butyl)-1,4-benzoxazepin-5-one 287 mg of the compound of Example 16 was dissolved in 9 ml of dimethylformamide, 0.24 ml (1.6 equivalents) of 1-(2-pyridyl)piperazine, 300 mg (2 equivalents) of sodium iodide, and 0.29 ml (2 equivalents) of triethylamine were added, and the resultant mixture was agitated at 80° C. for 14 hours.

This was then treated and refined in the same way as in Example 31 to obtain the above-referenced compound in an amount of 167 mg (yield of 41%). Note that the fumarate can be obtained by an ordinary method, then recrystallizing it with a mixed solvent of ethanol and diisopropylether.

Example 47

Synthesis of 3-chloro-4,5-dihydro-4-(4-(4-(4-quinazolyl)piperazin-1-yl)butyl)-1,4-benzoxazepin-5-one 429 mg (1.5 equivalents) of the compound of Example 16 was dissolved in 10 ml of dimethylformamide, 214 mg of 1-(4-quinazolyl)piperazine, 300 mg (2 equivalents) of sodium iodide, and 0.28 ml (2 equivalents) of triethylamine were added, and the resultant mixture was agitated at 80° C. for 15 hours.

This was then treated and refined in the same way as in Example 31 to obtain the above-referenced compound in an amount of 380 mg (yield of 83%). Note that the hydrochloride can be obtained by making the chlorate by an ordinary method, then recrystallizing it with acetone.

Example 48

Synthesis of 3,8-dichloro-4,5-dihydro-4-(4-(4-(2-pyridyl)piperazin-1-yl)butyl)-1,4-benzoxazepin-5-one 169 mg of the compound of Example 17 was dissolved in 3 ml of dimethylformamide, 129 mg (1.5 equivalents) of 1-(2-pyridyl)piperazine, 158 mg (2 equivalents) of sodium iodide, and 106 mg (2 equivalents) of triethylamine were added, and the resultant mixture was agitated at 80° C. for 6 hours.

This was then treated and refined in the same way as in Example 31 to obtain the above-referenced compound in an amount of 219 mg (yield of 93%). Note that the bichlorate can be obtained by making the dihydrochloride by an ordinary method, then recrystallizing it with a mixed solvent of methanol, chloroform, and ether.

Example 49

Synthesis of 3-chloro-4,5-dihydro-7-methyl-4-(4-(4-(2-pyrimidinyl)-piperazin-1-yl)butyl)-1,4-benzoxazepin-5-one 129 mg of the compound of Example 19 was dissolved in 2 ml of dimethylformamide, 106 mg (1.5 equivalents) of 1-(2-pyrimidinyl)piperazine, 129 mg (2 equivalents) of sodium iodide, and 87 mg (2 equivalents) of triethylamine were added, and the resultant mixture was agitated at 90° C. for 7 hours.

This was then treated and refined in the same way as in Example 31 to obtain the above-referenced compound in an amount of 152 mg (yield of 83%). Note that the bichlorate can be obtained by making the dihydrochloride by an ordinary method, then recrystallizing it with ether.

Example 50

Synthesis of 3-chloromethyl-4,5-dihydro-7-methoxy-4-(4-(4-(2-pyrimidinyl)piperazin-1-yl)butyl)-1,4-benzoxazepin-5-one 500 mg of the compound of Example 21 was dissolved in 15 ml of dimethylformamide, 260 mg (1.2 equivalents) of 1-(2-pyrimidinyl)piperazine, and 0.28 ml (1.5 equivalents) of triethylamine were added, and the resultant mixture was agitated at 40° C. for 8 hours.

This was then treated and refined in the same way as in Example 31 to obtain the above-referenced compound in an amount of 210 mg (yield of 98%). Note that the fumarate can be obtained by an ordinary method, then recrystallizing it with a mixed solvent of acetone and ether.

Example 51

Synthesis of 4,5-dihydro-3-methoxymethyl-4-(4-(4-(2-pyrimidinyl)piperazin-1-yl)butyl)-1,4-benzoxazepin-5-one 172 mg of the compound of Example 22 was dissolved in 5 ml of dioxane, 250 mg (3 equivalents) of 1-(2-pyrimidinyl)piperazine and 0.10 ml (1.5 equivalents) of triethylamine were added, and the resultant mixture was agitated at 120° C. for 4 hours.

This was then treated and refined in the same way as in Example 31 to obtain the above-referenced compound in an amount of 210 mg (yield of 98%). Note that the fumarate can be obtained by an ordinary method, then recrystallizing it with a mixed solvent of acetone and ether.

Example 52

Synthesis of 4,5-dihydro-3-methoxymethyl-4-(4-(4-(2-pyridyl)piperazin-1-yl)butyl)-1,4-benzoxazepin-5-one 146 mg of the compound of Example 22 was dissolved in 5 ml of dioxane, 0.20 ml (3 equivalents) of 1-(2-pyridyl)piperazine and 0.09 ml (1.5 equivalents) of triethylamine were added, and the resultant mixture was agitated at 120° C. for 4 hours.

This was then treated and refined in the same way as in Example 31 to obtain the above-referenced compound in an amount of 168 mg (yield of 93%). Note that the fumarate can be obtained by an ordinary method, then recrystallizing it with a mixed solvent of acetone and ether.

Example 53

Synthesis of 4,5-dihydro-3-methyl-4-(4-(4-(2-pyrimidinyl)-1,2,5,6-tetrahydropyridin-1-yl)butyl)-1,4-benzoxazepin-5-one 120 mg of the compound of Example 25 was dissolved in 10 ml of dioxane, 276 mg (1.2 equivalents) of the compound of Example 8 and 0.16 ml (1.5 equivalents) of triethylamine were added, and the resultant mixture was agitated at 120° C. for 9 hours.

This was then treated and refined in the same way as in Example 31 to obtain the above-referenced compound in an amount of 230 mg (yield of 79%). Note that the fumarate can be obtained by an ordinary method, then recrystallizing it with a mixed solvent of acetone and ether.

Example 54

Synthesis of 4,5-dihydro-3-methyl-4-(4-(4-(2-pyrimidinyl)piperidin-1-yl)butyl)-1,4-benzoxazepin-5-one 65 mg of the compound of Example 26 was dissolved in 10 ml of dioxane, 148 mg (1.2 equivalents) of the compound of example 8 and 0.08 ml (1.5 equivalents) of triethylamine were added, and the resultant mixture was agitated at 120° C. for 17 hours.

This was then treated and refined in the same way as in Example 31 to obtain the above-referenced compound in an amount of 130 mg (yield of 72%). Note that the fumarate can be obtained by an ordinary method, then recrystallizing it with a mixed solvent of acetone and ether.

Example 55

Synthesis of 4,5-dihydro-7-fluoro-3-methyl-4-(4-(4-(2-pyrimidinyl)-1,2,5,6-tetrahydropyridin-1-yl)butyl)-1,4-benzoxazepin-5-one 159 mg of the compound of Example 25 was dissolved in 4 ml of acetonitrile, 279 mg (0.9 equivalent) of the compound of Example 13 and 0.19 ml (1.5 equivalents) of triethylamine were added, then the resultant mixture was heated and refluxed for 4 hours.

This was then treated and refined in the same way as in Example 31 to obtain the above-referenced compound in an amount of 289 mg (yield of 82%). Note that the fumarate can be obtained by an ordinary method, then recrystallizing it with a mixed solvent of methanol and ether.

Example 56

Synthesis of 3-chloro-4,5-dihydro-4-(4-(4-(2-pyrimidinyl)-1,2,5,6-tetrahydropyridin-1-yl)butyl)-1,4-benzoxazepin-5-one 128 mg of the compound of Example 25 was dissolved, in 10 ml of DMF, 335 mg (1.5 equivalents) of the compound of Example 16, 238 mg (2 equivalents) of sodium iodide, and 0.22 ml (2 equivalents) of triethylamine were added, and the resultant mixture was agitated at 80° C. for 14 hours.

This was then treated and refined in the same way as: in Example 31 to obtain the above-referenced compound in an amount of 86 mg (yield of 26%). Note that the hydrochloride can be obtained by making the chlorate by an ordinary method, then recrystallizing it with a mixed solvent of methanol and acetone.

Example 57

Synthesis of 3-chloro-4,5-dihydro-4-(4-(4-(2-pyrimidinyl)piperidin-1-yl)butyl)-1,4-benzoxazepin-5-one 46 mg of the compound of Example 26 was dissolved in 5 ml of DMF, 120 mg (1.5 equivalents) of the compound of Example 16, 84 mg (2 equivalents) of sodium iodide, and 0.08 ml (2 equivalents) of triethylamine were added, and the resultant mixture was agitated at 80° C. for 12 hours.

This was then treated and refined in the same way as in Example 31 to obtain the above-referenced compound in an amount of 98 mg (yield of 84%). Note that the hydrochloride can be obtained by making the chlorate by an ordinary method, then recrystallizing it with acetone.

Example 58

Synthesis of 3-chloro-4,5-dihydro-4-(4-(3-(2-pyrimidinyl)-1,2,5,6-tetrahydropyridin-1-yl)butyl)-1,4-benzoxazepin-5-one 70 mg of the compound of Example 29 was dissolved in 8 ml of DMF, 150 mg (1.2 equivalents) of the compound of Example 16, 156 mg (2.4 equivalents) of sodium iodide, and 0.15 ml (2.4 equivalents) of triethylamine were added, and the resultant mixture was agitated at 80° C. for 13 hours.

This was then treated and refined in the same way as in Example 31 to obtain the above-referenced compound in an amount of 36 mg (yield of 20%). Note that the fumarate can be obtained by an ordinary method, then recrystallizing it with acetone.

Example 59

Synthesis of 3,8-dichloro-4,5-dihydro-4-(4-(4-(2-pyrimidinyl)-1,2,5,6-tetrahydropyridin-1-yl)butyl)-1,4-benzoxazepin-5-one 50 mg of the compound of Example 26 was dissolved in 5 ml of DMF, 66 mg (1.5 equivalents) of the compound of Example 17, 62 mg (2 equivalents) of sodium iodide, and 42 mg (2 equivalents) of triethylamine were added, and the resultant mixture was agitated at 90° C. for 6 hours.

This was then treated and refined in the same way as, in Example 31 to obtain the above-referenced compound in an amount of 39 mg (yield of 43%). Note that the fumarate can be obtained by an ordinary method, then recrystallizing it with a mixed solvent of methanol and ether.

Example 60

Synthesis of 3,8-dichloro-4,5-dihydro-4-(4-(4-(2-pyrimidinyl)piperidin-1-yl)butyl)-1,4-benzoxazepin-5-one 70 mg of the compound of Example 26 was dissolved in 5 ml of DMF, 206 mg (1.5 equivalents) of the compound of Example 17, 145 mg (2.3 equivalents) of sodium iodide, and 97 mg (2.3 equivalents) of triethylamine were added, and the resultant mixture was agitated at 90° C. for 6 hours.

This was then treated and refined in the same way as in Example 31 to obtain the above-referenced compound in an amount of 177 mg (yield of 92%): Note that the fumarate can be obtained by an ordinary method, then recrystallizing it with ether.

Example 61

Synthesis of 3-chloro-4,5-dihydro-8-methoxy-4-(4-(4-(2-pyrimdinyl)-1,2,5,6-tetrahydropyridin-1-yl)butyl)-1,4-benzoxazepin-5-one 70 mg of the compound of Example 25 was dissolved in 6 ml of DMF, 150 mg (1.1 equivalents) of the compound of Example 18, 142 mg (2.2 equivalents) of sodium iodide, and 0.13 ml (2.2 equivalents) of triethylamine were added, and the resultant mixture was agitated at 80° C. for 14 hours.

This was then treated and refined in the same way as in Example 31 to obtain the above-referenced compound in an amount of 60 mg (yield of 32%). Note that the fumarate can be obtained by an ordinary method, then recrystallizing it with ether.

Example 62

Synthesis of 3-chloro-4,5-dihydro-8-methoxy-4-(4-(4-(2-pyrimidinyl)piperidin-1-yl)butyl)-1,4-benzoxazepin-5-one 70 mg of the compound of Example 26 was dissolved in 6 ml of DMF, 150 mg (1.1 equivalents) of the compound of Example 18, 142 mg (2.2 equivalents) of sodium iodide, and 0.13 ml (2.2 equivalents) of triethylamine were added, and the resultant mixture was agitated at 80° C. for 15 hours.

This was then treated and refined in the same way as in Example 31 to obtain the above-referenced compound in an amount of 177 mg (yield of 92%). Note that the fumarate can be obtained by an ordinary method, then recrystallizing it with acetone and ether.

Example 63

Synthesis of 4,5-dihydro-3-methyl-4-(3-(4-(2-pyridyl)-1,2,5,6-tetrahydropyridin-1-yl)propyl)-1,4-benzoxazepin-5-one 150 mg of the compound of Example 7 was dissolved in 6 ml of DMF, 115 mg (1.2 equivalents) of 4-(2-pyridyl)-1,2,5,6-tetrahydropyridine, 179 mg (2 equivalents) of sodium iodide, and 0.17 ml (2 equivalents) of triethylamine were added, and the resultant mixture was agitated at 90° C. for 20 hours.

This was then treated and refined in the same way as in Example 31 to obtain the above-referenced compound in an amount of 130 mg (yield of 59%). Note that the fumarate can be obtained by an ordinary method, then recrystallizing it with a mixed solvent of acetone and ether.

Example 64

Synthesis of 4,5-dihydro-3-methyl-4-(5-(4-(2-pyridyl)-1,2,5,6-tetrahydropyridin-1-yl)pentyl)-1,4-benzoxazepin-5-one 200 mg of the compound of Example 9 was dissolved in 5 ml of acetonitrile, 118 mg (1.2 equivalents) of 4-(2-pyridyl)-1,2,5,6-tetrahydropyridine and 0.17 ml (2 equivalents) of triethylamine were added, then the resultant mixture was heated and refluxed for 10 hours.

This was then treated and refined in the same way as in Example 31 to obtain the above-referenced compound in an amount of 74 mg (yield of 31%). Note that the fumarate can be obtained by an ordinary method, then making it into an amorphous powder.

Example 65

Synthesis of 4,5-dihydro-3-methyl-4-(3-(4-(2-pyridyl)piperidin-1-yl)propyl)-1,4-benzoxazepin-5-one 200 mg of the compound of Example 7 was dissolved in 6 ml of DMF, 177 mg (1.1 equivalents) of 4-(2-pyridyl) piperidine chlorate, 238 mg (2 equivalents) of sodium iodide, and 0.39 ml (3.5 equivalents) of triethylamine were added, and the resultant mixture was agitated at 90° C. for 20 hours.

This was then treated and refined in the same way as in Example 31 to obtain the above-referenced compound in an amount of 90 mg (yield of 31%). Note that the fumarate can be obtained by an ordinary method, then making it into an amorphous powder.

Example 66

Synthesis of 3,8-dichloro-4,5-dihydro-4-(4-(4-(2-pyridyl)-1,2,5,6-tetrahydropyridin-1-yl)butyl)-1,4-benzoxazepin-5-one 200 mg of the compound of Example 17 was dissolved in 5 ml of DMF, 120 mg (1.2 equivalents) of 4-(2-pyridyl)-1,2,5,6-tetrahydropyridine, 187 mg (2 equivalents) of sodium iodide, and 0.17 ml (2 equivalents) of triethylamine were added, and the resultant mixture was agitated at 90° C. for 18 hours.

This was then treated and refined in the same way as in Example 31 to obtain the above-referenced compound in an amount of 117 mg (yield of 43%). Note that the fumarate can be obtained by an ordinary method, then recrystallizing it with a mixed solvent of methanol and ether.

Example 67

Synthesis of 3,8-dichloro-4,5-dihydro-4-(4-(4-(2-pyridyl)piperidin-1-yl)butyl)-1,4-benzoxazepin-5-one 200 mg of the compound of Example 17 was dissolved in 5 ml of DMF, 149 mg (1.2 equivalents) of 4-(2-pyridyl) piperidine chlorate, 187 mg (2 equivalents) of sodium iodide, and 0.30 ml (3.5 equivalents) of triethylamine were added, and the resultant mixture was agitated at 90° C. for 20 hours.

This was then treated and refined in the same way as in Example 31 to obtain the above-referenced compound in an amount of 158 mg (yield of 59%). Note that the fumarate can be obtained by an ordinary method, then recrystallizing it with a mixed solvent of methanol and ether.

Example 68

Synthesis of 3-chloro-4,5-dihydro-4-(3-(4-(2-pyridyl)-1,2,5,6-tetrahydropyridin-1-yl)propyl)-1,4-benzoxazepin-5-one 200 mg of the compound of Example 15 was dissolved in 5 ml of DMF, 141 mg (1.2 equivalents) of 4-(2-pyridyl)-1,2,5,6-tetrahydropyridine, 220 mg (2 equivalents) of sodium iodide, and 0.21 ml (2 equivalents) of triethylamine were added, and the resultant mixture was agitated at 90° C. for 18 hours.

This was then treated and refined in the same way as in Example 31 to obtain the above-referenced compound in an amount of 150 mg (yield of 52%). Note that the fumarate can be obtained by an ordinary method, then recrystallizing it with a mixed solvent of methanol and ether.

Example 69

Synthesis of 3-chloro-4,5-dihydro-4-(3-(4-(2-pyridyl)piperidin-1-yl)propyl)-1,4-benzoxazepin-5-one 200 mg of the compound of Example 15 was dissolved in 5 ml of DMF, 175 mg (1.2 equivalents) of 4-(2-pyridyl)

piperidine chlorate, 2.20 mg (2 equivalents) of sodium iodide, and 0.36 ml (3.5 equivalents) of triethylamine were added, and the resultant mixture was agitated at 90° C. for 20 hours.

This was then treated and refined in the same way as in Example 31 to obtain the above-referenced compound in an amount of 160 mg (yield of 55%). Note that the fumarate can be obtained by an ordinary method, then making it into an amorphous powder.

Example 70

Synthesis of 3-chloro-4,5-dihydro-4-(5-(4-(2-pyridyl)-1,2,5,6-tetrahydropyridin-1-yl)pentyl)-1,4-benzoxazepin-5-one 250 mg of the compound of Example 20 was dissolved in 5 ml of acetonitrile, 139 mg (1.2 equivalents) of 4-(2-pyridyl)-1,2,5,6-tetrahydropyridine and 0.20 ml (2 equivalents) of triethylamine were added, then the resultant mixture was heated and refluxed for 8 hours.

This was then treated and refined in the same way as in Example 31 to obtain the above-referenced compound in an amount of 110 mg (yield of 37%). Note that the fumarate can be obtained by an ordinary method, then recrystallizing it with a mixed solvent of methanol and ether.

Example 71

Synthesis of 4,5-dihydro-4-(4-(4-(2-pyridyl)-1,2,5,6-tetrahydropyridin-1-yl)butyl)-1,4-benzoxazepin-5-one 200 mg of the compound of Example 2 was dissolved in 5 ml of acetonitrile, 130 mg (1.2 equivalents) of 4-(2-pyridyl)-1,2,5,6-tetrahydropyridine and 0.19 ml (2 equivalents) of triethylamine were added, then the resultant mixture was heated and refluxed for 8 hours.

This was then treated and refined in the same way as in Example 31 to obtain the above-referenced compound in an amount of 215 mg (yield of 86%). Note that the fumarate can be obtained by an ordinary method, then making it into an amorphous powder.

Example 72

Synthesis of 4,5-dihydro-4-(4-(4-(2-pyridyl)piperidin-1-yl)butyl)-1,4-benzoxazepin-5-one 200 mg of the compound of Example 2 was dissolved in 5 ml of acetonitrile, 140 mg (1 equivalents) of 4-(2-pyridyl)piperidine chlorate and 0.33 ml (3.5 equivalents) of triethylamine were added, then the resultant mixture was heated and refluxed for 10 hours.

This was then treated and refined in the same way as in Example 31 to obtain the above-referenced compound in an amount of 96 mg (yield of 38%). Note that the fumarate can be obtained by an ordinary method, then recrystallizing it with a mixed solvent of methanol and ether.

Example 73

Synthesis of 4,5-dihydro-4-(5-(4-(2-pyridyl)-1,2,5,6-tetrahydropyridin-1-yl)pentyl)-1,4-benzoxazepin-5-one 200 mg of the compound of Example 6 was dissolved in 5 ml of acetonitrile, 124 mg (1.2 equivalents) of 4-(2-pyridyl)-1,2,5,6-tetrahydropyridine and 0.18 ml (2 equivalents) of triethylamine were added, then the resultant mixture was heated and refluxed for 8 hours.

This was then treated and refined in the same way as in Example 31 to obtain the above-referenced compound in an amount of 230 mg (yield of 92%). Note that the fumarate can be obtained by an ordinary method, then making it into an amorphous powder.

Example 74

Synthesis of 4,5-dihydro-3,7-dimethyl-4-(4-(4-(2-pyridyl)-1,2,5,6-tetrahydropyridin-1-yl)butyl)-1,4-benzoxazepin-5-one 200 mg of the compound of Example 12 was dissolved in 5 ml of acetonitrile, 120 mg (1.2 equivalents) of 4-(2-pyridyl)-1,2,5,6-tetrahydropyridine and 0.17 ml (2 equivalents) of triethylamine were added, then the resultant mixture was heated and refluxed for 8 hours.

This mixture was then treated and refined in the same way as in Example 31 to obtain the above-referenced compound in an amount of 197 mg (yield of 79%). Note that the fumarate can be obtained by an ordinary method, then making it into an amorphous powder.

Example 75

Synthesis of 4,5-dihydro-3,7-dimethyl-4-(4-(4-(2-pyridyl)piperidin-1-yl)butyl)-1,4-benzoxazepin-5-one 270 mg of the compound of Example 12 was dissolved in 5 ml of acetonitrile, 198 mg (1.2 equivalents) of 4-(2-pyridyl)piperidine chlorate and 0.41 ml (3.5 equivalents) of triethylamine were added, then the resultant mixture was heated and refluxed for 8 hours.

This was then treated and refined in the same way as in Example 31 to obtain the above-referenced compound in an amount of 111 mg (yield of 34%). Note that the fumarate can be obtained by an ordinary method, then making it into an amorphous powder.

Example 76

Synthesis of 4,5-dihydro-3,7-dimethyl-4-(5-(4-(2-pyridyl)piperidin-1-yl)pentyl)-1,4-benzoxazepin-5-one 300 mg of the compound of Example 14 was dissolved in 5 ml of acetonitrile, 210 mg (1.2 equivalents) of 4-(2-pyridyl)piperidine chlorate and 0.43 ml (3.5 equivalents) of triethylamine were added, then the resultant mixture was heated and refluxed for 10 hours.

This was then treated and refined in the same way as in Example 31 to obtain the above-referenced compound in an amount of 170 mg (yield of 46%). Note that the fumarate can be obtained by an ordinary method, then making it into an amorphous powder.

Example 77

Synthesis of 4,5-dihydro-8-methoxy-4-(5-(4-(2-pyridyl)-1,2,5,6-tetrahydropyridin-1-yl)pentyl)-1,4-benzoxazepin-5-one 200 mg of the compound of Example 5 was dissolved in 5 ml of acetonitrile, 113 mg (1.2 equivalents) of 4-(2-pyridyl)-1,2,5,6-tetrahydropyridine and 0.16 ml (2 equivalents) of triethylamine were added, then the resultant mixture was heated and refluxed for 8 hours.

This was then treated and refined in the same way as in Example 31 to obtain the above-referenced compound in an amount of 218 mg (yield of 91%). Note that the fumarate can be obtained by an ordinary method, then making it into an amorphous powder.

Example 78

Synthesis of 4,5-dihydro-8-methoxy-4-(5-(4-(2-pyridyl)piperidin-1-yl)pentyl)-1,4-benzoxazepin-5-one 200 mg of the compound of Example 5 was dissolved in 5 ml of acetonitrile, 140 mg (1.2 equivalents) of 4-(2-pyridyl)-1,2,5,6-tetrahydropyridine chlorate and 0.29 ml (3.5 equivalents) of triethylamine were added, then the resultant mixture was heated and refluxed for 10 hours.

This was then treated and refined in the same way as in Example 31 to obtain the above-referenced compound in an amount of 107 mg (yield of 46%). Note that the fumarate can be obtained by an ordinary method, then making it into an amorphous powder.

Example 79

Synthesis of 4,5-dihydro-8-methoxy-4-(3-(4-(2-pyridyl)piperidin-1-yl)propyl)-1 4-benzoxazepin-5-one 240 mg of the compound of Example 3 was dissolved in 5 ml of DMF, 213 mg (1.2 equivalents) of 4-(2-pyridyl) piperidine chlorate, 269 mg (2 equivalents) of sodium iodide, and 0.44 ml (3.5 equivalents) of triethylamine were added, and the resultant mixture was agitated at 80° C. for 15 hours.

This was then treated and refined in the same way as in Example 31 to obtain the above-referenced compound in an amount of 95 mg (yield of 27%). Note that the fumarate can be obtained by an ordinary method, then making it into an amorphous powder.

Example 80

Synthesis of 3-chloro-4,5-dihydro-4-(4-(4-((4-methyl)pyrimidin-2-yl)-1,2,5,6-tetrahydropyridin-1-yl)butyl)-1,4-benzoxazepin-5-one 200 mg of the compound of Example 16 was dissolved in 5 ml of DMF, 178 mg (1.2 equivalents) of the chlorate of the compound of Example 28, 210 mg (2 equivalents) of sodium iodide, and 0.34 ml (3.5 equivalents) of triethylamine were added, and the resultant mixture was agitated at 90° C. for 20 hours.

This was then treated and refined in the same way as in Example 31 to obtain the above-referenced compound in an amount of 154 mg (yield of 54%). Note that the fumarate can be obtained by an ordinary method, then recrystallizing it with a mixed solvent of methanol and ether.

Example 81

Synthesis of 3-chloro-4,5-dihydro-4-(4-(4-(2-pyridyl)piperidin-1-yl)butyl)-1,4-benzoxazepin-5-one 550 mg of the compound of Example 16 was dissolved in 10 ml of DMF, 210 mg (1.2 equivalents) of 4-(2-pyridyl) piperidine, 390 mg (2 equivalents) of sodium iodide, and 0.36 ml (2 equivalents) of triethylamine were added, and the resultant mixture was agitated at 90° C. for 17 hours.

This was then treated and refined in the same way as in Example 31 to obtain the above-referenced compound in an amount of 450 mg (yield of 85%). Note that the fumarate can be obtained by an ordinary method, then recrystallizing it with acetone.

Example 82

Synthesis of 3-chloro-4,5-dihydro-4-(4-4-(2-pyridyl)-1,2,5,6-tetrahydropyridin-1-yl)butyl)-1,4-benzoxazepin-5-one 487 mg of the compound of Example 16 was dissolved in 10 ml of DMF, 180 mg (1.2 equivalents) of 4-(2-pyridyl)-1,2,5,6-tetrahydropyridine, 336 mg (2 equivalents) of sodium iodide, and 0.31 ml (2 equivalents) of triethylamine were added, and the resultant mixture was agitated at 90° C. for 20 hours.

This was then treated and refined in the same way as in Example 31 to obtain the above-referenced compound in an amount of 290 mg (yield of 63%). Note that the chlorate can be obtained by making the chlorate by an ordinary method, then recrystallizing it with a mixed solvent of methanol and acetone.

Example 83

Synthesis of 3-chloro-4,5-dihydro-4-(4-(3-(2-pyridyl)-1,2,5,6-tetraydropyridin-1-yl)butyl)-1,4-benzoxazepin-5-one 102 mg of the compound of Example 16 was dissolved in 2 ml of DMF, 52 mg (0.9 equivalents) of 3-(2-pyridyl)-1,2,5,6-tetrahydropyridine, 107 mg (2 equivalents) of sodium iodide, and 66 mg (2 equivalents) of triethylamine were added, and the resultant mixture was agitated at 90° C. for 20 hours.

This was then treated and refined in the same way as in Example 31 to obtain the above-referenced compound in an amount of 65 mg (yield of 49%). Note that the fumarate can be obtained by an ordinary method, then making it into an amorphous powder.

Example 84

Synthesis of 4,5-dihydro-3-methyl-4-(4-(4-(2-pyridyl)-1,2,5,6-tetrahydropyridin-1-yl)butyl)-1,4-benzoxazepin-5-one 230 mg of the compound of Example 8 was dissolved in 8 ml of dioxene, 100 mg (1.2 equivalents) of 4-(2-pyridyl)-1,2,5,6-tetrahydropyridine and 0.13 ml (1.5 equivalents) of triethylamine were added, and the resultant mixture was agitated at 80° C. for 10 hours.

This was then treated and refined in the same way as in Example 31 to obtain the above-referenced compound in an amount of 210 mg (yield of 88%). Note that the fumarate can be obtained by an ordinary method, then recrystallizing it with a mixed solvent of acetone and ether.

Example 85

Synthesis of 4,5-dihydro-3-ethyl-4-(4-(4-(2-pyridyl)-1,2,5,6-tetrahydropyridin-1-yl)butyl)-1,4-benzoxazepin-5-one 150 mg of the compound of Example 10 was dissolved in 2 ml of DMF, 129 mg (1.5 equivalents) of 4-(2-pyridyl)-1,2,5,6-tetrahydropyridine, 161 mg (2 equivalents) of sodium iodide, and 108 mg (2 equivalents) of triethylamine were added, and the resultant mixture was agitated at 90° C. for 20 hours.

This was then treated and refined in the same way as in Example 31 to obtain the above-referenced compound in an amount of 105 mg (yield of 49%). Note that the fumarate can be obtained by an ordinary method, then making it into an amorphous powder.

Example 86

Synthesis of 3-chloro-4,5-dihydro-4-(4-(4-(2-pyridyl)-1,2,5,6-tetrahydropyridin-1-yl)butyl)-1,4-benzoxazepin-5-one (synthesis of identical substance as Example 82 by different method)

800 mg of the compound of Example 23 was dissolved in 20 ml of ethanol, 140 mg (2 equivalents) of sodium borohydride was added under ice cooling, then the result was agitated at room temperature for 10 minutes. Water was added and extraction was performed with ethyl acetate. The organic layer was washed with water and saturated saline, then was dried with anhydrous magnesium sulfate. The solvent was distilled off and the resultant crude product was refined with silica gel column chromatography (methylene chloride:methanol=30:1), to obtain the above-referenced compound in an amount of 600 mg (yield of 81%).

Example 87

Synthesis of 3-chloro-4,5-dihydro-4-(4-(4-(2-pyrimidinyl)-1,2,5,6-tetrahydropyridin-1-yl)butyl)-1,4-benzoxazepin-5-one (synthesis of identical substance as Example 56 by different method)

560 mg of the compound of Example 24 was dissolved in 15 ml of ethanol, 98 mg (2 equivalents) of sodium borohydride was added under ice cooling, then the resultant mixture was agitated at room temperature for 10 minutes.

This was then treated and refined in the same way as in Example 80 to obtain the above-referenced compound in an amount of 462 mg (yield of 89%).

Evaluation Example 1
Evaluation of Affinity with Serotonin Receptor

The affinity of the compounds of the general formulas (I), (II), and (III) with a serotonin receptor was evaluated in accordance with the method of S. T. Peuroutka et al. (J. Neurochem., vol. 47, pp. 529–540, 1986). That is, the hippocampuses extracted from male Wistar rats were homogenized while adding 50 mM tris-phosphate buffer (pH 7.7). The homogenate was centrifuged at 37° C. and 40000×g for 10 minutes. The same buffer was added to the obtained precipitate, then this was homogenized again and was similarly centrifuged to obtain the precipitate. This homogenization-centrifugation operation was repeated two times to obtain a final precipitate to which was then added 10 uM of N-methyl-N-2-propynylbenzylamine (Pargyline), 4 mM of calcium chloride, and 0.1% ascorbic acid contained in a 50 mM tris-phosphate buffer (ph 7.7). This was then homogenized to prepare the serotonin receptor.

For the binding experiment, 0.4 nM of [3H]2-di-n-propylamino-8-hydroxy-1,2,3,4-tetrahydronapthalene (8-DPAT; 8-hydroxy-N,N-dipropyl-2-aminotetetrilin) was used, various concentrations of test samples were added to a system of 0.25 mg/ml of protein or a total of 0.25 ml, and these were incubated at 25° C. for 30 minutes. A Whatman GF/C filter was used to filter each of the reaction solutions, then the filter was washed by 20 mM tris-phosphate buffer (pH 7.7). The serotonin receptor was trapped by the filter and the radio activity of the 8-OH-DAPT bonded to it was measured to find the degree of binding. The 50% inhibiting concentration of binding affinity ($IC_{50}$) was calculated from the degrees of binding in the various sample concentrations. The compounds of the general formulae (I), (II), and (III) exhibited a strong affinity with the serotonin 5-$HT_{1A}$ receptor of an nM order of the $IC_{50}$. The $IC_{50}$ values of typical compounds are shown together with the $IC_{50}$ values with respect to the dopamine $D_2$ receptor.

Evaluation Example 2
Evaluation of Affinity with Dopamine $D_2$ Receptor

The affinity of the compounds of the general formulas (I), (II), and (III) with a dopamine $D_2$ receptor was evaluated in accordance with the method of Kakohler et al. (Biochem. Pharmacol., vol. 34, pp. 2251–2259, 1985). That is, the corpus striatums excised from male Wistar rats were homogenized with the addition of 120 mM sodium chloride, 5 mM potassium chloride, 2 mM calcium chloride, 1 mM magnesium chloride, and 0.01% ascorbic acid contained in 50 mM tris-phosphate buffer (pH 7.7). The homogenate was centrifuged at 37° C. and 35000×g for 10 minutes. The same buffer was added to the resultant precipitate, then this was homogenized again and was similarly centrifuged to obtain the precipitate. The same buffer was added to this precipitate which was then again homogenized to prepare the dopamine $D_2$ receptor.

For the binding experiment, use was made of 1.0 nM of [3H]3,5-dichloro-N-[(1-ethyl-2-pyrrolidinyl)methyl]-6-hydroxy-o-anisamide (Raclopride), various concentrations of test samples were added to a system of 0.34 mg/ml of protein or a total of 0.25 ml, incubation was performed at 25° C. for 60 minutes, then the radioactivity was measured in the same way as in the Evaluation Example 1 to find the degree of binding.

The 50% inhibiting concentration of binding affinity ($IC_{50}$) was calculated from the degrees of binding at various concentrations of the added samples. It is clear that the compounds of the general formulae (I), (II), and (III) exhibit a weak affinity to a dopamine $D_2$ receptor of an $IC_{50}$ of more than about 0.1 $\mu$M. The $IC_{50}$ values of typical compounds are shown together with the $IC_{50}$ values for the serotonin receptor. From these results, it is clear that the compounds of the general formulae (I), (II), and (III) exhibit an affinity to the serotonin receptor 5-$HT_{1A}$ of approximately 100 to 1000 times that to the dopamine $D_2$ receptor.

| Example | $IC_{50}$ (5-$HT_{1A}$) (nM) | $IC_{50}$ ($D_2$) (nM) | $D_2$/5-$HT_{1A}$ |
| --- | --- | --- | --- |
| 35 | 1.5 | 294 | 196 |
| 41 | 1.7 | 266 | 156 |
| 46 | 0.77 | 51 | 67 |
| 47 | 3.8 | 1390 | 366 |
| 48 | 1.2 | 233 | 194 |
| 49 | 0.88 | 405 | 460 |
| 53 | 11.0 | 979 | 89 |
| 55 | 13.0 | 1251 | 96 |
| 56 | 1.38 | 494 | 358 |
| 57 | 5.81 | 1800 | 310 |
| 59 | 0.65 | 341 | 525 |
| 60 | 1.11 | 1280 | 1153 |
| 61 | 0.68 | 256 | 376 |
| 66 | 0.58 | 128 | 221 |

-continued

| Example | IC$_{50}$ (5-HT$_{1A}$) (nM) | IC$_{50}$ (D$_2$) (nM) | D$_2$/5-HT$_{1A}$ |
|---|---|---|---|
| 67 | 0.44 | 359 | 816 |
| 74 | 4.41 | 338 | 77 |
| 82 | 0.47 | 128 | 84 |

Evaluation Example 3
Evaluation of Anticonflict Action

The anticonflict action of the compounds of the general formulae (I), (II), and (III) was evaluated in accordance with the NaCl-Lick conflict method of Tanga et al. (Pharmacol., Biochem., Behav., vol. 32, pp. 773–776, 1989). That is, six-week old male Wistar rats in groups of six to 10 were deprived of water for 48 hours and placed in an experimental apparatus placed in a soundproof box (apparatus made of acrylic resin, 20×20×30 cm, provided with a drinking outlet having a diameter of 1 cm at height of 8 cm from the floor, designed to be able to measure the number of drops per unit hour by a drinkometer), and the anticonflict action of the medicament was evaluated using as an indicator the number of drops (number of licks) in 5 minutes from the start of drinking of 2% saline. The tested medicament was orally administered in an amount of 0.2 ml/100 g body weight 1 hour before the start of the test. The compounds of the present invention exhibited a significant anticonflict action. The minimum effective amounts of typical compounds are shown in the Table.

| Compound no. | Minimum effective dosage (mg/kg, p.o.) |
|---|---|
| 32 | 30 |
| 33 | 10 |
| 34 | 30 |
| 36 | 30 |
| 41 | 10 |
| 46 | 10 |
| 48 | 30 |
| 54 | 10 |
| 82 | 30 |

Evaluation Example 4
Evaluation of Efficacy On Experimental Ischemic Brain Tissue Damage The evaluation of the efficacy on ischemic brain damage of the compounds of the general formulae (I), (II), and (III) was performed using the transient right middle cerebral artery occlusion (MCAO) model of Koizumi et al. (Jap. J. Stroke, vol. 8, pp. 1 to 8, 1986). That is, 10 to 11 week old Wistar male rats were used and the right middle cerebral artery was temporarily obstructed for 60 minutes. 10 days after the restart of the blood flow, the brains were excised and the degree of brain tissue damage of the cerebral cortex and corpus striatum of the obstructed side were evaluated by the damage marker of the number of benzodiazepine bindings. The tested drugs were dissolved in physiological saline and administered subcutaneously at the backs of the rats immediately after the right middle cerebral artery occlusion. As a control, physiological saline of 2 mg/kg body weight was similarly administered.

The compounds of the present invention significantly suppressed the brain tissue damage seen in the control group. The minimum effective amounts of typical compounds are shown in the Table.

| Compound no. | Minimum effective dosage (mg/kg, s.c.) |
|---|---|
| 46 | 0.3 |
| 48 | 1.0 |
| 56 | 1.0 |
| 59 | 1.0 |
| 60 | 1.0 |
| 61 | 1.0 |
| 82 | 0.3 |
| 84 | 0.3 |

Manufacturing Example 1
Manufacture of Capsule

Five parts (parts by weight) of the compound of Example 82, 243 parts of potato starch (parts by weight), 2 parts of magnesium stearate (parts by weight) were mixed well by a blender, then 250 mg portions were filled in No. 1 hard gelatin capsules to prepare the capsule agents. Each No. 1 capsule contained 5 mg of the hydrochloride of the compound of Example 82.

Manufacturing Example 2
Manufacture of Rectal Suppository

Witepsol H-15 was warmed to melt. Into this was homogeneously mixed the fumarate of the compound of Example 59 to give a concentration of 2.5 mg/ml, Next, this was poured in 2 ml amounts into a rectal suppository mold to prepare the rectal suppositories. Each suppository contained 5 mg of the fumarate of the compound of Example 59.

Manufacturing Example 3
Manufacture of Injection

The hydrochloride of the compound of Example 56 was dissolved in physiological saline to give a concentration of 5 mg/ml. This was sterily filtered by a filter of a size of 0.22 $\mu$m and sterily filled in 1 ml amounts in ampules to prepare injections. Each ampule contained 5 mg of the hydrochloride of the compound of Example 56.

| Ex. | Chemical structure | m.p. (Recrystallization solvent) | IR (cm$^{-1}$) | NMR (δ ppm) | MS/Element analysis |
|---|---|---|---|---|---|
| 1 | 7-Chloro-N-(2-chloroethyl) benzoxazepinone |  | 1632 1492 1434 1348 1108 (CHCl$_3$) | 7.84 (1H, d, J = 2 Hz), 7.37–7.39 (1H, m), 6.93 (1H, d, J = 8 Hz), 6.31 (1H, d, J = 4 Hz), 5.71 (1H, d, J = 4 Hz), 3.93 (2H, t, J = 6 Hz), 3.79 (2H, t, J = 6 Hz) (CDCl$_3$) |  |
| 2 | N-(4-bromobutyl) benzoxazepinone |  | 2938 1311 1682 1051 1654 748 1643 1610 1455 1412 (CHCl$_3$) | 7.87 (1H, d, J = 8 Hz), 7.42 (1H, t, J = 8 Hz), 7.19 (1H, t, J = 8 Hz), 6.97 (1H, d, J = 8 Hz), 6.37 (1H, d, J = 7 Hz), 5.57 (1H, d, J = 7 Hz), 3.69 (2H, t, J = 7 Hz), 3.47 (2H, t, J = 7 Hz), 1.78–2.02 (4H, m) (CDCl$_3$) |  |
| 3 | 7-Methoxy-N-(3-chloropropyl) benzoxazepinone |  | 2962 1684 1638 1609 1570 1500 1445 1404 1171 (NaCl) | 7.81 (1H, d, J = 9 Hz), 6.71 (1H, dd, J = 2 Hz, 9 Hz), 6.47 (1H, d, J = 2 Hz), 6.28 (1H, d, J = 4 Hz), 5.60 (1H, d, J = 4 Hz), 3.82 (3H, s), 3.77 (2H, t, J = 7 Hz), 3.64 (2H, t, J = 6 Hz), 2.14–2.20 (2H, m) (CDCl$_3$) |  |
| 4 | 7-Methoxy-N-(4-bromobutyl) benzoxazepinone |  | 2973 1632 1606 1456 1397 (CHCl$_3$) | 7.82 (1H, d, J = 9 Hz), 6.72 (1H, dd, J = 3 Hz, 9 Hz), 6.47 (1H, d, J = 3 Hz), 6.31 (1H, d, J = 4 Hz), 5.54 (1H, d, J = 4 Hz), 3.82 (3H, s), 3.67 (2H, t, J = 7 Hz), 3.47 (2H, t, J = 7 Hz), 1.77–2.01 (4H, m) (CDCl$_3$) |  |
| 5 | 7-Methoxy-N-(5-bromopentyl) benzoxazepinone |  | 2938 1682 1646 1611 1570 1500 1444 1405 1258 (NaCl) | 7.82 (1H, d, J = 9 Hz), 6.71 (1H, dd, J = 2 Hz, 9 Hz), 6.46 (1H, d, J = 2 Hz), 6.29 (1H, d, J = 4 Hz), 5.53 (1H, d, J = 4 Hz), 3.82 (3H, s), 3.62 (2H, t, J = 7 Hz), 3.42 (2H, t, J = 7 Hz), 1.92 (2H, q, J = 7 Hz), 1.70 (2H, q, J = 7 Hz), 1.50–1.55 (2H, m) (CDCl$_3$) |  |

| Ex. | Chemical structure | m.p. (Recrystallization solvent) | IR (cm⁻¹) | NMR (δ ppm) | MS/Element analysis |
|---|---|---|---|---|---|
| 6 | 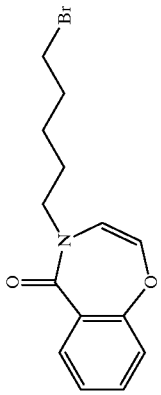 | | 2938 1680 1640 1604 1574 1481 1456 1412 1245 (NaCl) | 7.87 (1H, dd, J = 2 Hz, 8 Hz), 6.38–7.43 (1H, m), 7.17 (1H, t, J = 8 Hz), 6.98 (1H, t, J = 8 Hz), 6.35 (1H, d, J = 5 Hz), 5.55 (1H, d, J = 5 Hz), 3.65 (2H, t, J = 7 Hz), 3.42 (2H, t, J = 7 Hz), 1.93 (2H, q, J = 7 Hz), 1.72 (2H, q, J = 7 Hz), 1.52–1.57 (2H, m) (CDCl₃) | |
| 7 | 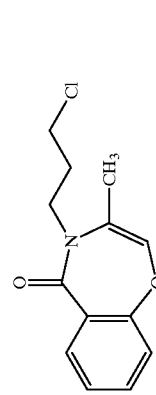 | | 2961 1682 1630 1603 1575 1479 1458 1350 1292 (NaCl) | 7.83 (1H, dd, J = 2 Hz, 8 Hz), 7.38–7.42 (1H, m), 7.18 (1H, t, J = 8 Hz), 6.97 (1H, d, J = 8 Hz), 6.37 (1H, s), 3.93 (2H, t, J = 7 Hz), 3.65 (2H, t, J = 6 Hz), 2.15 (2H, q, J = 7 Hz), 1.85 (3H, s) (CDCl₃) | |
| 8 | 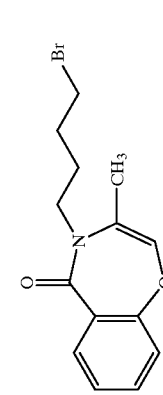 | | 2958 1682 1640 1574 1479 1206 998 (NaCl) | 7.82–7.84 (1H, m), 7.38–7.42 (1H, m), 7.17–7.21 (1H, m), 6.98 (1H, d, J = 8 Hz), 6.38 (1H, s), 3.84 (2H, t, J = 7 Hz), 3.47 (2H, t, J = 7 Hz), 1.93–2.00 (2H, m), 1.82 (3H, s), 1.77–1.82 (2H, m) (CDCl₃) | |
| 9 | 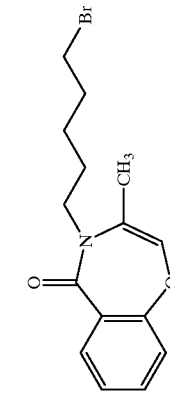 | | 2937 2860 1736 1676 1638 1603 1577 1456 1290 (NaCl) | 7.83 (1H, dd, J = 2 Hz, 8 Hz), 7.37–7.41 (1H, m), 7.18 (1H, t, J = 8 Hz), 6.96 (1H, d, J = 8 Hz), 6.37 (1H, s), 3.80 (2H, t, J = 7 Hz), 3.41 (2H, t, J = 7 Hz), 1.92 (2H, q, J = 7 Hz), 1.80 (3H, s), 1.67 (2H, q, J = 7 Hz), 1.55–1.62 (2H, m) (CDCl₃) | |
| 10 | 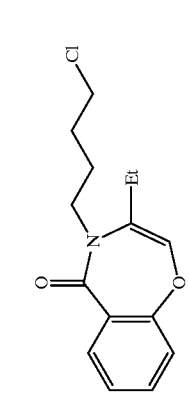 | | 1632 1605 1456 1397 (CHCl₃) | 7.84 (1H, dd, J = 2 Hz, 8 Hz), 7.39 (1H, t, d, J = 8 Hz, 2 Hz), 7.19 (1H, t, d, J = 8 Hz, 2 Hz), 6.98 (1H, d, d, J = 8 Hz, 2 Hz), 6.46 (1H, s), 3.83 (2H, t, J = 6 Hz), 3.59 (2H, t, J = 6 Hz), 2.18 (2H, q, J = 7 Hz), 1.7–1.91 (4H, m), 0.96 (3H, t, J = 7 Hz) (CDCl₃) | |

-continued

| Ex. | Chemical structure | m.p. (Recrystallization solvent) | IR (cm⁻¹) | NMR (δ ppm) | MS/Element analysis |
|---|---|---|---|---|---|
| 11 | (structure: benzoxazepine with Me on ring, N-(CH₂)₄-Br, Me on 3-position) | | 1630 1492 1345 1108 (CHCl₃) | 7.72 (1H, d, J = 8 Hz), 7.00 (1H, dd, J = 1 Hz, 8 Hz), 6.79 (1H, s), 6.36 (1H, d, J = 1 Hz), 3.83 (2H, t, J = 7 Hz), 3.47 (2H, t, J = 6 Hz), 2.35 (3H, s), 1.91–2.01 (2H, m), 1.80 (3H, d, J = 1 Hz), 1.73–1.84 (2H, m) (CDCl₃) | |
| 12 | (structure: benzoxazepine with Me, N-(CH₂)₄-Br, Me) | | 1636 1492 1423 (CHCl₃) | 7.62 (1H, d, J = 2 Hz), 7.18 (1H, d, d, J = 8 Hz, 2 Hz), 6.86 (1H, d, J = 8 Hz), 6.37 (1H, s), 3.83 (2H, t, J = 7 Hz), 3.59 (2H, t, J = 6 Hz), 2.33 (6H, s), 1.78–1.92 (4H, m) (CDCl₃) | |
| 13 | (structure: benzoxazepine with F, N-(CH₂)₄-Br, Me) | | 1636 1590 1487 1434 1344 1273 888 (CHCl₃) | 7.50 (1H, dd, J = 3 Hz, 9 Hz), 7.08 (1H, m), 6.94 (1H, dd, J = 5 Hz, 9 Hz), 6.38 (1H, s), 3.83 (2H, t, J = 7 Hz), 3.46 (2H, t, J = 6 Hz), 1.92–1.99 (2H, m), 1.82 (3H, s), 1.78–1.83 (2H, m) (CDCl₃) | |
| 14 | (structure: benzoxazepine with Me, N-(CH₂)₅-Br, Me) | | 2942 1631 1492 1422 1286 (CHCl₃) | 7.62 (1H, s), 7.18 (1H, d, J = 8 Hz), 6.86 (1H, d, J = 8 Hz), 6.36 (1H, s), 3.79 (2H, t, J = 7 Hz), 3.41 (2H, t, J = 6 Hz), 2.33 (3H, s), 1.79 (3H, s), 1.52–1.71 (6H, m) (CDCl₃) | |
| 15 | (structure: benzoxazepine with N-(CH₂)₃-Cl, Cl on 3-position) | | 1654 1604 1574 1458 1201 1036 981 (NaCl) | 7.87–7.90 (1H, m), 7.44–7.48 (1H, m), 7.23–7.27 (1H, m), 7.02–7.04 (1H, m), 6.72 (1H, s), 4.05 (2H, t, J = 7 Hz), 3.64 (2H, t, J = 7 Hz), 2.21 (2H, m) (CDCl₃) | |

-continued

| Ex. | Chemical structure | m.p. (Recrystallization solvent) | IR (cm$^{-1}$) | NMR (δ ppm) | MS/Element analysis |
|---|---|---|---|---|---|
| 16 | 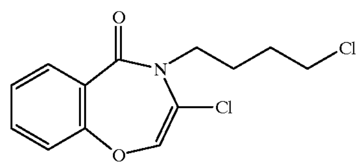 | | 2956 1704 1644 1605 1574 1538 1479 1236 (NaCl) | 7.86–7.89 (1H, m), 7.43–7.47 (1H, m), 7.22–7.26 (1H, m), 7.02 (1H, d, J = 8 Hz), 6.73 (1H, s), 3.94 (2H, t, J = 6 Hz), 3.57–3.60 (2H, m), 1.86–1.89 (4H, m) (CDCl$_3$) | |
| 17 | 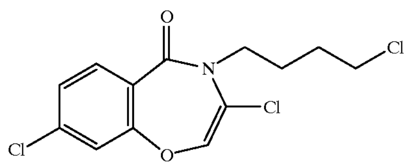 | | 1649 1609 1499 1449 1274 (CHCl$_3$) | 7.82 (1H, d, J = 8 Hz), 7.23 (1H, d, d, J = 8 Hz, 2 Hz), 7.06 (1H, d, J = 2 Hz), 6.71 (1H, s), 3.89–3.96 (2H, m), 3.55–3.61 (2H, m), 1.82–1.99 (4H, m) (CDCl$_3$) | |
| 18 | 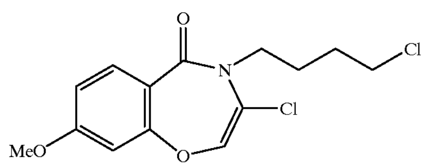 | | 2941 1644 1609 1499 1479 1225 (CHCl$_3$) | 7.82 (1H, d, J = 9 Hz), 6.77 (1H, d, J = 2 Hz, 9 Hz), 6.69 (1H, s), 6.52 (1H, d, J = 2 Hz), 3.90–3.93 (2H, m), 3.83 (3H, s), 3.56–3.59 (2H, m), 1.81–1.85 (4H, m) (CDCl$_3$) | |
| 19 | 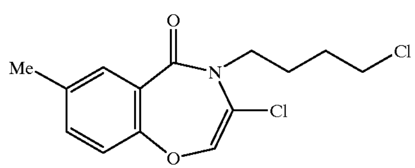 | | 1646 1610 1499 1274 1235 (CHCl$_3$) | 7.66 (1H, d, J = 2 Hz), 7.24 (1H, dd, J = 8 Hz, 2 Hz), 6.90 (1H, d, J = 8 Hz), 6.71 (1H, s), 3.91–3.94 (2H, m), 3.56–3.60 (2H, m), 2.35 (3H, s), 1.84–1.89 (4H, m) (CDCl$_3$) | |
| 20 | 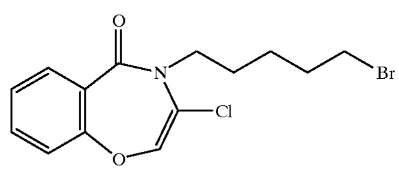 | | 2939 1658 1604 1478 1453 1376 1328 1245 1200 (NaCl) | 7.87 (1H, dd, J = 2 Hz, 8 Hz), 7.42–7.47 (1H, m), 7.21–7.26 (1H, m), 7.03 (1H, d, J = 8 Hz), 6.72 (1H, s), 3.90 (2H, t, J = 7 Hz), 3.41 (2H, t, J = 7 Hz), 1.92 (2H, q, J = 7 Hz), 1.74 (2H, q, J = 7 Hz), 1.54–1.58 (2H, m) (CDCl$_3$) | |

-continued

| Ex. | Chemical structure | m.p. (Recrystallization solvent) | IR (cm$^{-1}$) | NMR (δ ppm) | MS/Element analysis |
|---|---|---|---|---|---|
| 21 | MeO-substituted benzoxazepinone with N-(4-bromobutyl) and 2-CH$_2$Cl | | 2360 1644 1491 1464 1429 1220 (CHCl$_3$) | 7.22 (1H, d, J = 3 Hz), 6.96–7.03 (2H, m), 6.69 (1H, s), 5.75 (1H, s), 5.43 (1H, s), 4.21–4.28 (1H, m), 3.81 (3H, s), 3.45–3.51 (3H, m), 1.95–2.00 (2H, m), 1.84–1.91 (2H, m) (CDCl$_3$) | |
| 22 | Benzoxazepinone with N-(4-bromobutyl) and 2-CH$_2$OCH$_3$ | | 1735 1644 1605 1574 1479 1385 1241 (NaCl) | 7.73–7.75 (1H, m), 7.37–7.41 (1H, m), 7.17 (1H, t, J = 8 Hz), 6.99 (1H, d, J = 8 Hz), 5.53 (1H, s), 5.49 (1H, s), 5.26 (1H, s), 4.17–4.24 (1H, m), 3.68 (3H, s), 3.47–3.54 (3H, m), 1.95–2.02 (2H, m), 1.82–1.89 (2H, m) (CDCl$_3$) | |
| 23 | Benzoxazepinone with 2-Cl and N-(4-(4-(pyridin-2-yl)pyridinium)butyl) Cl$^-$ | | 3445 3008 1642 1603 1561 1475 1456 1342 1177 (KBr) | 9.21 (2H, d, J = 7 Hz), 8.87 (1H, d, J = 4 Hz), 8.81 (2H, d, J = 7 Hz), 8.44 (1H, d, J = 8 Hz), 8.11 (1H, d, t, J = 2 Hz, 8 Hz), 7.77 (1H, dd, J = 2 Hz, 8 Hz), 7.66 (1H, dd, J = 2 Hz, 4 Hz), 7.58 (1H, d, J = 2 Hz, 8 Hz), 7.33 (1H, t, J = 8 Hz), 7.14 (2H, t, J = 8 Hz), 7.10 (1H, s), 4.71 (2H, t, J = 7 Hz), 3.87 (2H, t, J = 7 Hz), 2.01–2.12 (2H, m), 1.65–1.71 (2H, m) (DMSO-d$_6$) | |
| 24 | Benzoxazepinone with 2-Cl and N-(4-(4-(pyridin-2-yl)pyridinium)butyl) Cl$^-$ | | 3450 2365 1652 1553 1454 1414 1338 1201 1105 (KBr) | 9.49 (2H, d, J = 7 Hz), 8.96–8.98 (4H, m), 7.82–7.84 (1H, m), 7.45–7.47 (2H, m), 7.23–7.28 (1H, m), 7.02 (1H, d, J = 7 Hz), 6.74 (1H, s), 5.19 (2H, t, J = 8 Hz), 4.03 (2H, t, J = 7 Hz), 2.20–2.25 (2H, m), 1.93–1.98 (2H, m) (CDCl$_3$) | |
| 25 Step 1 | Boc-piperidine with 4-OH and 4-(pyridin-2-yl) | | 3022 1681 1561 1424 1368 1244 (CHCl$_3$) | 8.74 (1H, d, J = 5 Hz), 7.22 (1H, t, J = 5 Hz), 4.02–4.15 (2H, m), 3.11–3.32 (4H, m), 2.16–2.25 (2H, m), 1.49 (9H, s) (CDCl$_3$) | FAB-Mass 280 (M + H)$^+$ |

-continued

| Ex. | Chemical structure | m.p. (Recrystallization solvent) | IR (cm⁻¹) | NMR (δ ppm) | MS/Element analysis |
|---|---|---|---|---|---|
| 25 Step 2 | Boc-N-[piperidine]-[pyridine] | | 3018 1682 1556 1421 1368 1241 1168 (CHCl₃) | 8.69 (2H, d, J = 5 Hz), 7.15–7.21 (1H, m), 7.10 (1H, t, J = 5 Hz), 4.17–4.22 (2H, m), 3.64 (2H, t, J = 6 Hz), 2.70–2.78 (2H, m), 1.49 (9H, s) (CDCl₃) | FAB-Mass 262 (M + H)⁺ |
| 25 Step 3 | HN-[piperidine]-[pyridine] | | 3021 2984 1571 1557 1423 1210 1206 (CHCl₃) | 8.68 (2H, d, J = 5 Hz), 7.27–7.29 (2H, m), 7.09 (1H, t, J = 5 Hz), 3.62–3.64 (2H, m), 3.12 (2H, t, J = 6 Hz), 2.62–2.66 (2H, m) (CDCl₃) | FAB-Mass 162 (M + H)⁺ |
| 26 Step 1 | Boc-N-[piperidine]-[pyridine] | | 3024 1682 1563 1506 1426 1367 1248 (CHCl₃) | 8.68 (2H, d, J = 5 Hz), 7.13 (1H, t, J = 5 Hz), 4.15–4.28 (2H, m), 3.00–3.06 (1H, m), 2.85–2.91 (2H, m), 1.98–2.02 (2H, m), 1.75–1.87 (2H, m), 1.47 (9H, s) (CDCl₃) | FAB-Mass 264 (M + H)⁺ |
| 26 Step 2 | HN-[piperidine]-[pyridine] | | 3023 3017 1574 1563 1427 1228 1206 (CHCl₃) | 8.68 (2H, d, J = 5 Hz), 7.12 (1H, t, J = 5 Hz), 3.20–3.24 (2H, m), 2.99–3.06 (1H, m), 2.75–2.82 (2H, m), 2.00–2.04 (2H, m), 1.76–1.86 (2H, m) (CDCl₃) | FAB-Mass 164 (M + H)⁺ |
| 27 Step 1 | [pyridine]-[pyridine] | | 3027 1734 1668 1596 1547 1385 1218 (KBr) | 8.87 (2H, d, J = 5 Hz), 8.78 (2H, d, J = 5 Hz), 8.29 (2H, d, J = 5 Hz), 7.30 (1H, t, J = 5 Hz) (CDCl₃) | |
| 27 Step 2 | Bn-N-[piperidine]-[pyridine] | | 2910 2809 1654 1568 1533 1494 1424 1374 (KBr) | 8.67 (2H, d, J = 5 Hz), 7.38–7.39 (2H, m), 7.33 (2H, t, J = 7 Hz), 7.26–7.27 (1H, m), 7.20–7.22 (1H, m), 7.07 (1H, t, J = 5 Hz), 3.67 (2H, s), 3.23–3.27 (2H, m), 2.82–2.88 (4H, m) (CDCl₃) | |
| 27 Step 3 | HN-[piperidine]-[pyridine] · HCl | | 3374 2956 2793 2612 1659 1608 1568 1556 1426 1390 (KBr) | 9.27 (2H, brs), 8.81 (2H, d, J = 5 Hz), 7.39 (1H, t, J = 5 Hz), 7.15–7.18 (2H, m), 3.81–3.87 (2H, m), 3.30–3.36 (2H, m), 2.81–2.85 (2H, m) (DMSO-d₆) | |

| Ex. | Chemical structure | m.p. (Recrystallization solvent) | IR (cm⁻¹) | NMR (δ ppm) | MS/Element analysis |
|---|---|---|---|---|---|
| 28 Step 1 | (1-benzyl-4-methylpyrimidin-2-yl-tetrahydropyridine) | | 3019 2400 1652 1520 1418 1213 1046 (CHCl$_3$) | 8.50 (1H, d, J = 5 Hz), 7.33–7.38 (2H, m), 7.30–7.32 (2H, m), 7.23–7.27 (1H, m), 7.17 (1H, t, J = 3 Hz), 6.92 (1H, d, J = 5 Hz), 3.66 (2H, s), 3.25 (2H, d, J = 3 Hz), 2.74 (4H, s), 2.48 (3H, s) (CDCl$_3$) | |
| 28 Step 2 | (4-methylpyrimidin-2-yl-tetrahydropyridine HCl) | | 2956 2841 1657 1578 1554 1441 1393 1367 1251 (KBr) | 9.08–9.35 (2H, brs), 8.65 (1H, d, J = 5 Hz), 7.28 (1H, t, J = 5 Hz), 7.13 (1H, s), 3.83 (2H, brs), 3.30–3.31 (2H, m), 2.79–2.80 (2H, m), 2.47 (3H, s) (DMSO-d$_6$) | |
| 29 Step 1 | (Boc-piperidine OH-pyridine) | | 3022 1683 1574 1420 1394 1367 1276 (CHCl$_3$) | 8.74 (2H, d, J = 5 Hz), 7.23 (1H, t, J = 5 Hz), 4.07–4.10 (1H, m), 3.81–3.92 (1H, m), 3.35–3.45 (1H, m), 2.94–3.00 (1H, m), 2.18–2.22 (1H, m), 2.00–2.05 (1H, m), 1.81–1.84 (1H, m), 1.70–1.73 (1H, m), 1.45 (9H, s) (CDCl$_3$) | FAB-Mass 280 (M + H)⁺ |
| 29 Step 2 | (Boc-tetrahydropyridine-pyrimidine) | | 1684 1570 1556 1421 1367 1280 (CHCl$_3$) | 8.67 (2H, d, J = 5 Hz), 7.37–7.39 (1H, m), 7.10 (1H, t, J = 5 Hz), 4.44–4.48 (2H, m), 3.58 (2H, t, J = 6 Hz), 2.39–2.43 (2H, m), 1.50 (9H, s) (CDCl$_3$) | FAB-Mass 262 (M + H)⁺ |
| 29 Step 3 | (tetrahydropyridine-pyrimidine) | | 3036 2952 1653 1627 1569 1558 1424 1229 (CHCl$_3$) | 8.66 (2H, d, J = 5 Hz), 7.36–7.38 (1H, m), 7.09 (1H, t, J = 5 Hz), 3.95 (2H, s), 3.08 (2H, t, J = 6 Hz), 2.41–2.44 (2H, m) (CDCl$_3$) | FAB-Mass 162 (M + H)⁺ |

| Ex. | Chemical structure | m.p. (Recrystallization solvent) | IR (cm$^{-1}$) | NMR (δ ppm) | MS/Element analysis |
|---|---|---|---|---|---|
| 30 Step 1 | 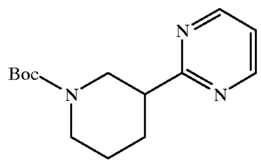 | | 2848 1734 1681 1573 1422 1368 1269 (CHCl$_3$) | 8.67 (2H, d, J = 5 Hz), 7.14 (1H, t, J = 5 Hz), 4.28–4.35 (1H, m), 4.10–4.18 (1H, m), 2.98–3.16 (2H, m), 2.75–2.85 (1H, m), 2.14–2.20 (1H, m), 1.75–1.84 (2H, m), 1.55–1.60 (1H, m), 1.46 (9H, s) (CDCl$_3$) | FAB-Mass 264 (M + H)$^+$ |
| 30 Step 2 | 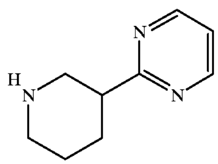 | | 2929 2253 1466 1148 (CHCl$_3$) | 8.68 (2H, d, J = 5 Hz), 7.14 (1H, t, J = 5 Hz), 3.00–3.14 (2H, m), 2.74–2.81 (1H, m), 2.33–2.35 (2H, m), 2.16–2.21 (1H, m), 2.05–2.09 (1H, m), 1.54–1.59 (2H, m) (CDCl$_3$) | FAB-Mass 164 (M + H)$^+$ |
| 31 | 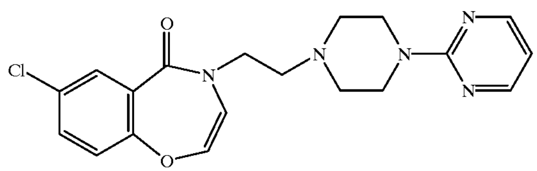 | amorphous (1) | 3418 2945 2474 1726 1635 1590 1462 1208 986 (1) (KBr) | 8.30 (2H, d, J = 5 Hz), 7.84 (1H, d, J = 3 Hz), 7.35 (1H, dd, J = 9 Hz, 3 Hz), 6.92 (1H, d, J = 9 Hz), 6.47 (1H, t, J = 5 Hz), 6.32 (1H, d, J = 4 Hz), 5.72 (1H, d, J = 4 Hz), 3.75–3.84 (6H, m), 2.69 (2H, t, J = 7 Hz), 2.59 (4H, t, J = 5 Hz) (CDCl$_3$) | FAB-Mass 386 (M + H)$^+$ |
| 32 | 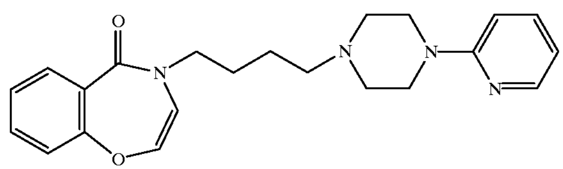 | 150–151° C. (1) (CH$_2$Cl$_2$—Et$_2$O-hexane) | 2941 1682 1651 1638 1593 1485 1434 1415 1311 1245 (neat) | 8.18 (1H, d, J = 5 Hz), 7.87 (1H, d, J = 6 Hz), 7.39–7.54 (2H, m), 7.17 (1H, t, J = 6 Hz), 6.96 (1H, d, J = 8 Hz), 6.59–6.68 (2H, m), 6.35 (1H, d, J = 5 Hz), 5.57 (1H, d, J = 5 Hz), 3.67 (2H, t, J = 7 Hz), 3.54 (4H, t, J = 5 Hz), 2.55 (4H, t, J = 5 Hz), 2.44 (2H, t, J = 7 Hz), 1.57–1.80 (4H, m) (CDCl$_3$) | Element analysis (1) C$_{24}$H$_{30}$N$_4$O$_6$  C   H   N Cal. 63.15 6.11 11.33 value Meas. 62.74 6.13 11.24 value |
| 33 | 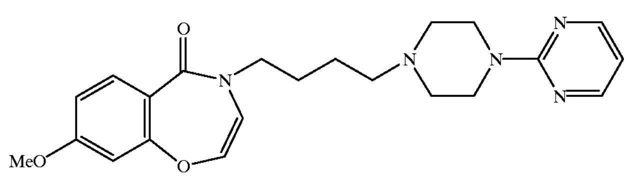 | 156–158° C. (1) (MeOH—Et$_2$O) | 3438 2947 2592 1716 1681 1612 1586 1553 1448 1366 1308 1278 1166 1118 (1) (KBr) | 8.29 (2H, d, J = 5 Hz), 7.82 (1H, d, J = 7 Hz), 6.72 (1H, d, J = 7 Hz), 6.46 (1H, s), 6.45 (1H, t, J = 5 Hz), 6.29 (1H, d, J = 5 Hz), 5.54 (1H, d, J = 5 Hz), 3.82 (3H, s), 3.82 (4H, t, J = 5 Hz), 3.65 (2H, t, J = 7 Hz), 2.50 (4H, t, J = 5 Hz), 2.43 (2H, t, J = 7 Hz), 1.49–1.78 (4H, m) (CDCl$_3$) | FAB-Mass 410 (M + H)$^+$ |

| Ex. | Chemical structure | m.p. (Recrystallization solvent) | IR (cm⁻¹) | NMR (δ ppm) | MS/Element analysis |
|---|---|---|---|---|---|
| 34 | 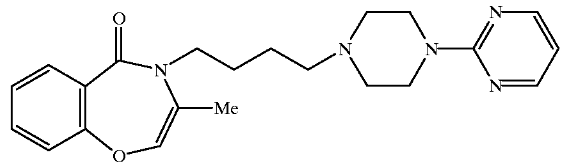 | 141–142° C. (1) (MeOH–Et₂O) | 3438 2956 1684 1634 1584 1482 1457 1307 (1) (KBr) | 8.33 (2H, d, J = 5 Hz), 7.69 (1H, d, J = 8 Hz), 7.48 (1H, t, J = 8 Hz), 7.23 (1H, t, J = 8 Hz), 7.05 (1H, d, J = 8 Hz), 6.55–6.60 (6H, m), 3.71–3.78 (6H, m), 2.43 (4H, t, J = 5 Hz), 2.38 (2H, t, J = 7 Hz), 1.81 (3H, s), 1.50–1.76 (4H, m) (1) (DMSO-d₆) | FAB-Mass 394 (M + H)⁺ |
| 35 | 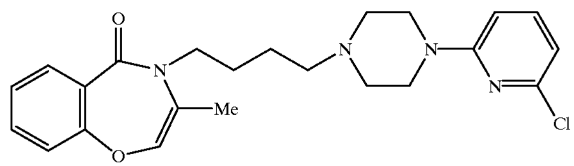 | 166–168° C. (1) (acetone-Et₂O) | 2934 2582 1685 1638 1591 1560 1458 1269 984 955 (1) (KBr) | 7.69 (1H, d, J = 8 Hz), 7.46–7.54 (2H, m), 7.23 (1H, t, J = 8 Hz), 7.06 (1H, d, J = 8 Hz), 6.75 (1H, d, J = 8 Hz), 6.64 (1H, s), 6.62 (4H, s), 6.56 (1H, s), 3.76 (2H, t, J = 7 Hz), 3.47 (4H, d, J = 4 Hz), 2.46 (4H, d, J = 4 Hz), 2.37 (2H, t, J = 4 Hz), 1.81 (3H, s), 1.52–1.59 (4H, m) (1) (DMSO-d₆) | FAB-Mass 427 (M + H)⁺ |
| 36 | 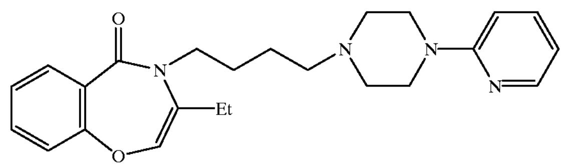 | amorphous (1) | 3444 2967 1698 1609 1542 1435 1252 972 793 (1) (KBr) | 8.18 (1H, d, J = 3 Hz), 7.85 (1H, d, J = 2 Hz), 7.45 (1H, t, J = 5 Hz), 7.38 (1H, t, J = 5 Hz), 7.17 (1H, t, J = 7 Hz), 6.98 (1H, d, J = 8 Hz), 6.63 (1H, d, J = 7 Hz), 6.59 (1H, t, J = 5 Hz), 6.44 (1H, s), 3.82–3.85 (2H, m), 3.51–3.57 (4H, m), 2.51–2.58 (4H, m), 2.42–2.45 (2H, m), 2.18 (2H, q, J = 8 Hz), 1.58–1.72 (4H, m), 0.96 (3H, t, J = 8 Hz) (CDCl₃) | FAB-Mass 407 (M + H)⁺ |
| 37 | 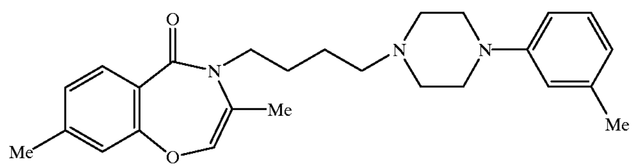 | 113–115° C. (1) (MeOH–Et₂O) | 3494 2959 1718 1624 1556 1496 1425 980 792 (1) (KBr) | 7.72 (1H, d, J = 8 Hz), 7.16 (1H, t, J = 7 Hz), 7.00 (1H, d, J = 8 Hz), 6.78 (1H, s), 6.75 (1H, s), 6.70 (1H, d, J = 9 Hz), 6.67 (1H, d, J = 9 Hz), 6.34 (1H, s), 3.82 (2H, t, J = 7 Hz), 3.18 (4H, t, J = 5 Hz), 2.58 (4H, t, J = 5 Hz), 2.43 (2H, t, J = 7 Hz), 2.35 (3H, s), 2.31 (3H, s), 1.80 (3H, s), 1.48–1.73 (4H, m) (CDCl₃) | FAB-Mass 420 (M + H)⁺ |
| 38 | 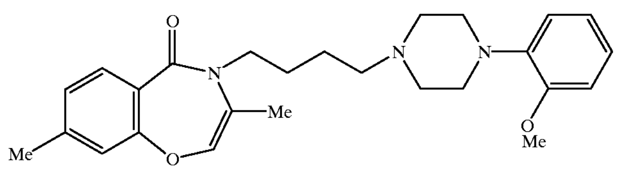 | 88–90° C. (1) (MeOH–Et₂O-hexane) | 3448 2923 2540 1708 1630 1496 1421 1353 983 (1) (KBr) | 7.72 (1H, d, J = 8 Hz), 6.90–7.93 (4H, m), 6.86 (1H, d, J = 8 Hz), 6.78 (1H, s), 6.34 (1H, s), 3.86 (3H, s), 3.81 (2H, t, J = 7 Hz), 3.05–3.16 (4H, m), 2.61–2.72 (4H, m), 2.46 (2H, t, J = 7 Hz), 2.34 (3H, s), 1.80 (3H, s), 1.53–1.77 (4H, m) (CDCl₃) | FAB-Mass 436 (M + H)⁺ |

-continued

| Ex. | Chemical structure | m.p. (Recrystallization solvent) | IR (cm⁻¹) | NMR (δ ppm) | MS/Element analysis |
|---|---|---|---|---|---|
| 39 | (structure: pyrimidine-OMe substituted) | 142–143° C. (1) (MeOH—Et$_2$O) | 3476 3408 2940 2504 1927 1710 1645 1586 1430 963 924 (1) (KBr) | 8.02 (1H, s), 7.63 (1H, s), 7.62 (1H, s), 7.18 (1H, d, J = 7 Hz), 6.87 (1H, d, J = 7 Hz), 6.36 (1H, s), 3.88 (3H, s), 3.83 (2H, t, J = 9 Hz), 3.56 (4H, t, J = 6 Hz), 2.54 (4H, t, J = 6 Hz), 2.44 (2H, t, J = 9 Hz), 2.33 (3H, s), 1.80 (3H, s), 1.56–1.78 (4H, m) (CDCl$_3$) | FAB-Mass 438 (M + H)⁺ |
| 40 | (structure: pyridine-NH$_2$, F substituted) | 243–245° C. (2) (MeOH—Et$_2$O) | 3356 3194 2948 2680 2602 1730 1685 1638 1583 1560 1540 1493 1432 1280 (2) (KBr) | 7.81 (1H, d, J = 3 Hz), 7.62 (1H, d, J = 3 Hz), 7.18 (1H, dd, J = 9 Hz, 3 Hz), 6.86 (1H, d, J = 9 Hz), 6.36 (1H, s), 4.76 (2H, br), 3.82 (2H, t, J = 7 Hz), 3.68 (4H, t, J = 5 Hz), 2.38–2.49 (6H, m), 2.33 (3H, s), 1.79 (3H, s), 1.55–1.72 (4H, m) (CDCl$_3$) | FAB-Mass 441 (M + H)⁺ |
| 41 | (structure: chlorophenyl substituted) | 164–166° C. (1) (MeOH—Et$_2$O) | 3433 3400 2918 2590 1680 1638 1592 1560 1486 1448 1397 1346 1268 1166 (1) (KBr) | 7.51 (1H, m), 7.37 (1H, t, J = 8 Hz), 7.08 (1H, m), 6.94 (1H, m), 6.58 (1H, d, J = 7 Hz), 6.46 (1H, d, J = 8 Hz), 6.37 (1H, s), 3.82 (2H, m), 3.54 (4H, m), 2.51 (4H, m), 2.42 (2H, m), 1.81 (3H, s), 1.52–1.73 (4H, m) (CDCl$_3$) | FAB-Mass 445 (M + H)⁺ |
| 42 | (structure: 3-methylphenyl substituted) | 149–151° C. (1) (MeOH—Et$_2$O) | 2947 1684 1640 1486 1431 1347 1256 1176 1116 988 778 (1) (KBr) | 7.52 (1H, dd, J = 3 Hz, 9 Hz), 7.05–7.18 (2H, m), 6.94 (1H, dd, J = 5 Hz, 9 Hz), 6.75 (1H, s), 6.69 (2H, m), 6.36 (1H, t, J = 1 Hz), 3.82 (2H, t, J = 7 Hz), 3.18 (4H, t, J = 5 Hz), 2.59 (4H, t, J = 7 Hz), 2.44 (2H, t, J = 7 Hz), 2.31 (3H, s), 1.81 (3H, d, J = 1 Hz), 1.65 (4H, m) (CDCl$_3$) | Element analysis (1) C$_{23}$H$_{24}$FN$_3$O$_5$<br>C H N<br>Cal. 64.55 6.35 7.79 value<br>Meas. 64.38 6.44 7.74 value |
| 43 | (structure: phenyl substituted) | 208–210° C. (1) (MeOH—CHCl$_3$—Et$_2$O) | 3428 2938 2602 1718 1639 1496 1394 1250 (1) (KBr) | 7.63 (1H, s), 7.21–7.28 (2H, m), 7.18 (1H, d, J = 8 Hz), 6.88–6.93 (2H, m), 6.82–6.85 (2H, m), 6.35 (1H, s), 3.79 (2H, t, J = 7 Hz), 3.19 (4H, t, J = 5 Hz), 2.58 (4H, t, J = 7 Hz), 2.39 (2H, t, J = 7 Hz), 2.33 (3H, s), 1.79 (3H, s), 1.52–1.71 (4H, m), 1.38–1.47 (2H, m) (CDCl$_3$) | FAB-Mass 420 (M + H)⁺ |

| Ex. | Chemical structure | m.p. (Recrystallization solvent) | IR (cm⁻¹) | NMR (δ ppm) | MS/Element analysis |
|---|---|---|---|---|---|
| 44 | (structure) | 228–230° C. (1) (MeOH–CHCl₃–Et₂O) | 3438 2948 2587 1676 1582 1554 982 (1) (KBr) | 8.29 (2H, d, J = 5 Hz), 7.62 (1H, s), 7.16 (1H, d, J = 8 Hz), 6.85 (1H, d, J = 8 Hz), 6.46 (1H, t, J = 5 Hz), 6.35 (1H, s), 3.76–3.83 (6H, m), 2.48 (4H, m), 2.36 (2H, t, J = 8 Hz), 2.33 (3H, s), 1.79 (3H, s), 1.65 (2H, m), 1.55 (2H, m), 1.42 (2H, m) (CDCl₃) | MAB-Mass 422 (M + H)⁺ |
| 45 | (structure) | 178–180° C. (2) (EtOH–Et₂O) | 3698 2934 2572 2458 1662 1605 1594 1480 1586 1478 1456 1362 1201 (2) (KBr) | 10.1 (1H, brs), 8.44 (2H, d, J = 5 Hz), 7.78–7.81 (1H, m), 7.61 (1H, t, J = 7 Hz), 7.33–7.37 (1H, m), 7.18 (1H, s), 7.16 (1H, d, J = 9 Hz), 6.76 (1H, t, J = 5 Hz), 4.69–4.73 (2H, m), 3.85–3.89 (2H, m), 3.05–3.60 (8H, m), 2.11–2.20 (2H, m) (DMSO-d₆) | MAB-Mass 400 (M + H)⁺ |
| 46 | (structure) | 158–161° C. (1) (EtOH–iPr₂O) | 3430 2949 1704 1657 1594 1480 1455 1438 1247 1158 984 (1) (KBr) | 8.08–8.11 (1H, m), 7.77–7.81 (1H, m), 7.48–7.63 (2H, m), 7.33 (1H, t, J = 7 Hz), 7.17 (1H, d, J = 7 Hz), 7.16 (1H, s), 6.80 (1H, d, J = 9 Hz), 6.61 (4H, s), 6.60–6.65 (1H, m), 3.85 (2H, t, J = 7 Hz), 3.47 (4H, t, J = 5 Hz), 2.44–2.50 (4H, m), 2.40 (2H, t, J = 7 Hz), 1.62–1.72 (2H, m), 1.48–1.58 (2H, m) (1) (DMSO-d₆) | Element analysis (1) C₂₆H₂₉N₃O₆Cl<br>    C    H    N<br>Cal. 59.03 5.53 10.59<br>value<br>Meas. 58.70 5.54 10.50<br>value |
| 47 | (structure) | 219–222° C. (2) (acetone) | 3448 1654 1608 1570 1546 1474 1450 1353 1100 (2) (KBr) | 11.33 (1H, br.s), 8.92 (1H, d, J = 5 Hz), 8.21 (1H, d, J = 8 Hz), 8.04 (1H, t, J = 8 Hz), 7.96 (1H, d, J = 8 Hz), 7.78–7.80 (1H, m), 7.73 (1H, t, J = 8 Hz), 7.58–7.62 (1H, m), 7.34 (1H, t, J = 7 Hz), 7.16 (2H, t, J = 7 Hz), 4.74 (2H, d, J = 11 Hz), 3.99 (2H, br.s), 3.86 (2H, t, J = 7 Hz), 3.64 (2H, d, J = 11 Hz), 3.17–3.28 (4H, m), 1.70–1.81 (4H, m) (2) (DMSO-d₆) | FAB-Mass 464 (M + H)⁺ |
| 48 | (structure) | 133–135° C. (3) (MeOH–CHCl₃–Et₂O) | 3450 2872 1664 1621 1568 1414 1300 1095 986 (3) (KBr) | 8.17 (1H, d, J = 5 Hz), 7.82 (1H, d, J = 9 Hz), 7.46 (1H, t, J = 9 Hz), 7.22 (1H, d, J = 8 Hz), 7.05 (1H, s), 6.69 (1H, s), 6.58–6.64 (2H, m), 3.92 (2H, t, J = 7 Hz), 3.54 (4H, t, J = 5 Hz), 2.54 (4H, t, J = 5 Hz), 2.43 (2H, t, J = 7 Hz), 1.70–1.79 (2H, m), 1.55–1.64 (2H, m)(CDCl₃) | FAB-Mass 447 (M + H)⁺ |

-continued

| Ex. | Chemical structure | m.p. (Recrystallization solvent) | IR (cm$^{-1}$) | NMR (δ ppm) | MS/Element analysis |
|---|---|---|---|---|---|
| 49 | (structure) | 100–101° C. (3) (Et$_2$O) | 3434 2918 2593 1700 1622 1586 1552 1490 1227 954 (3) (KBr) | 8.29 (2H, d, J = 5 Hz), 7.66 (1H, s), 7.23 (1H, d, J = 8 Hz), 6.89 (1H, d, J = 8 Hz), 6.70 (1H, s), 6.46 (1H, t, J = 5 Hz), 3.92 (2H, t, J = 7 Hz), 3.82 (4H, t, J = 5 Hz), 2.49 (4H, t, J = 5 Hz), 2.42 (2H, t, J = 7 Hz), 2.33 (3H, s), 1.72–1.81 (2H, m), 1.55–1.69 (2H, m) (CDCl$_3$) | FAB-Mass 428 (M+ H)$^+$ |
| 50 | (structure) | 137–140° C. (1) (acetone-Et$_2$O) | 2934 2358 1718 1644 1586 1490 1432 1363 1040 984 (1) (KBr) | 8.35 (2H, t, J = 5 Hz), 7.18 (1H, s), 7.14 (1H, d, J = 3 Hz), 7.04–7.10 (1H, m), 6.62 (1H, s), 6.61–6.86 (4H, m), 5.67 (1H, s), 5.59 (1H, s), 4.03–4.07 (4H, m), 3.77 (3H, s), 3.73–3.78 (4H, m), 3.48–3.60 (1H, m), 2.40–2.50 (6H, m), 1.64–1.72 (2H, m), 1.53–1.62 (2H, m) (DMSO-d$_6$) | FAB-Mass 458 (M+ H)$^+$ |
| 51 | (structure) | 179–181° C. (1) (acetone-Et$_2$O) | 3438 2942 1718 1654 1638 1585 1455 1364 1310 1096 984 (1) (KBr) | 8.33 (2H, d, J = 5 Hz), 7.61 (1H, d, J = 8 Hz), 7.45 (1H, t, J = 8 Hz), 7.19 (1H, t, J = 8 Hz), 7.06 (1H, d, J = 8 Hz), 6.59–6.62 (1H, m), 6.62 (4H, s), 5.68 (1H, s), 5.40 (1H, s), 5.38 (1H, s), 4.01–4.08 (1H, m), 3.72–3.74 (4H, m), 3.60 (3H, s), 3.43–3.49 (1H, m), 2.50–2.67 (4H, m), 2.44 (2H, t, J = 5 Hz), 1.60–1.67 (2H, m), 1.52–1.59 (2H, m) (1) (DMSO-d$_6$) | FAB-Mass 424 (M + H)$^+$ |
| 52 | (structure) | 126–129° C. (1) (acetone-Et$_2$O) | 3417 2936 2597 1700 1684 1637 1508 1478 1437 1034 (1) (KBr) | 8.09–8.10 (1H, m), 7.60–7.62 (1H, m), 7.43–7.53 (2H, m), 7.19 (1H, t, J = 8 Hz), 7.06 (1H, d, J = 8 Hz), 6.79 (1H, d, J = 9 Hz), 6.60–6.63 (1H, m), 6.62 (4H, s), 5.68 (1H, s), 5.40 (1H, s), 5.37 (1H, s), 4.02–4.09 (1H, m), 3.60 (3H, s), 3.46–3.49 (4H, m), 3.29–3.40 (1H, m), 2.48–2.51 (4H, m), 2.40 (2H, t, J = 7 Hz), 1.61–1.67 (2H, m), 1.51–1.59 (2H, m) (1) (DMSO-d$_6$) | FAB-Mass 423 (M + H)$^+$ |
| 53 | (structure) | 152–155° C. (1) (acetone-Et$_2$O) | 2930 2592 1680 1637 1455 1424 1209 (1) (KBr) | 8.75 (2H, d, J = 5 Hz), 7.69 (1H, d, J = 8 Hz), 7.49 (1H, t, J = 8 Hz), 7.30 (1H, t, J = 5 Hz), 7.22 (1H, t, J = 8 Hz), 7.15 (1H, brs), 7.05 (1H, d, J = 8 Hz), 6.61 (4H, s), 6.56 (1H, s), 3.74–3.76 (2H, m), 3.21–3.25 (4H, m), 2.61–2.67 (4H, m), 1.81 (3H, s), 1.57–1.59 (4H, m) (1) (DMSO-d$_6$) | FAB-Mass 391 (M+ H)$^+$ |

-continued

| Ex. | Chemical structure | m.p. (Recrystallization solvent) | IR (cm⁻¹) | NMR (δ ppm) | MS/Element analysis |
|---|---|---|---|---|---|
| 54 | 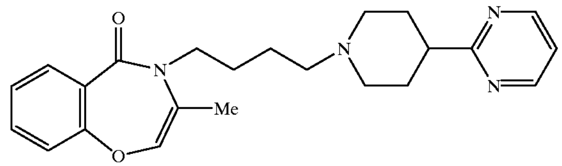 | 128–131° C. (1) (acetone-Et₂O) | 2958 1718 1700 1684 1633 1564 1458 1296 1211 (1) (KBr) | 8.74 (2H, d, J = 5 Hz), 7.69 (1H, d, J = 8 Hz), 7.49 (1H, t, J = 8 Hz), 7.34 (1H, t, J = 5 Hz), 7.24 (1H, t, J = 8 Hz), 7.06 (1H, d, J = 8 Hz), 6.60 (4H, s), 6.58 (1H, s), 3.73–3.77 (2H, s), 3.16–3.18 (2H, m), 2.90–2.94 (1H, m), 2.66 (2H, brs), 2.48–2.51 (2H, m), 2.00–2.03 (2H, m), 1.90–1.93 (2H, m),1.82 (3H, s), 1.59–1.62 (4H, m) (1) (DMSO-d₆) | FAB-Mass 393 (M + H)⁺ |
| 55 | 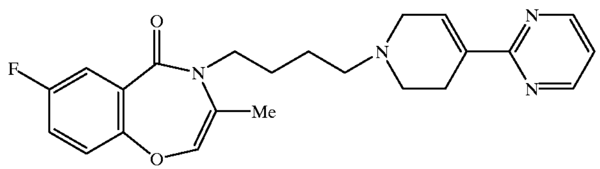 | 200–203° C. (1) (MeOH–Et₂O) | 3534 2927 1631 1558 1487 1429 1179 (1) (KBr) | 8.68 (2H, d, J = 5 Hz), 7.47–7.49 (1H, m), 7.18 (1H, s), 7.05–7.12 (2H, m), 6.92–6.95 (1H, m), 6.39 (1H, s), 3.85 (2H, t, J = 7 Hz), 3.54 (2H, m), 3.40–3.15 (2H, m), 3.02–3.07 (1H, m), 2.85–2.95 (2H, m), 1.82 (3H, s), 1.74–1.92 (4H, m) (CDCl₃) | FAB-Mass 409 (M + H)⁺ |
| 56 | 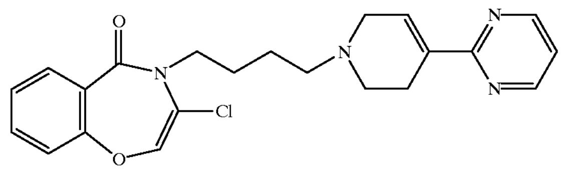 | 147–151° C. (2) (MeOH-acetone) | 3394 2930 1661 1605 1453 1422 1379 1200 (2) (KBr) | 10.15 (1H, brs), 8.82 (2H, d, J = 5 Hz), 7.79 (1H, d, J = 8 Hz), 7.60 (1H, t, J = 8 Hz), 7.33–7.43 (2H, m), 7.13–7.14 (3H, m), 4.09–4.13 (1H, m), 3.85–3.88 (3H, m), 3.65–3.70 (1H, m), 3.24–3.27 (3H, m), 2.85–2.99 (2H, m), 1.10–1.85 (4H, m) (2) (DMSO-d₆) | FAB-Mass 411 (M + H)⁺ |
| 57 | 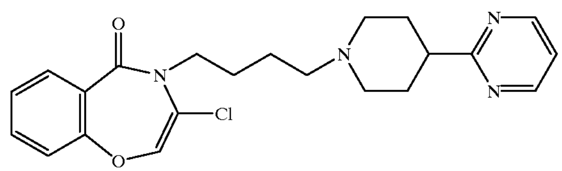 | 110–113° C. (2) (acetone) | 3051 2946 1646 1604 1564 1478 1456 1426 (2) (KBr) | 10.15 (1H, brs), 8.78 (2H, d, J = 5 Hz), 7.80 (1H, d, J = 8 Hz), 7.58–7.62 (1H, m), 7.33–7.40 (2H, m), 7.14–7.17 (2H, m), 3.84–3.87 (2H, m), 3.54–3.57 (2H, m), 3.03–3.15 (5H, m), 2.05–2.20 (4H, m), 1.66–1.85 (4H, m) (2) (DMSO-d₆) | FAB-Mass 413 (M + H)⁺ |
| 58 | 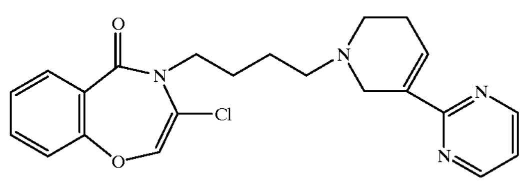 | 124–126° C. (1) (acetone) | 2926 2576 1699 1649 1560 1478 1422 1378 (1) (KBr) | 8.73 (2H, d, J = 5 Hz), 7.78 (1H, d, J = 8 Hz), 7.58 (1H, t, J = 7 Hz), 7.29–7.34 (2H, m), 7.23 (1H, s), 7.11–7.15 (2H, m), 6.60 (4H, s), 3.84–3.89 (2H, m), 3.42–3.51 (2H, m), 2.59–2.62 (4H, m), 2.31–2.40 (2H, m), 1.61–1.70 (4H, m) (1) (DMSO-d₆) | FAB-Mass 411 (M + H)⁺ |

-continued

| Ex. | Chemical structure | m.p. (Recrystallization solvent) | IR (cm⁻¹) | NMR (δ ppm) | MS/Element analysis |
|---|---|---|---|---|---|
| 59 | 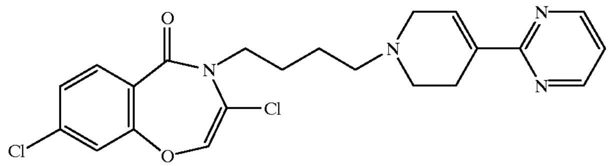 | 181–183° C. (1) (MeOH–Et₂O) | 3014 2539 1716 1658 1598 1556 1416 1298 (1) (KBr) | 8.67 (2H, d, J = 5 Hz), 7.82 (1H, d, J = 7 Hz), 7.26–7.27 (1H, m), 7.22 (1H, dd, J = 2 Hz, 7 Hz), 7.05 (1H, d, J = 2 Hz), 7.01 (1H, t, J = 5 Hz), 6.70 (1H, s), 3.92 (2H, t, J = 7 Hz), 3.25–3.29 (2H, m), 2.69–2.80 (4H, m), 2.55 (2H, t, J = 7 Hz), 1.66–1.75 (4H, m) (CDCl₃) | FAB-Mass 445 (M + H)⁺ |
| 60 | 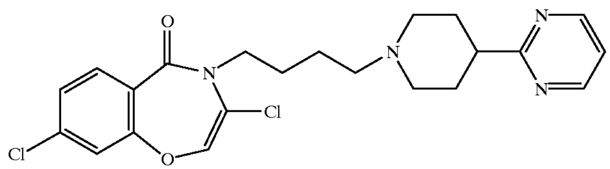 | amorphous (1) | 2926 1661 1619 1562 1429 (1) (KBr) | 8.74 (2H, d, J = 5 Hz), 7.80 (1H, d, J = 9 Hz), 7.41 (1H, d, J = 9 Hz), 7.33 (1H, t, J = 5 Hz), 7.29 (1H, s), 7.11 (1H, s), 6.59 (4H, s), 3.82–3.89 (2H, m), 3.15–3.21 (2H, m), 2.91–2.99 (1H, m), 2.67–2.72 (2H, m), 2.50–2.59 (2H, m), 1.90–2.08 (4H, m), 1.61–1.72 (4H, m) (DMSO-d₆) | FAB-Mass 447 (M + H)⁺ |
| 61 | 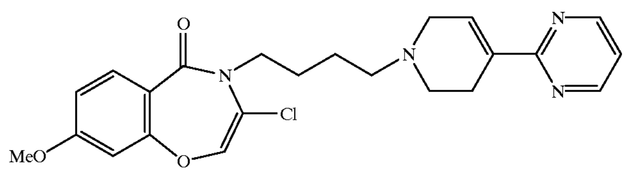 | 110–112° C. (1) (Et₂O) | 2925 1657 1647 1616 1560 1540 1422 1328 (1) (KBr) | 8.76 (2H, d, J = 5 Hz), 7.72 (1H, d, J = 9 Hz), 7.32 (1H, t, J = 5 Hz), 7.14–7.16 (1H, m), 7.07 (1H, d, J = 2 Hz), 6.89 (1H, d, J = 2 Hz), 6.69 (1H, d, J = 2 Hz), 6.62 (4H, s), 3.81–3.83 (5H, m), 3.33–3.37 (2H, m), 2.78–2.85 (2H, m), 2.63–2.67 (4H, m), 1.60–1.68 (4H, m) (DMSO-d₆) | FAB-Mass 441 (M + H)⁺ |
| 62 | 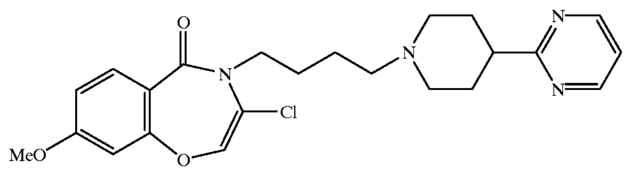 | 178–181° C. (1) (acetone-Et₂O) | 2926 1665 1609 1561 1428 1264 (1) (KBr) | 8.76 (2H, d, J = 3 Hz), 7.73 (1H, d, J = 9 Hz), 7.38 (1H, t, J = 3 Hz), 7.09 (1H, d, J = 4 Hz), 6.90–6.92 (1H, m), 6.70 (1H, s), 6.63 (4H, s), 3.80–3.85 (5H, m), 3.52–3.57 (2H, m), 3.05–3.18 (5H, m), 2.16–2.20 (2H, m), 1.95–2.05 (2H, m), 1.63–1.72 (4H, m) (DMSO-d₆) | FAB-Mass 443 (M + H)⁺ |
| 63 | 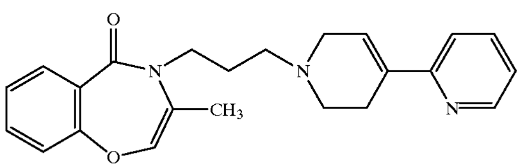 | 155–158° C. (1) (acetone-Et₂O) | 3441 2950 2681 2589 1680 1634 1605 1458 1397 (1) (KBr) | 8.56 (1H, d, J = 4 Hz), 7.80 (1H, t, J = 7 Hz), 7.71 (1H, d, J = 8 Hz), 7.61 (1H, d, J = 8 Hz), 7.51 (1H, t, J = 7 Hz), 7.30 (1H, t, J = 6 Hz), 7.25 (1H, t, J = 7 Hz), 7.06 (1H, d, J = 8 Hz), 6.69 (1H, s), 6.63 (4H, s), 6.59 (1H, s), 3.75–3.95 (4H, m), 3.20–3.45 (2H, m), 3.02–3.18 (2H, m), 2.79–2.89 (2H, m), 1.92–2.08 (2H, m), 1.85 (3H, s) (1) (DMSO-d₆) | FAB-Mass 376 (M + H)⁺ |

-continued

| Ex. | Chemical structure | m.p. (Recrystallization solvent) | IR (cm⁻¹) | NMR (δ ppm) | MS/Element analysis |
|---|---|---|---|---|---|
| 64 | 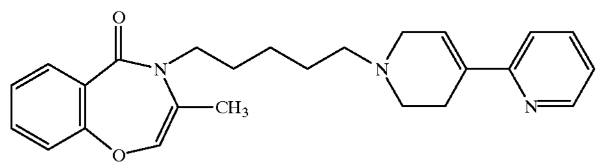 | amorphous (1) | 3422 2943 1680 1631 1457 1400 1349 1293 (1) (KBr) | 8.51 (1H, d, J = 8 Hz), 7.66–7.79 (2H, m), 7.42–7.55 (2H, m), 7.16–7.28 (2H, m), 7.03 (1H, d, J = 8 Hz), 6.65 (1H, s), 6.60 (4H, s), 6.54 (1H, s), 3.68–3.79 (2H, m), 3.21–3.30 (2H, m), 2.70–2.81 (2H, m), 2.45–2.65 (4H, m), 1.80 (3H, s), 1.50–1.64 (4H, m), 1.30–1.43 (2H, m) (1) (DMSO-d₆) | FAB-Mass 404 (M + H)⁺ |
| 65 | 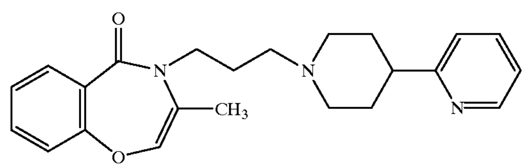 | amorphous (1) | 3433 2934 1682 1634 1457 1400 1350 1208 (1) (KBr) | 8.49 (1H, d, J = 4 Hz), 7.69–7.72 (2H, m), 7.49 (1H, t, J = 8 Hz), 7.26 (1H, t, J = 7 Hz), 7.18–7.22 (2H, m), 7.06 (1H, d, J = 8 Hz), 6.60 (4H, s), 6.56 (1H, s), 3.77 (2H, t, J = 7 Hz), 3.04–3.10 (2H, m), 2.64–2.76 (1H, m), 2.40–2.52 (4H, m), 2.20 (2H, t, J = 11 Hz), 1.83 (3H, s), 1.71–1.91 (4H, m) (1) (DMSO-d₆) | FAB-Mass 378(M + H)⁺ |
| 66 | 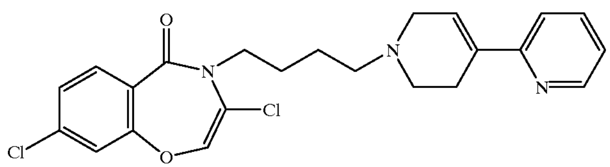 | 167–170° C. (1) (MeOH—Et₂O) | 3432 2946 1660 1600 1567 1470 1414 1331 1201 (1) (KBr) | 8.51 (1H, d, J = 4 Hz), 7.80 (1H, d, J = 8 Hz), 7.73 (1H, t, J = 8 Hz), 7.51 (1H, d, J = 8 Hz), 7.40 (1H, d, J = 9 Hz), 7.30 (1H, s), 7.21 (1H, t, J = 6 Hz), 7.12 (1H, s), 6.65 (1H, s), 6.62 (4H, s), 3.85 (2H, t, J = 7 Hz), 3.19–3.25 (2H, m), 2.70–2.77 (2H, m), 2.52–2.63 (4H, m), 1.64–1.73 (2H, m),1.53–1.64 (2H, m) (1) (DMSO-d₆) | FAB-Mass 444 (M + H)⁺ |
| 67 | 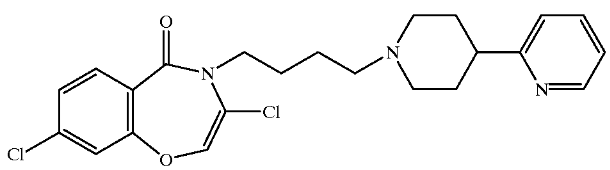 | 161–164° C. (1) (MeOH—Et₂O) | 3427 2947 1662 1599 1569 1475 1436 1289 1243 (1) (KBr) | 8.48 (1H, d, J = 4 Hz), 7.80 (1H, d, J = 8 Hz), 7.69 (1H, t, J = 4 Hz), 7.41 (1H, dd, J = 2 Hz, 8 Hz), 7.30 (1H, d, J = 2 Hz), 7.25 (1H, d, J = 8 Hz), 7.18 (1H, t, J = 4 Hz), 7.13 (1H, s), 6.59 (4H, s), 3.85 (2H, t, J = 7 Hz), 3.06 (2H, d, J = 10 Hz), 2.68–2.72 (1H, m), 2.45–2.55 (2H, m), 2.14–2.25 (2H, m), 1.76–1.86 (4H, m), 1.62–1.68 (2H, m), 1.53–1.61 (2H, m) (1) (DMSO-d₆) | FAB-Mass 446 (M + H)⁺ |
| 68 | 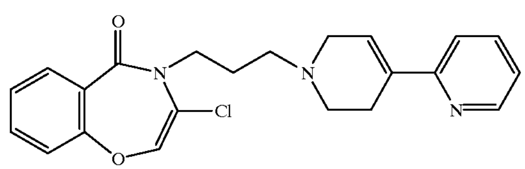 | 148–151° C. (MeOH—Et₂O) | 3420 2920 1662 1604 1454 1372 1332 1278 (1) (KBr) | 8.51 (1H, d, J = 5 Hz), 7.79 (1H, d, J = 8 Hz), 7.73 (1H, t, J = 8 Hz), 7.57 (1H, t, J = 8 Hz), 7.50 (1H, d, J = 8 Hz), 7.32 (1H, t, J = 8 Hz), 7.21 (1H, t, J = 4 Hz), 7.14 (1H, t, J = 8 Hz), 7.09 (1H, s), 6.67 (1H, s), 6.62 (4H, s), 3.88 (2H, t, J = 7 Hz), 2.70 (2H, t, J = 6 Hz), 2.51–2.59 (6H, m), 1.87–1.93 (2H, m) (1) (DMSO-d₆) | FAB-Mass 396 (M + H)⁺ |

| Ex. | Chemical structure | m.p. (Recrystallization solvent) | IR (cm⁻¹) | NMR (δ ppm) | MS/Element analysis |
|---|---|---|---|---|---|
| 69 | (3-chloro-benzoxazepinone with propyl-N-piperidine-4-(2-pyridyl)) | amorphous (1) | 3440 2947 2656 2351 1651 1455 1336 1201 (1) (KBr) | 8.48 (1H, d, J = 4 Hz), 7.79 (1H, d, J = 7 Hz), 7.69 (1H, t, J = 8 Hz), 7.58 (1H, t, J = 7 Hz), 7.33 (1H, t, J = 8 Hz), 7.25 (1H, d, J = 8 Hz), 7.14–7.20 (2H, m), 7.10 (1H, s), 6.61 (4H, s), 3.87 (2H, t, J = 6 Hz), 3.08 (2H, d, J = 11 Hz), 2.67–2.70 (1H, m), 2.23 (2H, t, J = 10 Hz), 1.79–1.88 (6H, m) (1) (DMSO-d₆) | FAB-Mass 398 (M + H)⁺ |
| 70 | (3-chloro-benzoxazepinone with pentyl-N-piperidine-4-(2-pyridyl)) | 123–126° C. (1) (MeOH–Et₂O) | 3441 2942 1655 1604 1454 1377 1329 1247 (1) (KBr) | 8.51 (1H, d, J = 4 Hz), 7.78 (1H, d, J = 8 Hz), 7.73 (1H, t, J = 7 Hz), 7.57 (1H, t, J = 7 Hz), 7.49 (1H, d, J = 8 Hz), 7.32 (1H, t, J = 8 Hz), 7.22 (1H, t, J = 4 Hz), 7.13 (1H, d, J = 8 Hz), 7.11 (1H, s), 6.64 (1H, s), 3.83 (2H, t, J = 7 Hz), 3.19–3.22 (2H, m), 2.70 (2H, t, J = 6 Hz), 2.59–2.63 (2H, m), 2.49–2.58 (2H, m), 1.64–1.75 (2H, m), 1.55–1.63 (2H, m), 1.35–1.45 (2H, m) (1) (DMSO-d₆) | FAB-Mass 424 (M + H)⁺ |
| 71 | (benzoxazepinone with propyl-N-tetrahydropyridine-4-(2-pyridyl)) | amorphous (1) | 3434 2936 1680 1638 1456 1417 1383 1310 1199 (1) (KBr) | 8.51 (1H, d, J = 4 Hz), 7.71–7.76 (2H, m), 7.49–7.53 (1H, m), 7.20–7.25 (2H, m), 7.04 (1H, d, J = 7 Hz), 6.66 (1H, s), 6.61 (4H, s), 6.50 (1H, d, J = 4 Hz), 5.95 (1H, d, J = 4 Hz), 3.64 (2H, t, J = 7 Hz), 3.21–3.24 (2H, m), 2.73 (2H, t, J = 6 Hz), 2.55–2.63 (4H, m), 1.56–1.65 (4H, m) (1) (DMSO-d₆) | FAB-Mass 376 (M + H)⁺ |
| 72 | (benzoxazepinone with butyl-N-piperidine-4-(2-pyridyl)) | 155–158° C. (1) (MeOH–Et₂O) | 3426 2944 1680 1639 1572 1456 1417 1311 1199 (1) (KBr) | 8.48 (1H, d, J = 4 Hz), 7.67–7.75 (2H, m), 7.49–7.53 (1H, m), 7.23–7.27 (2H, m), 7.17–7.22 (1H, m), 7.04 (1H, d, J = 7 Hz), 6.58 (4H, s), 6.51 (1H, d, J = 4 Hz), 5.95 (1H, d, J = 4 Hz), 3.63 (2H, t, J = 7 Hz), 3.08–3.11 (2H, m), 2.68–2.74 (1H, m), 2.49–2.56 (2H, m), 2.23–2.28 (2H, m), 1.76–1.87 (4H, m), 1.54–1.67 (4H, m) (1) (DMSO-d₆) | FAB-Mass 378 (M + H)⁺ |
| 73 | (benzoxazepinone with pentyl-N-tetrahydropyridine-4-(2-pyridyl)) | amorphous (1) | 3432 2938 1706 1684 1638 1604 1571 1456 1415 1296 (1) (KBr) | 8.52 (1H, d, J = 4 Hz), 7.72–7.76 (2H, m), 7.48–7.53 (2H, m), 7.21–7.24 (2H, m), 7.03 (1H, d, J = 8 Hz), 6.66 (1H, s), 6.60 (4H, s), 6.48 (1H, d, J = 4 Hz), 5.94 (1H, d, J = 4 Hz), 3.61 (2H, t, J = 7 Hz), 3.25–3.34 (2H, m), 2.80–2.82 (2H, m), 2.57–2.62 (4H, m), 1.57–1.67 (4H, m), 1.32–1.40 (2H, m) (1) (DMSO-d₆) | FAB-Mass 390 (M + H)⁺ |

| Ex. | Chemical structure | m.p. (Recrystallization solvent) | IR (cm$^{-1}$) | NMR (δ ppm) | MS/Element analysis |
|---|---|---|---|---|---|
| 74 | (3-methyl-benzoxazepinone with 7-methyl, N-butyl linker to 4-(2-pyridyl)-tetrahydropyridine) | amorphous (1) | 3438 2930 1679 1636 1492 1467 1421 1392 1285 (1) (KBr) | 8.51 (1H, d, J = 4 Hz), 7.74 (1H, t, J = 8 Hz), 7.47–7.53 (1H, m), 7.21–7.29 (2H, m), 6.94 (1H, d, J = 8 Hz), 6.66 (1H, s), 6.61 (4H, s), 6.54 (1H, s), 3.69–3.78 (2H, m), 3.20–3.25 (2H, m), 2.69–2.75 (2H, m), 2.52–2.65 (4H, m), 2.29 (3H, s), 1.79 (3H, s), 1.53–1.62 (4H, m) (1) (DMSO-d$_6$) | FAB-Mass 404 (M + H)$^+$ |
| 75 | (analog with N-butyl linker) | amorphous (1) | 3438 2948 1678 1633 1492 1421 1384 1349 1292 (1) (KBr) | 8.49 (1H, d, J = 4 Hz), 7.70–7.73 (1H, m), 7.48 (1H, s), 7.25–7.29 (2H, m), 7.18–7.21 (2H, m), 6.93 (1H, d, J = 8 Hz), 6.60 (4H, s), 6.54 (1H, s), 3.75 (1H, t, J = 6 Hz), 3.17–3.20 (2H, m), 2.75–2.80 (1H, m), 2.64–2.68 (2H, m), 2.43–2.49 (2H, m), 2.29 (3H, s), 1.84–1.89 (4H, m), 1.80 (3H, s), 1.58–1.65 (4H, m) (1) (DMSO-d$_6$) | FAB-Mass 406 (M + H)$^+$ |
| 76 | (analog with N-pentyl linker) | amorphous (1) | 3438 2951 1711 1638 1492 1422 1385 1347 1288 (1) (KBr) | 8.50 (1H, d, J = 4 Hz), 7.70–7.74 (1H, m), 7.47 (1H, s), 7.26–7.28 (2H, m), 7.21–7.23 (2H, m), 6.94 (1H, d, J = 8 Hz), 6.59 (4H, s), 6.55 (1H, s), 3.72 (2H, t, J = 7 Hz), 3.22–3.26 (2H, m), 2.76–2.85 (1H, m), 2.68–2.75 (2H, m), 2.50–2.65 (2H, m), 2.29 (3H, s), 1.85–1.95 (4H, m), 1.79 (3H, s), 1.55–1.65 (4H, m), 1.30–1.41 (2H, m) (1) (DMSO-d$_6$) | FAB-Mass 420 (M + H)$^+$ |
| 77 | (7-methoxy benzoxepinone with N-pentyl linker to 4-(2-pyridyl)-tetrahydropyridine) | amorphous (1) | 3431 2942 1684 1612 1500 1444 1407 1383 1272 (1) (KBr) | 8.52 (1H, d, J = 4 Hz), 7.73–7.77 (1H, m), 7.69 (1H, d, J = 9 Hz), 7.52 (1H, d, J = 8 Hz), 7.22–7.25 (1H, m), 6.80 (1H, dd, J = 2 Hz, 9 Hz), 6.67 (1H, s), 6.60 (4H, s), 6.58 (1H, d, J = 2 Hz), 6.45 (1H, d, J = 4 Hz), 5.93 (1H, d, J = 4 Hz), 3.79 (1H, s), 3.58 (2H, t, J = 7 Hz), 3.23–3.28 (2H, m), 2.73–2.79 (2H, m), 2.58–2.62 (2H, m), 2.50–2.56 (2H, m), 1.54–1.65 (4H, m), 1.30–1.39 (2H, m) (1) (DMSO-d$_6$) | FAB-Mass 420 (M + H)$^+$ |
| 78 | (7-methoxy benzoxepinone analog with N-hexyl linker) | amorphous (1) | 3422 2941 1684 1612 1569 1436 1407 1385 1262 (1) (KBr) | 8.49 (1H, d, J = 4 Hz), 7.69–7.74 (1H, m), 7.68 (1H, d, J = 9 Hz), 7.27 (1H, d, J = 8 Hz), 7.20–7.23 (1H, m), 6.80 (1H, dd, J = 2 Hz, 9 Hz), 6.58 (4H, s), 6.45 (1H, d, J = 4 Hz), 5.92 (1H, d, J = 4 Hz), 3.80 (3H, s), 3.58 (2H, t, J = 7 Hz), 3.17–3.23 (2H, m), 2.74–2.82 (2H, m), 2.60–2.67 (2H, m), 2.41–2.52 (2H, m), 1.83–1.94 (4H, m), 1.55–1.65 (4H, m), 1.29–1.38 (2H, m) (1) (DMSO-d$_6$) | FAB-Mass 422 (M + H)$^+$ |

-continued

| Ex. | Chemical structure | m.p. (Recrystallization solvent) | IR (cm$^{-1}$) | NMR (δ ppm) | MS/Element analysis |
|---|---|---|---|---|---|
| 79 | [structure: MeO-benzoxazepinone-N-propyl-piperidine-pyridine] | amorphous (1) | 3421 2940 2685 1684 1612 1436 1277 (1) (KBr) | 8.51 (1H, d, J = 4 Hz), 7.72–7.76 (1H, m), 7.69 (1H, m), 6.82 (1H, dd, J = 2 Hz, 9 Hz), 6.62 (4H, s), 6.59 (1H, d, J = 2 Hz), 6.49 (1H, d, J = 4 Hz), 5.96 (1H, d, J = 4 Hz), 3.81 (3H, s), 3.65 (2H, t, J = 7 Hz), 3.43–3.48 (2H, m), 3.19–3.28 (1H, m), 2.85–3.02 (4H, m), 1.92–2.05 (6H, m) (1) (DMSO-d$_6$) | FAB-Mass 394 (M + H)$^+$ |
| 80 | [structure: Cl-benzoxazepinone-N-butyl-tetrahydropyridine-methylpyridine] | 121–124° C. (1) (MeOH–Et$_2$O) | 3424 2940 2582 1655 1578 1454 1372 1330 1249 (1) (KBr) | 8.63 (1H, d, J = 5 Hz), 7.78–7.80 (1H, m), 7.58–7.62 (1H, m), 7.34 (1H, t, J = 8 Hz), 7.25 (1H, d, J = 5 Hz), 7.15–7.17 (1H, m), 7.09 (1H, s), 6.63 (4H, s), 3.80–3.88 (2H, m), 2.95–3.40 (2H, m), 2.73–2.80 (2H, m), 2.48–2.57 (4H, m), 2.46 (3H, s), 1.65–1.73 (4H, m) (1) (DMSO-d$_6$) | FAB-Mass 425 (M + H)$^+$ |
| 81 | [structure: Cl-benzoxazepinone-N-butyl-tetrahydropyridine-pyridine] | 158–161° C. (2) (acetone) | 3428 2946 2672 1648 1540 1454 1378 1330 1241 (2) (KBr) | 9.71 (1H, br), 8.55–8.59 (1H, m), 7.89–7.91 (1H, m), 7.79 (1H, d, J = 8 Hz), 7.60 (1H, t, J = 8 Hz), 7.31–7.40 (3H, m), 7.14–7.18 (2H, m), 3.84–3.87 (2H, m), 3.55–3.58 (2H, m), 2.95–3.18 (5H, m), 2.04–2.15 (4H, m), 1.68–1.89 (4H, m) (2) (DMSO-d$_6$) | FAB-Mass 412 (M + H)$^+$ |
| 82 | [structure: Cl-benzoxazepinone-N-pentyl-piperidine-pyridine] | 145–147° C. (2) (MeOH-acetone) | 3416 2928 2695 1652 1604 1560 1455 1381 1340 1198 (2) (KBr) | 10.74 (1H, br), 7.95–7.97 (1H, m), 7.79 (1H, dd, J = 2, 8 Hz), 7.70–7.72 (1H, m), 7.60 (1H, t, J = 8 Hz), 7.42–7.44 (1H, m), 7.34 (1H, t, J = 8 Hz), 7.14–7.17 (2H, m), 6.74–6.76 (1H, m), 4.03–4.08 (1H, m), 3.84–3.87 (3H, m), 3.64–3.67 (1H, m), 3.21–3.25 (3H, m), 2.91–2.93 (2H, m), 1.84–1.86 (2H, m), 1.70–1.76 (2H, m), (2) (DMSO-d$_6$) | FAB-Mass 410 (M + H)$^+$ |
| 83 | [structure: Cl-benzoxazepinone-N-butyl-tetrahydropyridine-pyridine isomer] | amorphous (1) | 3439 2933 1700 1683 1630 1570 1433 1291 (1) (KBr) | 8.50 (1H, d, J = 5 Hz), 7.74 (1H, t, J = 7 Hz), 7.79 (1H, d, J = 7 Hz), 7.58–7.62 (2H, m), 7.33 (1H, t, J = 7 Hz), 7.25 (1H, t, J = 5 Hz), 7.12–7.15 (2H, m), 6.72 (1H, s), 6.60 (4H, s), 3.90–3.94 (2H, m), 3.64–3.68 (2H, m), 2.73–2.80 (4H, m), 2.39–2.40 (2H, m), 1.66–1.71 (4H, m) (1) (DMSO-d$_6$) | FAB-Mass 410 (M + H)$^+$ |

| Ex. | Chemical structure | m.p. (Recrystallization solvent) | IR (cm⁻¹) | NMR (δ ppm) | MS/Element analysis |
|---|---|---|---|---|---|
| 84 | (structure: benzoxazepinone with N-butyl-4-(2-pyridyl)-tetrahydropyridine, Me substituent) | 165–168° C. (1) (acetone-Et₂O) | 2934 2594 1684 1630 1457 1400 1350 1308 1209 1100 (1) (KBr) | 8.51 (1H, d, J = 5 Hz), 7.68–7.75 (2H, m), 7.46–7.53 (2H, m), 7.20–7.25 (2H, m), 7.05 (1H, dd, J = 8 Hz), 6.66 (1H, s), 6.60 (4H, s), 6.56 (1H, s), 3.72–3.78 (2H, m), 3.19–3.23 (2H, m), 2.70–2.73 (2H, m), 2.50–2.59 (4H, m), 1.57–1.61 (4H, m) (1) (DMSO-d₆) | FAB-Mass 390 (M + H)⁺ |
| 85 | (structure: benzoxazepinone with N-butyl-4-(2-pyridyl)-tetrahydropyridine, Et substituent) | amorphous (1) | 3440 2935 1705 1684 1636 1571 1492 1421 1296 (1) (KBr) | 8.55 (1H, d, J = 5 Hz), 7.85 (1H, d, J = 7 Hz), 7.62 (1H, t, J = 7 Hz), 7.33–7.39 (1H, m), 7.19 (1H, t, J = 7 Hz), 7.11 (1H, t, J = 5 Hz), 6.97 (1H, d, J = 7 Hz), 6.62–6.65 (1H, m), 6.44 (1H, s), 3.80–3.85 (2H, m), 3.21–3.24 (2H, m), 2.65–2.76 (4H, m), 2.53–2.57 (2H, m), 2.18 (2H, q, J = 7 Hz), 0.95 (3H, t, J = 7 Hz) (1) (DMSO-d₆) | FAB-Mass 404 (M + H)⁺ |

[1] Indicated as (1) as fumarate.
[2] Indicated as (2) as hydrochloride.

What is claimed is:

1. A pyrimidine derivative having the following formula (VI) and its salts:

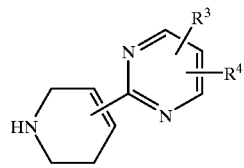
(VII)

wherein, $R^3$ and $R^4$ are each independently selected from the group consisting of a hydrogen atom, halogen atom, $C_1$ to $C_4$ alkyl group, hydroxy group, and $C_1$ to $C_4$ alkoxy group, and a dotted line is an optional double bond.

2. The pyrimidine derivative according to claim 1, wherein $R^3$ is a hydrogen atom.

3. The pyrimidine derivative according to claim 1, wherein $R^4$ is a hydrogen atom.

4. The pyrimidine derivative according to claim 1, wherein $R^3$ and $R^4$ are both hydrogen atoms.

5. The pyrimidine derivative according to claim 1, wherein the optional double bonds are present.

6. The pyrimidine derivative according to claim 1, wherein the optional double bonds are not present.

7. The pyrimidine derivative according to claim 1 wherein $R^3$ is a $C_1$ to $C_4$ alkyl group.

8. The pyrimidine derivative according to claim 1, wherein $R^3$ is a methyl group.

9. The pyrimidine derivative according to claim 1, wherein $R^3$ is a $C_1$ to $C_4$ alkoxy group.

10. The pyrimidine derivative according to claim 1, wherein $R^4$ is a $C_1$ to $C_4$ alkoxy group.

11. The pyrimidine derivative according to claim 9, wherein $R^3$ is a methoxy group.

12. The pyrimidine derivative according to claim 10, wherein $R^4$ is a methoxy group.

13. The pyrimidine derivative according to claim 1, wherein $R^4$ is a halogen.

14. The pyrimidine derivative according to claim 13, wherein $R^4$ is a fluoro group.

15. The pyrimidine derivative according to claim 1 and its salts, of formula (VIIa):

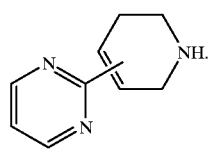
(VIIa)

16. The pyrimidine derivative according to claim 1 and its salts, of formula (VIIb):

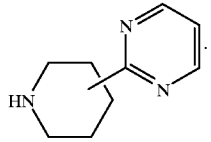
(VIIb)

17. The pyrimidine derivative according to claim 1 and its salts, of formula (VIIc):

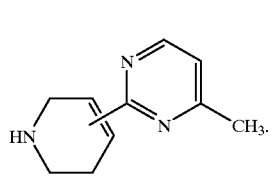
(VIIc)

18. The pyrimidine derivative according to claim 1 and its salts, of formula (VIId):

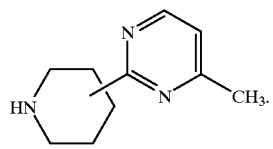
(VIId)

19. The pyrimidine derivative according to claim 1 and its salts, of formula (VIIe):

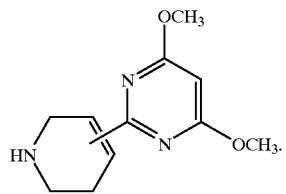
(VIIe)

20. The pyrimidine derivative according to claim 1 and its salts, of formula (VIIf):

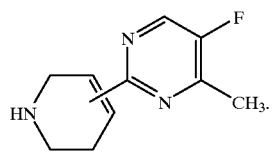
(VIIf)

* * * * *